United States Patent
Dudley et al.

(10) Patent No.: US 6,503,894 B1
(45) Date of Patent: Jan. 7, 2003

(54) PHARMACEUTICAL COMPOSITION AND METHOD FOR TREATING HYPOGONADISM

(75) Inventors: Robert E. Dudley, Kenilworth, IL (US); S. George Kottayil, Long Grove, IL (US); Olivier Palatchi, L'Hay les Roses (FR)

(73) Assignees: Unimed Pharmaceuticals, Inc., Marietta, GA (US); Laboratories Besins Iscovesco, Herndon, VA (US)

( * ) Notice: Subject to any disclaimer, the term of this patent is extended or adjusted under 35 U.S.C. 154(b) by 0 days.

(21) Appl. No.: 09/651,777

(22) Filed: Aug. 30, 2000

(51) Int. Cl.$^7$ ............................................... A61K 31/56
(52) U.S. Cl. ...................... 514/178; 514/177
(58) Field of Search ............................. 514/178, 396, 514/406, 415, 177

(56) References Cited

U.S. PATENT DOCUMENTS

| | | |
|---|---|---|
| 2,155,658 A | 4/1939 | Herrman et al. |
| 3,068,188 A | 12/1962 | Beste et al. |
| 3,218,283 A | 11/1965 | Miller |
| 3,887,699 A | 6/1975 | Yolles |
| 3,888,995 A | 6/1975 | Katz et al. |
| 3,939,111 A | 2/1976 | Schollenberger et al. |
| 4,009,254 A | 2/1977 | Renold |
| 4,083,973 A | 4/1978 | Van der Vies |
| 4,161,948 A | 7/1979 | Bichon |
| 4,442,094 A | 4/1984 | Atkinson et al. |
| 4,447,562 A | 5/1984 | Ivani |
| 4,478,822 A | 10/1984 | Haslam et al. |
| 4,496,556 A | 1/1985 | Orentreich |
| 4,563,473 A | 1/1986 | Hofman et al. |
| 4,631,188 A | 12/1986 | Stoy et al. |
| 4,690,775 A | 9/1987 | Schott et al. |
| 4,695,465 A | 9/1987 | Kigasawa et al. |
| 4,704,282 A | 11/1987 | Campbell et al. |
| 4,725,439 A | 2/1988 | Campbell et al. |
| 4,745,160 A | 5/1988 | Churchill et al. |
| 4,767,627 A | 8/1988 | Caldwell et al. |
| 4,780,320 A | 10/1988 | Baker |
| 4,788,062 A | 11/1988 | Gale et al. |
| 4,863,970 A | 9/1989 | Patel et al. |
| 4,920,203 A | 4/1990 | Tang et al. |
| 4,946,870 A | 8/1990 | Partain, III et al. |
| 4,981,696 A | 1/1991 | Loomis et al. |
| 5,013,553 A | 5/1991 | Southard et al. |
| 5,053,227 A | 10/1991 | Chiang et al. |
| 5,059,603 A | 10/1991 | Rubin |
| 5,071,657 A | 12/1991 | Oloff et al. |
| 5,152,997 A | 10/1992 | Ebert et al. |
| 5,231,087 A | 7/1993 | Thornfeldt |
| 5,256,652 A | 10/1993 | El-Rashidy |
| 5,324,521 A | 6/1994 | Gertner et al. |
| 5,326,790 A | 7/1994 | Thornfeldt |
| 5,332,577 A | 7/1994 | Gertner et al. |
| 5,340,586 A | 8/1994 | Pike et al. |
| 5,362,497 A | 11/1994 | Yamada et al. |
| 5,413,794 A | 5/1995 | Suzuki et al. |
| 5,446,070 A | 8/1995 | Mantelle |
| 5,460,820 A | 10/1995 | Ebert et al. |
| 5,610,150 A | 3/1997 | Labrie |
| 5,629,021 A | 5/1997 | Wright |
| 5,641,504 A | 6/1997 | Lee et al. |
| 5,643,899 A | 7/1997 | Elias et al. |

(List continued on next page.)

FOREIGN PATENT DOCUMENTS

| | | | |
|---|---|---|---|
| DE | 3238984 | 10/1982 | |
| EP | 0581587 A2 | 2/1994 | |
| EP | 0197753 | 10/1996 | |
| EP | 0804926 | 4/1997 | |
| FR | 2515041 | 4/1983 | |
| FR | 2518879 | 7/1983 | |
| FR | 2519252 | 7/1983 | |
| FR | 2705572 | 12/1994 | |
| GB | 2109231 | 6/1983 | |
| WO | WO 93/25168 A1 | 12/1993 | |
| WO | 9408590 | 4/1994 | |
| WO | 9421230 | 9/1994 | |
| WO | 9421271 | 9/1994 | |
| WO | WO-96/27372 A1 * | 9/1996 | .......... A61K/31/21 |
| WO | 9636339 | 11/1996 | |
| WO | 9743989 | 11/1997 | |
| WO | 9808547 | 3/1998 | |
| WO | 9824451 | 6/1998 | |
| WO | WO 98/34621 A1 | 8/1998 | |
| WO | 9837871 | 9/1998 | |
| WO | WO-99/24041 A1 * | 5/1999 | .......... A61K/31/56 |
| WO | 9932107 | 7/1999 | |
| WO | WO 99/66870 A1 | 12/1999 | |
| WO | 0024362 | 5/2000 | |
| WO | WO 00/66870 A2 | 8/2000 | |
| WO | 0076522 | 12/2000 | |
| WO | WO 01/43775 A2 | 6/2001 | |

OTHER PUBLICATIONS

The trademark record for Androgel® Mar. 16, 1999.*
Manos, *FDA Approves Gel to Treat Low Testosterone Levels*, www.testocreme.com (Downloaded May 9, 2001).
*Unimed Pharmaceuticals' Androgel Shows Solid Promise for Men*, Fertility Industry News, www.INCIID.com (Aug. 19, 1998).
Lacayo, *Are You Man Enough?*, Time Europe, www.Time.com, vol. 155, No. 16 (Apr. 24, 2000).
*MacroChem Accelerates Development of Top For Impotence*, www.pslgroup.com (Apr. 10, 1997).
Kaufman, *Efficacy and Safety of a New, Topical Testosterone Gel (T–gel) For Male Hormonal Supplementation*, International Journal of Impotence Research, vol. 12, Supplement 3, p. S75 (B9) (Sep. 2000).

(List continued on next page.)

Primary Examiner—Russell Travers
Assistant Examiner—S. Jiang
(74) Attorney, Agent, or Firm—Mayer, Brown, Rowe & Maw; Joseph A. Mahoney; Thomas R. Stiebel

(57) ABSTRACT

A pharmaceutical composition useful for treating hypogonadism is disclosed. The composition comprises an androgenic or anabolic steroid, a C1–C4 alcohol, a penetration enhancer such as isopropyl myristate, and water. Also disclosed is a method for treating hypogonadism utilizing the composition.

42 Claims, 40 Drawing Sheets

U.S. PATENT DOCUMENTS

| | | |
|---|---|---|
| 5,648,350 A | 7/1997 | DeLignieres |
| 5,651,973 A | 7/1997 | Moo-Young et al. |
| 5,654,337 A | 8/1997 | Roentsch et al. |
| 5,656,286 A | 8/1997 | Miranda et al. |
| 5,708,038 A | 1/1998 | Davis |
| 5,716,638 A | 2/1998 | Touitou |
| 5,719,197 A | 2/1998 | Kanios et al. |
| 5,723,114 A | 3/1998 | Thornfeldt et al. |
| 5,744,162 A | 4/1998 | Okabe et al. |
| 5,760,096 A | 6/1998 | Thornfeldt et al. |
| 5,770,606 A | 6/1998 | El Rashidy et al. |
| 5,776,923 A | 7/1998 | Labrie |
| 5,788,983 A | 8/1998 | Chien et al. |
| 5,807,849 A | 9/1998 | Labrie |
| 5,807,957 A | 9/1998 | Samour et al. |
| 5,837,289 A | 11/1998 | Grasela et al. |
| 5,847,128 A | 12/1998 | Martin et al. |
| 5,855,905 A | 1/1999 | Oettel et al. |
| 5,874,074 A | 2/1999 | Smith |
| 5,908,619 A | 6/1999 | Scholz |
| 5,908,638 A | 6/1999 | Huber et al. |
| 5,932,227 A | 8/1999 | Higo et al. |
| 5,955,455 A | 9/1999 | Labrie |
| 5,968,919 A | 10/1999 | Samour et al. |
| 6,010,716 A | 1/2000 | Saunal et al. |
| 6,019,997 A | 2/2000 | Scholz et al. |
| 6,037,346 A | 3/2000 | Doherty, Jr. et al. |
| 6,075,028 A | 6/2000 | Graham |
| 6,077,841 A | 6/2000 | Sui et al. |
| 6,087,368 A | 7/2000 | Macor et al. |
| 6,117,446 A | 9/2000 | Place |
| 6,127,363 A | 10/2000 | Doherty et al. |
| 6,156,753 A | 12/2000 | Doherty et al. |
| 6,238,284 B1 | 5/2001 | Dittgen et al. |
| 6,299,900 B1 | 10/2001 | Reed et al. |
| 2001/0018073 A1 | 8/2001 | Dittgen et al. |
| 2001/0023261 A1 | 9/2001 | Ryoo et al. |
| 2001/0033870 A1 | 10/2001 | Luo et al. |
| 2001/0036483 A1 | 11/2001 | Luo et al. |
| 2001/0051166 A1 | 12/2001 | Luo et al. |

OTHER PUBLICATIONS

Longstreth, et al., *Transdermal Testosterone Pharmacokinetics Remain Unchanged With Prolonged Treatment,* Unimed Pharmaceuticals (Oct. 31, 2000).

Ringham, et al., *Dose Proportionality and Systemic Bioavailability of a Testosterone Topical Gel In Hypogonadal Men,* Unimed Pharmaceuticals (Oct. 31, 2000).

Miller, et al., *Androgen Deficiency in Women with Hypopituitarism, The Journal of Clinical Endocrinology & Metabolism,* vol. 86, No. 2, pp. 561–567 (2001).

Veldhuis, et al., *Muting of Androgen Negative Feedback Unveils Impoverished Gonadotropin–Releasing Hormone/Luteinizing Hormone Secretory Reactivity in Healthy Older Men, The Journal of Clinical Endocrinology & Metabolism,* vol. 86, No. 2, pp. 529–535. (2001).

Swerdloff, et al., *Long Term Pharmacokinetics of Transdermal Testosterone Gel Versus Testosterone Patch in Hypogonadal Men,* 2347 Male Reproductive Poster Session, Board 578 (Jun. 22, 2000).

Wang, et al., *Effects of Transdermal Testosterone Gel on Bone Turnover Markers and Bone Mineral Density in Hypogonadal Men,* 2348 Male Reproductive Poster Session, Board 579 (Jun. 22, 2000).

Wang, et al., *Effects of Transdermal Testosterone Gel on Bone Turnover Markers and Bone Mineral Density in Hypogonadal Men, Clinical Endocrinology,* vol. 54, pp. 1–13 (2001).

Wang, et al., *Transdermal Testosterone Gel Improves Sexual Function, Mood, Muscle Strength, and Body Composition Parameters in Hypogonadal Men, Basic Science: Reproduction–Gonadal Control (Male),* Male Reproduction Oral Session, No. 1360 (Jun. 24, 2000).

*Unimed Pharmaceuticals' Androgel Shows Solid Promise for Men;* Fertility Industry News, www.INCIID.com (Aug. 19, 1998).

*Bentley Pharmaceuticals Announces License Agreement for Its Topical Testosterone Gel Formulation;* Li, www.UVentures.com (Dec. 18, 2000).

Ruggs, *Unimed Begins Pivotal Clinical Trial For Innovative Testosterone Gel,* Unimed News Release, pp. 1–2 (Mar. 31, 1997).

Androgel 1% (testosterone gel) CIII.; www.Androgel.com, pp. 1–2.

Wang, et al., *Effects of Transdermal Testosterone Gel on Bone Turnover Markers and Bone Mineral Density in Hypogandal Men, Clinical Science: Reproduction (Male)–Prostate,* Male Reproduction Poster Session, No. 2348 (Jun. 22, 2000).

Swerdloff, et al., *Long Term Pharmakonetics of Transdermal Testosterone Gel Versus Testosterone Patch in Hypogonadal Men, Clinical Science: Reproduction (Male)–Prostate,* Male Reproduction Poster Session, No. 2347 (Jun. 22, 2000).

*Trials for the Treatment of Wasting, AIDS Treatment Data Network,* www.aidsinfonyc.org (Downloaded Oct. 8, 1998).

De Lunardo, et al., *Determination of Acceptability of 2 Cutaneous Estradiol Gels, In A Dose of 1.5 mg Daily, J. Gynecol. Obstet. Biol. Reprod. (Paris),* vol. 29, No. pp. 509–516, (Sep. 2000).

Zartarian, et al., *Comparative Evaluation of the Acceptability of a New Estradiol Gel TX11323(A) and a Reference Gel, J. Gynecol. Obstet. Biol. Reprod. (Paris),* vol. 25, No. 5, pp. 451–456 (1996).

Simon, et al., *The Absorption of Oral Micronized Progesterone: The Effect of Food, Dose Proportionality, and Comparison With Intramuscular Progesterone, Fertility and Sterility,* vol. 60, No. 1, pp. 26–33 (Jul. 1993).

Vaubourdolle, et al., *Effect of Dihydrotestosterone on the Rate of Ethanol Elimination in Healthy Men, Alcohol Clin. Exp. Res.,* vol. 15, No. 2, pp. 238–240 (Mar. 1991).

Fournier, et al., *Value of Percutaneous Estrogen Solution in Stopping Lactation, Rev. Fr. Gynecol. Obstet.,* vol. 85, No. 12, pp. 715–719 (Dec. 1990).

Simon, et al., *Percutaneous Absorption of 17 Beta–Estradiol in Ovariectomized Rhesus Monkeys: Skin and Serum Pharmacokinetics, Fertility and Sterility,* vol. 53, No. 3, pp. 561–565 (Mar. 1990).

Rodriguez, *Study of Drug to Preserve Lean Muscle Mass Recruiting Patients, ALPA 9701:* Study Recruiting Patients, www.apla.org (Downloaded Oct. 8, 1998).

*HIV Wasting Treatment: Nandrolone Decanoate,* www.hivinsite.ucsf.edu (Aug. 1, 1995).

Vergel, *Anabolic Steroids: A Practical Guide, CRIA Update,* vol. 7, No. 3 (Summer 1998).

*HIV Wasting Syndrome,* www.thebody.com (May 1997).

Tirassa, et al., *High–Dose Anabolic Androgenic Steroids Modulate Concentrations of Nerve Growth Factor and Expression of its Low Affinity Receptor (p75–NGFr) in Male Rat Brain*, Journal of Neuroscience Research, vol. 47, No. 2, pp. 198–207 (Jan. 15, 1997).

Mooney, *Frequency of Administration—Testosterone & Nandrolone*, vol. 1, No. 4, www.medibolics.com (Downloaded Oct. 8, 1998).

*Anabolic Steroids*, Project Inform, Anabolic Steroids Quick Sheet (Dec. 1997).

*Anabolic Steroid Boosts Weight*, GMHC Treatment Issues, vol. 10, No. 9 (Sep. 1996).

*Anabolic Steroids*, Project Inform Hotline Handout, www.projinf.org. (Downloaded Oct. 8, 1998).

*Anabolic Steroids—A Simple Facts Sheet From The Network*, www.network/simple/steroids (Downloaded Oct. 27, 1998).

*USP Drug Information—Anabolic Steroids (Systemic)*, MayoClinic, www.mayohealth.org (Downloaded Oct. 8, 1998).

Mooney, *Anabolic Steroids For AIDS Therapy: Differences Between Analogs*, No. 1, www.digiweb.com. (Jul. 1998).

Bisschop, et al., *Effects of Nandrolone Decanoate on Respiratory and Peripheral Muscles in Male and Female Rats*, www.uth.tms.edu. (1996, Downloaded Oct. 8, 1998).

*HIV/AIDS Clinical Trials in the New Orleans Area*, ACTG 329, www.tmc.tulane.edu (Downloaded Oct. 8, 1998).

Need, et al., *Effects of Nandrolone Therapy on Forearm Bone*, www.medmedia.com (Downloaded Oct. 8, 1998).

*Testocreme—No Shots, No Pills, No Patches*, www.testocreme.com (Downloaded Jul. 10, 2000).

*Testosterone Therapy—for Women?*, Health News, www.onhealth.com (May 7, 1996).

*ENDO 99: Testosterone Patch Effective For Diminished Sexual Function in Surgically Menopausal Women*, www.pslgroup.com (Jun. 15, 1999).

Howland, *The "Other" Hormone Replacement Therapy: Testosterone in Menopausal Women*, HealthGate, www.bewell.com (Aug. 7, 2000).

*Menopause and Testosterone*, www.womenshealth.com (Downloaded Aug. 7, 2000).

*Data Supports Safety of Estratest For Men, Doctor's Guide*, www.pslgroup.com (Mar. 9, 1998).

*Testosterone's Role in the Female Sex Drive*, USA Today News, www.usatoday.com (Apr. 8, 1996).

Bartnof, *Testosterone Therapy Causes Menstruation to Return in Women with AIDS–Related Wasting*, www.hivandhepatitis.com (Oct. 12, 1999).

*Testosterone 'Aids Post–Menopausal Women'*, BBC News Online: Health, www.bbc.co.uk. (Jun. 14, 1999).

*Alternative to Viagra For Women!*, www.mdhealthline.com (Downloaded Aug. 7, 2000).

Kalantaridou, et al., *Transdermal Testosterone Replacement for Young Women with Spontaneous Premature Ovarian Failure: A Pilot Study*, No. 2322, www.abstracts–on–1 (Downloaded Aug. 7, 2000).

Rosano, et al., *Antianginal and Lipid Lowering Effect of Chronic Oral Androgen Supplementation in Elderly Male Patients with Coronary Heart Disease*, JACC, Abstract No. 835–4 (Feb. 2001).

Mollgaard, et al., *Permeation of Estradiol Through the Skin—Effect of Vehicles*, International Journal of Pharmaceuticals, vol. 15, pp. 185–197 (1983).

Ostrenga, et al., *Significance of Vehicle Composition II: Prediction of Optimal Vehicle Composition*, Journal of Pharmaceutical Sciences, vol. 60, No. 8, pp. 1180–1183 (Aug. 1971).

Cooper, et al., *Effect of Fatty Acids and Alcohols on the Penetration of Acyclovir Across Human Skin in Vitro*, Journal of Pharmaceutical Sciences, vol. 74, No. 6, pp. 688–689 (Jun. 1985).

Ostrenga, et al., *Significance of Vehicle Composition I: Relationship Between Topical Vehicle Composition, Skin Penetrability, and Clinical Efficacy*, Journal of Pharmaceutical Sciences, vol. 60, No. 8, pp. 1175–1179 (Aug. 1971).

Maibach, et al., *The Effect of DMSO on Percutaneous Penetration of Hydrocortisone and Testosterone in Man*, Annals New York Academy of Sciences, pp. 423–427.

Mollgaard, et al., *Vehicle Effect on Topical Drug Delivery*, Acta Pharm. Suec., vol. 20, pp. 433–442 (1983).

Misra, et al., *Biphasic Testosterone Delivery Profile Observed With Two Different Transdermal Formulations*, Pharmaceutical Research, vol. 14, No. 9, pp. 1264–1268 (1997).

Sitruk–Ware, *Percutaneous and Transdermal Oestrogen Replacement Therapy*, Annals of Medicine, vol. 25, pp. 77–82 (1993).

Goodman, et al., *Action of Skin Permeation Enhancers Azone, Oleic Acid and Decylmethyl Sulphoxide: Permeation and DSC Studies*.

Woodford, et al., *Optimization of Bioavailability of Topical Steroids: Thermodynamic Control*, The Journal of Investigative Dermatology, vol. 79, No. 6, pp. 388–391 (Dec. 1982).

*Androgel*, The Medical Letter On Drugs And Therapeutics, vol. 42 (Issue 1080), pp. 49–52 (Jun. 12, 2000).

*Never Too Buff*, Time Europe, www.time.com, vol. 155, No. 16 (Apr. 24, 2000).

Androgel Package Insert, Dec. 2000.

Jarkander–Rolff, et al., *Transdermal Application of A Testosterone Gel—A Pharmacokinetic Study*.

*Androgel—Phase III Clinical Trial*, Gynecology, (Undated).

Gefael, *Graeme's Testosterone Page*, www.voyager.co.nz (May 12, 2000).

*Estrogel*, www.netdoktor.dk/medicin/Fakta/Estrogel (Downloaded Jun. 26, 2001).

*La Sexualite . . . , L'Androgel, Le Gel Miracle*, www.aci–multimedia.net/feminin/androgel (Downloaded May 9, 2001).

Stehli, et al., *Info . . . , Info . . . , Info . . . —Androgel*, www.mageos.ifrance.com/nade38/androgel (Downloaded May 9, 2001).

Cherrier, et al., *T–Gel Study: Cognitive Effects of Exogenous Testosterone Manipulation in Hypogonadal Men* (Jun. 7, 1999).

Bentley Pharmaceuticals Announce Research and Licensing Agreements For Intranasal Pain Management and Topical Hormone Replacement Therapy, www.bentleypharm.com (downloaded Nov. 17, 2001).

Gennaro, *Remington: The Science and Practice of Pharmacy*, 20th Edition, Chapter 44, pp. 842–843 (2000).

Walters, *Penetration Enhancers and Their Use in Transdermal Therapeutic Systems*, pp. 202–227 (1990).

Yu, et al., *Transdermal Testosterone Administration in Hypogonadal Men: Comparison of Pharmacokinetics at Different Sites of Application and at the First and Fifth Days of Application*, J Clin Pharmacol, 37:1129–1138 (1997).

Yu, et al., *Testosterone Pharmacokinetics after Application of an Investigational Transdermal System in Hypogonadal Men;* J Clin Pharmacol, 37:1139–1145 (1997).

Cunningham, et al., *Testosterone Transdermal Delivery System,* Pharmacology, Biology, and Clinical Applications of Androgens ; 42:437–447 1996 Wiley–Liss, Inc.

Carey, et al., *Transdermal Testosterone Treatment of Hypogonadal Men,* The Journal of Urology, vol. 140, pp. 76–79, (Jul. 1988).

Bals–Pratsch, et al., *Substitution Therapy of Hypogonadal Men with Transdermal Testosterone Over One Year,* Acta Endocrinologica (Copenh) 1988, 118: 7–13.

Meikle, et al., *Androderm: A Permeation Enhanced Non–Scrotal Testosterone Transdermal System for the Treatment of Male Hypogonadism,* Pharmacology, Biology, and Clinical Applications of Androgens, 43:449–457, 1996 Wiley–Liss, Inc.

Arver, et al., *Long–Term Efficacy and Safety of a Permeation–Enhanced Testosterone Transdermal System in Hypogonadal Men,* Clinical Endocrinology, 47: 727–737 (1997).

Brocks, et al., *Pharmacokinetics of Testosterone in Hypogonadal Men After Transdermal Delivery: Influence of Dose,* J Clin Pharmacol 1996; 36:732–739.

Mazer, et al., *Enhanced Transdermal Delivery of Testosterone: A New Physiological Approach for Androgen Replacement in Hypogonadal Men,* Journal of Controlled Release, 19 (1992) 347–362.

Schurmeyer, et al, *Comparative Pharmacokinetic of Testosterone Enanthate and Testosterone Cyclohexanecarboxylate as Assessed by Serum and Salivary Testosterone Levels in Normal Men,* International Journal of Andrology, 7 (1984) 181–187.

Behre, et al., *Testosterone Buciclate (20 Aet–1) in Hypogonadal Men: Pharmacokinetics and Pharmacodynamics of the New Long–Acting Androgen Ester,* Journal of Endocrinology and Metabolism, vol. 75, No. 5, pp. 1204–1210 (1992).

Jockenhovel, et al., *Pharmacokinetics and Pharmacodynamics of Subcutaneous Testosterone Implants in Hypogonadal Men,* Clinical Endocrinology, (1996) 45 61–71.

*Sexual Dysfunction in the Male—Sexual Arousal Disorder,* The Merck Manual, Sixteenth Edition, Ch. 139, pp. 1575–1576 (1992).

Weinbauer, et al., *Pharmacokinetics and Pharmacodynamics of Testosterone Enanthate and Dihydrotestosterone Enanthate in Non–Human Primates,* Acta Endocrinologica (Copenh) 1990, 122, 4: 432–442.

Bagatell, et al., *Effects of Endogenous Testosterone and Estradiol on Sexual Behavior in Normal Young Men,* Journal of Clinical Endocrinology and Metabolism, vol. 78, No. 3, pp. 711 (1994).

Bancroft, *Endocrinology of Sexual Function,* Clinics in Obstetrics and Gynaecology, vol. 7, No. 2, Aug. 1980, p. 253.

Knussmann, et al., *Relations Between Sex Hormone Levels and Sexual Behavior in Men,* Archives of Sexual Behavior, vol. 15, No. 5, p. 429 (1986).

Kraemer, et al., *Orgasmic Frequency and Plasma Testosterone Levels in Normal Human Males,* Archives of Sexual Behavior, vol. 5, No. 2, p. 125 (1976).

Anderson, et al, *The Effects of Exogenous Testosterone on Sexuality and Mood of Normal Men,* Journal of Clinical Endocrinology and Metabolism, vol. 75, No. 6, p. 1503 (1992).

Tsitouras, *Effects of Age on Testicular Function,* Endocrinology and Metabolism Clinics, vol. 16, No. 4, p. 1045–1059 (Dec. 1987).

Vermeulen, et al., *Long–Term Transdermal Dihydrotestosterone Therapy: Effects on Pituitary Gonadal Axis and Plasma Lipoproteins,* Maturitas, 7 (1985) 281–287.

Gooren, *Androgen Levels and Sex Functions in Testosterone–Treated Hypogonadal Men,* Archives of Sexual Behavior, vol. 16, No. 6, p. 463–473 (1987).

McClure, et al., *Hypogonadal Impotence Treated by Transdermal Testosterone,* Urology, vol. XXXVII, No. 3, pp. 224–228 (Mar. 1991).

Chemana, et al., *Percutaneous Absorption of 5α–dihydrotestosterone in Man II. Percutaneous Administration of 5α–dihydrotestosterone in Hypogonadal Men with Idiopathic Haemochromatosis; Clinical, Metabolic and Hormonal Effectiveness,* International Journal of Andrology, 5 (1982) 595–606.

de Lignieres, *Transdermal Dihydrotestosterone Treatment of Andropause,* Annals of Medicine 25: 235–241, 1993.

Skakkebaek, et al., *Androgen Replacement with Oral Testosterone Undecanoate in Hypogonadal Men: A Double Blind Controlled Study,* Clinical Endocrinology (1981) 14, 49–61.

Cunningham, et al, *Testosterone Replacement Therapy and Sleep–Related Erections in Hypogonadal Men,* Journal of Clinical Endocrinology and Metabolism, vol. 70, No. 3, 792–797.

Rousseau, et al, *Inhibition of Steroid–Protein Interactions by Dicyclohexane Derivatives,* J Steroid Biochem, vol. 31, No. 4B, pp 691–697 (1988).

Mooradian, et al., *Biological Actions of Androgens,* Endocrine Reviews, vol. 8, No. 1, pp. 1–28 (1987).

Mantzoros, et al, *Contribution of Dihydrotestosterone to Male Sexual Behaviour,* British Medical Journal, No. 6990, vol. 310, pp 1289–1291 (May 20, 1995).

Davidson, et al., *Hormonal Replacement and Sexuality in Men,* Clinics in Endocrinology and Metabolism, vol. 11, No. 3, pp. 599–623 (Nov. 1982).

Hardy, et al., *Endocrine Assessment of Impotence—Pitfalls of Measuring Serum Testosterone Without Sex–Hormone–Binding Globulin,* Postgrad Med J (1994) 70, 836–837.

Lewis, et al, *Serum 5α–Dihydrotestosterone and Testosterone Changes with Age in Man,* Acta Endocrinologica, 82 (1976) 444–448.

Cunningham, et al, *Plasma Sex Hormone–Binding Globulin Levels Decrease During the Second Decade of Life Irresponsive of Pubertal Status,* Journal of Clinical Endocrinology and Metabolism, vol. 58, No. 5, pp. 915–918 (1984).

Morley, et al., *Longitudinal Changes in Testosterone, Luteinizing Hormone, and Follicle–Stimulating Hormone in Healthy Older Men,* Metabolism, vol. 46, No. 4 (Apr. 1997), pp. 410–413.

Damassa, et al., *Sex Hormone–Binding Globulin and Male Sexual Development,* Neuroscience and Biobehavioral Reviews, vol. 19, No. 2, pp. 165–175 (1995).

Behre, et al., *Long–Term Effect of Testosterone Therapy on Bone Mineral Density in Hypogonadal Men,* Journal of Clinical Endocrinology and Metabolism, vol. 82, No. 8, pp. 2389 1997.

Leifke, et al., *Effects of Testosterone Replacement Therapy on Cortical and Trabecular Bone Mineral Density, Verbetral Body Area and Paraspinal Muscle Area in Hypogonadal Men,* European Journal of Endocrinology (1998) 138 51–58.

Wang, et al., *Comparative Pharmacokinetics of Three Doses of Percutaneous Dihydrotestosterone Gel in Healthy Elderly Men—A Clinical Research Center Study,* Journal of Clinical Endocrinology and Metabolism, vol. 83, No. 8, pp 2749–2757 (1998).

Dobs, et al., *Pharmacokinetics, Efficacy and Safety of a Permeation–Enhanced Testosterone Transdermal System in Comparison with Bi–Weekly Injections of Testosterone Enanthate for the Treatment of Hypogonadal Men,* The Journal of Clinical Endocrinology and Metabolism, vol. 84, No. 10, pp. 3469–3478 (1999).

Snyder, et al., *Effect of Testosterone Treatment of Bone Mineral Density in Men Over 65 Years of Age,* The Journal of Clinical Endocrinology and Metabolism, vol. 84, No. 6, pp. 1966–1972 (1999).

Parker, et al., *Experience with Transdermal Testosterone Replacement Therapy for Hypogonadal Men,* Clinical Endocrinology (1999) 50, 57–62.

Behre, et al., *Long–Term Substitution Therapy of Hypogonadal Men with Transscrotal Testosterone Over 7–10 Years,* Clinical Endocrinology (1999) 50, 629–635.

Behre, et al., *Intramuscular Injection of Testosterone Undecanoate for the Treatment of Male Hypogonadism: Phase I Studies,* European Journal of Endocrinology (1999) 140 414–419.

Bhasin, et al., *Therapeutic Perspective—Issues in Testosterone Replacement in Older Men,* Journal of Clinical Endocrinology and Metabolism, vol. 83, No. 10, pp. 3435–3448 (1998).

McClellan, et al., *Transdermal Testosterone,* ADIS New Drug Profile—Drugs, Feb. 1998 55(2): 253–258.

Abitbol, et al., *Sex Hormones and the Female Voice,* J Voice, Sep. 1999; 13(3): 424–46.

Almeida, *Sex Playing with the Mind. Effects of Oestrogen and Testosterone Mood and Congition,* Arq Neuropsiquiatr, Sep. 1999; 57(3A): 701–6.

Angold, et al., *Pubertal Changes in Hormone Levels and Depression in Girls,* Psychol Med Sep. 1999; 29(5): 1043–53.

Barrett–Conner, et al., *Cognitive Function and Endogenous Sex Hormones in Older Women,* J Am Geriatr Soc, Nov. 1999; 47(11): 1289–93.

Barrett–Conner, et al., *A Two–Year, Double–Blind Comparison of Estrogen–Androgen and Conjugated Estrogens in Surgically Menopausal Women. Effects Bone Mineral Density, Symptoms and Lipid Profiles,* J Reprod Med, Dec. 1999; 44(12): 1012–20.

Drake, et al., *Associations Between Circulating Sex Steroid Hormones and Cognition in Normal Elderly Women,* Neurology, Feb. 2000; 54(3): 599–603.

Tuiten, et al., *Time Course of Effects of Testosterone Administration on Sexual Arousal in Women,* Arch Gen Psychiatry, Feb. 2000; 57(2): 149–53.

Gonzalez–Sagrado, et al., *Reference Values and Methods Comparison of a New Testosterone Assay on the AxSYM System,* Clin Biochem, Apr. 2000; 33(3): 175–9.

Floter, et al., *Administration of Testosterone Undecanoate in Postmenopausal Women: Effects on Androgens, Estradiol, and Gonadotrophins.,* Menopause, Jul.–Aug. 2000; 7(4): 251–6.

Javanbakht, et al., *Pharmacokinetics of a Novel Testosterone Matrix Transdermal System in Healthy, Premenopausal Women and Women Infected with the Human Immunodeficiency Virus,* J Clin Endocrinol Metab, Jul. 2000; 85(7): 2395–401.

Shifren, et al., *Transdermal Testosterone Treatment in Women with Impaired Sexual Function After Oophorectomy.* The New England Journal of Medicine, Sep. 7, 2000, vol. 343, No. 10, 682–688.

*Sex, Hormones, and Hysterectomies,* The New England Journal of Medicine, Sep. 7, 2000—vol. 343, No. 10, 730–731.

*ENDO 99: Testosterone Patch Effective for Diminished Sexual Function in Surgically Menopausal Women,* Doctor's Guide to the Internet, Jun. 15, 1999.

C. Wang, et al., *Sublingual Testosterone Replacement Improves Muscle Mass and Strength, Decreases Bone Resorption, and Increases Bone Formation Markers in Hypogonadal Men—A Clinical Research Center Study,* Journal of Clinical Endocrinology and Metabolism, vol. 81, No. 10, pp. 3654–3662 (1996).

C. Wang, et al., *Testosterone Replacement Therapy Improves Mood in Hypogonadal Men—A Clinical Research Center Study,* Journal of Clinical Endocrinology and Metabolism, vol. 81, No. 10, pp. 3578–3583 (1996).

Meikle, et al., *Pharmacokinetics and Metabolism of a Permeation–Enhanced Testosterone Transdermal System in Hypogonadal Men: Influence of Application Site—A Clinical Research Center Study,* Journal of Clinical Endocrinology and Metabolism, vol. 81, No. 5, pp. 1832–1840 (1996).

Bhasin, *Clinical Review 34—Androgen Treatment of Hypogonadal Men,* Journal of Clinical Endocrinology and Metabolism, vol. 74, No. 6, pp. 1221–1225 (1992).

Stuenkel, et al, *Sublingual Administration of Testosterone–Hydroxypropyl–β–Cyclodextrin Inclusion Complex Simulates Episodic Androgen Release in Hypogonadal Men,* Journal of Clinical Endocrinology and Metabolism, vol. 72, No. 5, pp. 1054–1059 (1991).

Handelsman, et al., *Pharmacokinetics and Pharmacodynamics of Testosterone Pellets in Man,* Journal of Clinical Endocrinology and Metabolism, vol. 70, No. 1., pp. 216–222 (1990).

Sherwin, et al., *The Role of Androgen in the Maintenance of Sexual Functioning in Oophorectomized Women,* Psycosomatic Medicine, 49: 397–409 (1987).

Kuhn, et al., *Traitement Androgenique Percutane des Hypogonadismes Masculins. Efficacite Comparee de la Testosterone et d la Dihydrotestosterone: Etude de 40 Observations,* Contraception–Fertilite–Sexualite, vol. 14, No. 11, pp 1031–1036 (1986).

Wang, et al., *Pharmacokinetics of Transdermal Testosterone Gel in Hypogonadal Men: Application of Gel at One Site Versus Four Sites: A General Clinical Research Center Study,* The Journal of Endocrinology and Metabolism, vol. 85, No. 3, pp 964–969 (2000).

Marin, et al., *Androgen Treatment of Middle–Aged, Obese Men: Effects on Metabolism, Muscle and Adipose Tissues,* Androgens, Muscle and Adipose Tissue in Men, vol. 1, No. 6, pp. 329–336 (1992).

Morley, et al., *Androgen Deficiency in Aging Men: Role of Testosterone Replacement Therapy,* J. Lab Clin Med, vol. 135, No. 5, pp. 370–370 (2000).

Jaffe, et al., *Effect of 5–Alpha–Reductase Inhibition on Sex–Hormone–Binding Globulin in Elderly Men,* Horm Res, 1994:41:215–217.

Sherwin, *Affective Changes with Estrogen and Androgen Replacement Therapy in Surgically Menopausal Women,* Journal of Affective Disorders, 14 (1988) 177–187.

Sherwin, *Estrogen and/or Androgen Replacement Therapy and Cognitive Functioning in Surgically Menopausal Women,* Psychoneuroendocrinology, vol. 13, No. 4, pp. 345–357 (1988).

Sherwin, *Sex Hormones and Psychological Functioning in Postmenopausal Women,* Experimental Gerontology, vol. 29, Nos. 3/4, pp. 423–430 (1994).

Need, et al., *Double–Blind Placebo–Controlled Trial of Treatment of Osteoporosis with the Anabolic Nandrolone Decanoate,* Osteoporosis Int (1993) Supl. 1: S218–222.

Raisz, et al., *Comparison of the Effects of Estrogen Alone and Estrogen Plus Androgen on Biochemical Markers of Bone Formation and Resorption in Postmenopausal Women,* Journal of Clinical Endocrinology and Metabolism, vol. 81, No. 1, pp. 37–43 (1996).

Cashdan, *Hormones, Sex and Status in Women,* Hormones and Behavior, 29, 354–366 (1995).

Morrison, et al, *Androgens in the Elderly: Will Androgen Replacement Therapy Improve Mood, Cognition, and Quality of Life in Aging Men and Women,* Psychopharmacology Bulletin, 33(2):293–296 (1997).

Gruber, et al., *Effect of Percutaneous Androgen Replacement Therapy on Body Composition and Body Weight in Postmenopausal Women,* Maturitas 29 (1998) 253–259.

Buckler, et al. *The Effects of Low–Dose Testosterone Treatment on Lipid Metabolism, Clotting Factors and Ultrasonographic Ovarian Morphology in Women,* Clinical Endocrinology (1997) 49, 173–178.

Douchi, et al., *Serum Androgen Levels and Muscle Mass in Women with Polycysitc Ovary Syndrome,* Obstetrics & Gynecology, vol. 94, No. 3, pp. 337–340 (1999).

Davidson, et al., *Hormonal Changes and Sexual Function in Aging Men,* Journal of Clinical Endocrinology and Metabolism, vol. 57, No. 1, pp. 71–77 (1983).

Klugo, et al., *Response of Micropenis to Topical Testosterone and Gonadotropin,*, The Journal of Urology, vol. 119, May, pp. 667–668. (1978).

Basson, et al., *Androgen Replacement for Women,* Canadian Family Physician, vol. 45: Sep. 1999, pp. 2100–2107.

Persky, et al., *The Relation of Plasma Androgen Levels to Sexual Behaviors and Attitudes of Women,* Phychosomatic Medicine, vol. 44, No. 4 (Sep. 1982.

Carlstrom, et al., *Relationship Between Serum Testosterone and Sex Hormone–Binding Globulin in Adult Men with Intact or Absent Gonadal Function,* International Journal of Andrology, 1990, 13, pp. 67–73.

Moller, et al., *Sex Hormone–Binding Globulin Mediates Prostate Androgen Receptor Action via a Novel Signaling Pathway,* Endocrinolgy, Jan. 1998; 139(1):213–8.

Mantzoros, et al., *Serum Steroids in Relation to Benign Prostatic Hyperplasia,* Oncology, Nov.–Dec. 1997; 54(6):497–501.

Nakhla, et al., *Stimulation of Prostate Cancer Growth by Androgens and Estrogens Through the Intermediacy of Sex Hormone–Binding Globulin,* Endocrinology, Oct. 1996; 137(10): 4126–9.

Gann, et al., *Prospective Study of Sex Hormone Levels and Risk of Prostate Cancer,* J Natl Cancer Inst, Aug. 21, 1996; 88(16): 1118–26.

Liao, *Androgen Action: Molecular Mechanism and Medical Application,* J Formos Med Assoc, Sep. 1994; 93(9): 741–51.

Shirai, et al., *Effects of Testosterone, Dihydrotestosterone and Estrogen on 3,2'–Dimethyl–4–Aminobiphenyl–Induced Rat Prostate Carcinogenesis,* Int J Cancer, Apr. 15, 1994; 57(2):224–8.

Isaacs, *Etiology of Benign Prostatic Hyperplasia,* Eur Urol, 1994; 25 Suppl 1:6–9.

Denis, *Future Implications for the Management of Benign Prostatic Hyperplasia,* Eur Urol, 1994; 25 Suppl 1:29–34.

Nevalainen, et al., *Hormone Regulation of Human Prostate in Organ Culture,* Cancer Res, Nov. 1, 1993; 53(21:5199–207.

Alivizatos, et al., *Update of Hormonal Treatment in Cancer of the Prostate,* Anticancer Drugs, Jun. 1993; 4(3):301–9.

Geller, *Basis for Hormonal Management of Advanced Prostate Cancer,* Cancer, Feb. 1, 1993; 71(3 Suppl): 1039–45.

Geller, *Nonsurgical Treatment of Prostatic Hyperplasia,* Cancer, Jul. 1, 1992; 70(1 Suppl): 339–45.

Geller, *Pathogenesis and Medical Treatment of Benign Prostatic Hyperplasia,* Prostate Suppl, 1989; 2:95–104.

Isaacs, et al., *Etiology and Disease Process of Benign Prostatic Hyperplasia,* Prostate Suppl, 1989; 2:33–50.

Bruun, et al., *Dihydrotestosterone Measured in Core Biopsies from Prostatic Tissues,* Am J Clin Oncol, 1988; 11 Suppl 2:S27–9.

Petrangeli, et al., *Effects of Two Different Medical Treatments on Dihydrotestosterone Content and Androgen Receptors in Human Benign Prostatic Hyperplasia,* J Steroid Biochem, 1988; 30(1–6): 395–9.

Voigt, et al., *The Role of Tissue Steroids in Benign Hyperplasia and Prostate Cancer,* Urologe [A], Nov. 1987; 26(6):349–57.

Pollard, et al., *Dihydrotestosterone Does Not Induce Prostate Adenocarcinoma in L–W Rats,* Prostate, 1987; 10(4):325–31.

Petrow, *The Dihydrotestosterone (DHT) Hypothesis of Prostate Cancer and its Therapeutic Implications,* Prostate, 1986; 9(4): 343–61.

Geller, et al., *DHT in Prostate Cancer Tissue—a Guide to Management and Therapy,* Prostate, 1985; 6(1):19–25.

Drafta, et al., *The Effects of Endocrine Therapy on Plasma Steroids in Prostatic Carcinoma Patients,* Endocrinolgie, Jul.–Sep. 1984; 22(3): 191–7.

Karr, et al., *Induction of Benign Prostatic Hypertrophy in Baboons,* Urology, Mar. 1984; 23(3): 276–89.

Ewing, et al., *Dihydrotestosterone Concentration of Beagle Prostatic Tissue: Effect of Age and Hyperplasia,* Endocrinology, Dec. 1983; 113(6): 2004–9.

Stahl, et al., *Effects of Tamoxifen on the Levels of Luteinizing Hormone (LH), Follicle Stimulating Hormone (FSH), Prolactin (PRL), 17 beta–oestradiol (E2), Total and Free Testosterone (T) and Total and Free Dihydrotestosterone (DHT) in blood of Patients with Benign Prostatic Hyperplasia,* Exp Clin Endocrinol, Jul. 1983; 82(1): 21–8.

Meikle, et al., *Familial Prostatic Cancer Risk and Low Testosterone,* J Clin Endocrinol Metab, Jun. 1982; 54(6): 1104–8.

Wilson, *The Pathogenesis of Benign Prostatic Hyperplasia,* Am J Med, May 1980; 68(5): 745–56.

Sidh, et al., *Adenocarcinoma of Prostate: Role of 17beta–Estradiol and 5alpha–Dihydrotestosterone Binding Proteins,* Urology, Jun. 1979; 13(6): 597–603.

Bartsch, et al., *Sex Hormone Binding Globulin Binding Capacity, Testosterone, 5alpha–Dihydrotestosterone, Oestradiol and Prolactin in Plasma of Patients with Prostatic Carcinoma under Various Types of Hormonal Treatment,* Acta Endoctrinol (Copenh), Jul. 1977; 85(3): 650–64.

Arver, et al., *Improvement of Sexual Function in Testosterone Deficient Men Treated for 1 Year with a Permeation Enhanced Testosterone Transdermal System,* J Urol, May 1996; 155(5): 1604–8.

Gooren, *A Ten–Year Safety Study of the Oral Androgen Testosterone Undecanoate,* May–Jun. 1994; 15(3):212–5.

Mermall, et al., *Temporal (Circadian) and Functional Relationship between Pro Specific Antigen and Testosterone in Healthy Men,* Urology, Jul. 1995; 46(1): 45–53.

Vijayakumar, et al., *Results of a Study to Correlate Serum Prostate Specific antigen Reproductive Hormone Levels in Patients with Localized Protate Cancer,* J Natl Med Assoc, Nov. 1995; 87(11): 813–9.

Berner, et al., *Pharmacokinetic Charactierisation of Transdermal Delivery System,* Clin Pharmacokinet, Feb. 1994; 26(2): 121–34.

Behre, et al., *Prostate Volume in Testosterone–Treated and Untreated Hypogonadal Men in Comparison to Age–Matched Normal Controls,* Clin Endocrinol (OXF), Mar. 1994; 40(3): 341–9.

Akimoto, et al., *Relationship Between Diurnal Rhythm of Serum Testosterone and Prostatic Markers (PSA and PAP) in Untreated Prostate Cancer,* Urology, Mar. 1994; 43(3): 337–41.

Bhasin, et al., *A Biodegradable Testosterone Microcapsule Forumlation Providing Uniform Eugonadal Levels of Testosterone for 10–11 Weeks in Hypogonadal Men,* J Clin Endocrinol Metab, Jan. 1992; 74(1): 75–83.

Place, et al., *Transdermal Delivery of Testosterone with Testoderm to Provide Normal Circadian Pattern of Testosterone,* Ann NY Acad Sci, 1991; 618:441–9.

Conway, et al., *Randomized Clinical trial of Testosterone Replacement Therapy in Hypogonadal Men,* Int J Androl, Aug. 1988; 11(4): 247–64.

Tenover, et al., *Age–Related Alterations in the Circadian Rhythms of Pulsatile Luteinizing Hormone and Testosterone Secretion in Healthy Men,* J Gerontol, Nov. 1988; 43(6): M163–9.

Cunningham, et al., *Testosterone Replacement with Transdermal Therapeutic System, Physiological Serum Testosterone and Elevated Dihydrotestosterone Levels,* JAMA, May 5, 1989; 261(17): 2525–30.

Plymate, et al., *Circadian Variation in Testosterone, Sex Hormone–Binding Globulin and Calculated Non–Sex Hormone–Binding Globulin Bound Testosterone in Healthy Young and Elderly Men,* J Androl, Sep.–Oct. 1989; 10(5): 366–71.

Meikle, et al., *Prostate Size in Hypogonadal Men Treated with Nonscrotal Permeation–Enhanced Testosterone Transdermal System,* Urology, Feb. 1997; 49(2): 191–6.

Kuhn, et al., *Effects of 10 Days Administration of Percutaneous Dihydrotestosterone on the Pituitary–Testicular Axis in Normal Men,* J Clin Endocrinol Metab, Feb. 1984; 58(2): 231–5.

Bals–Pratsch, et al., *Transdermal Testosterone Substitution Therapy for Male Hypogonadism,* Lancet, Oct. 25, 1986; 2(8513): 943–6.

Ahmed, et al., *Transdermal Testosterone Therapy in the Treatment of Male Hypogonadism,* J Clin Endocrinol Metab, Mar. 1988; 66(3): 546–51.

Nilas, et al., *Bone Mass and its Relationship to Age and the Menopause,* J Clin Endocrinol Metab, Oct. 1987; 64(4): 697–702.

Chakravarti, et al., *Endocrine Changes and Sympotmatology After Oophorectomy in Premenopausal Women,* Br J Obstet Gynaecol, Oct. 1977; 84(10): 769–75.

Persky, et al., *Plasma Testosterone Level and Sexual Behavior of Couples,* Arch Sex Behav, May 1978; 7(3): 157–73.

Schreiner–Engel, et al., *Sexual Arousability and the Menstrual Cycle,* Psychosom Med Jun. 1981; 43(3): 199–214.

Alexander, et al., *Sex Steroids, Sexual Behavior, and Selection Attention for Erotic Stimuli in Women Using Oral Contraceptives,* Psychoneuroendocrinology, 1993; 18(2): 91–102.

Leiblum, et al., *Vaginal Atrophy in the Postmenopausal Woman. The Important Sexual Activity and Hormones,* JAMA, Apr. 22–29, 1983;249(16): 2195–8.

Bancroft, et al., *Mood, Sexuality, Hormones, and the Menstrual Cycle. III. Sexual. and the Role of Androgens.,* Psychosom Med, Dec. 1983; 45(6): 509–16.

Burger, et al., *The Management of Persistent Menopausal Symptoms with Oestradiol–Testosterone Implants: Clinical, Lipid and Hormonal Results,* Maturitas, Dec. 1984; 6(4): 351–8.

Sherwin, et al., *Androgen Enhances Sexual Motivation in Females: a Prospective Crossover Study of Sex Steroid Administration in the Surgical Menopause,* Psychosom Med, Jul.–Aug. 1985; 47(4): 339–51.

McCoy, et al., *A Longitudinal Study of the Effects of Menopause on Sexuality,* Maturitas, Sep. 1985; 7(3): 203–10.

Morris, et al., *Marital Sex Frequency and Midcycle Female Testosterone,* Arch Sex Behav, Feb. 1987; 16(1):27–37.

Sherwin, et al., *Postmenopausal Estrogen and Androgen Replacement and Lipoprotein Lipid Concentrations,* Am J Obstet Gynecol, Feb. 1987; 156(2): 414–9.

Burger, et al., *Effect of Combined Implants of Oestradiol and Testosterone on in Postmenopausal Women,* Br Med J (Clin Res Ed), Apr. 11, 1987; 294–(6577): 936–7.

Mazer, *New Clinical Applications of Transdermal Testosterone Delivery in Men and Women,* J Controlled Release, Mar. 1, 2000; 65(1–2): 303–15.

Dobs, *Pharmacokinetics, Efficacy, and Safety of a Permeation–Enhanced Testosterone Transdermal System in Comparison with Bi–Weekly Injections of Testosterone Enanthate for the Treatment of Hypogonadal Men,* J Clin Endocrinol Metab, Oct. 1999; 84(10): 3469–78.

*Testosterone Gel May Help Men with Low Sex Drive,* The Medical Letter on Drugs and Therapeutics, vol. 42 (Issue 1080), pp. 49–52 (Jun. 12, 2000).

Masi, *Sex Hormones and Rheumatoid Arthritis: Cause or Effect Relationships in a Complex Pathophysiology?,* Clin Exp Rheumatol, Mar.–Apr. 1995; 13(2): 227–40.

Davis, et al., *Testosterone Enhances Estradiol's Effects on Postmenopausal Bone Density and Sexuality*, Maturitas, Apr. 1995; 21(3): 227–36.

Schreiner–Engel, et al., *Low Sexual Desire in Women: the Role of Reproductive Hormones*, Horm Behav, Jun. 1989; 23(2): 221–34.

Kirschner, et al., *Androgen–Estrogen Metabolism in Women with Upper Body Versus Lower Body Obesity*, J Clin Endocrinol Metab, Feb. 1990; 70(2): 473–9.

Alexander, et al., *Testosterone and Sexual Behavior in Oral Contraceptive Users and Nonusers: a Prospective Study*, Horm Behav, Sep. 1990; 24(3): 388–402.

Studd, et al., *The Relationship Between Plasma Estradiol and the Increase in Density in Postmenopausal Women After Treatment with Subcutaneous Hormone Implants*, Am J Obstet Gynecol, Nov. 1990; 163(5 Pt 1): 1474–9.

Myers, et al., *Effects of Estrogen, Androgen, and Progestin on Sexual Psychophysiology and Behavior in Postmenopausal Women*, J Clin Endocrinol Metab, Apr. 1990; 70(4): 1124–31.

Gouchie, et al., *The Relationship Between Testosterone Levels and Cognitive Ability Patterns*, Psychoneuroendocrinology, 1991; 16(4): 323–34.

Garnett, et al., *A Cross–Sectional Study of the Effects of Long–Term Percutaneous Hormone Replacement Therapy on Bone Density*, Obstet Gynecol, Dec. 1991; 78(6): 1002–7.

Eriksson, et al., *Serum Levels of Androgens are Higher in Women with Premenstrual Irritability and Dysphoria than in Controls*, Psychoneuroendocrinology, May–Jul. 1992; 17(2–3): 195–204.

Garnett, et al., *The Effects of Plasma Estradiol Levels on Increases in Vertebral Femoral Bone Density Following Therapy with Estradiol and Estradiol with Testosterone Implants*, Obstet Gynecol, Jun. 1992; 79(6): 968–72.

Savvas, et all, *Increase in Bone Mass after One Year of Percutaneous Oestradiol Testosterone Implants in Post–Menopausal Women Who Have Prevoiusly Received Long–Term Oral Oestrogens*, Br J Obstet Gynaecol, Sep. 1992; 99(9): 757–60.

Kuhn, et al., Gynecomastia: Effect of Prolonged Treatment with Dihydrotestosterone by the Percutaneous Route, Presse Med, Jan. 8, 1983; 12(1): 21–5.

Itoh, et al., *The Assessment of Bioavailable Androgen Levels from the Serum Free Testosterone Level*, Nippon Naibunpi Gakkai Zasshi, Jan. 20, 1991; 67(1): 23–22.

Gaidano, et al., *Dynamics of the Binding Capacity of Plasma Sex Hormone Binding Globulin (SHBG) for Testosterone and Dihydrotestosterone During Puberty*, Clin Chim Acta, Jan. 15, 1980; 100(2): 91–97.

Zmuda, et al., *Exercise Increases Serum Testoterone and Sex Hormone–Binding Globulin Levels in Order Men*, Metabolism, Aug. 1996; 45(8): 935–939.

Wang, et al., *Salivary Testosterone in Men: Further Evidence of a Direct Correlation with Free Serum Testosterone*, J Clin Endocrinol Metab, Nov. 1981; 53(5): 1021–1024.

Fahrner, et al., *Effects of Endurance Exercise on Free Testosterone Concentration and the Binding Affinity of Sex Hormone Binding Globulin (SHBG)*, Int J Sports Med, Jan. 1998; 19(1): 12–15.

Masters, et al., *Investigation of Sex–Hormone Binding Globulin Interference in Direct Radioimmunoassays for Testosterone and Estradiol*, Clin Chem, Jun. 1989; 35(6): 979–984.

Pirke, et al., *Age Related Changes and Interrelationships Between Plasma Testosterone, Oestradiol and Testosterone–Binding Globulin in Normal Adult Males;* Acta Endocrinol (Copenh), Dec. 1973; 74(4): 792–800.

Lewis, et al., *Proceedings: Age–Related Changes in Serum 5alpha–dihydrotestosterone and Testosterone in Normal Men;* J Endocrinol, Nov. 1975; 67(2): 15P.

Belgorosky, et al., *Dynamics of SHBG Response to Testosterone. Implications Upon the Immediate Biological Effect of Sex Hormones*, J Steroid Biochem, Jun. 1983; 18(6): 783–787.

Longcope, et al., *Androgens, Estrogens, and Sex Hormone–Binding Globulin in Middle–Aged Men;* J Clin Endocrinol Metab, Dec. 1990; 71(6): 1442–1446.

Willemse, et al., *No Change in Plasma Free Testosterone Ratio and Plasma Sex Hormone–Binding Globulin Concentration During hCG Stimulation;* J Clin Endocrinol Metab, Jun. 1984; 58(6): 1193–1196.

Valero–Politi, et al., *Annual Rhythmic Variations of Follitropin, Lutropin, Testosterone and Sex–Hormone–Binding Globulin in Men*, Clin Chim Acta, Mar. 9, 1998; 271(1): 57–71.

Valero–Politi, et al., *Daily Rhythmic and Non–Rhythmic Variations of Follitropin, Lutropin, Testosterone, and Sex–Hormone–Binding Globulin in Men*, Eur J Clin Chem Clin Biochem, Jun. 1996; 34(6): 455–462.

Kasper, et al., *Development, Progression, and Androgen–Dependence of Prostate Tumors in Probasin–Large T Antigen Transgenic Mice: a Model for Prostate Cancer*, Lab Invest, Mar. 1998; 78(3): 319–333.

Boots, et al., *Measurement of Total Serum Testosterone Levels Using Commercially Available Kits: High Degree of Between–Kit Variability*, Fertil Steril, Feb. 1988; 69(2): 286–292.

Belgorosky, et al., *Progressive Decrease in Serum Sex Hormone–Binding Globulin from Infancy to Late Prepuberty in Boys*, J Clin Endocrinol Metab, Aug. 1986; 63(2): 510–512.

Holownia, et al., *A Clinical Evaluation of a Direct Radioimmunoassay of Testosterone;* Clin Chim Acta, Jan. 31, 1993; 214(1): 31–43.

Boyle, et al., *Serum Testosterone Measurements*, Am J Clin Pathol, Jun. 1984; 81(6): 754,761.

Leinonen, et al., *Serum Sex Hormone Binding Globulin and Testosterone Binding After Estradiol Administration, Castration, and Their Combination in Men with Prostatic Carcinoma*, Invest Urol, Jul. 1979; 17(1): 24–27.

Winters, et al., *Serum LH Concentrations in Hypogonadal Men During Transdermal Testosterone Replacement Through Scrotal Skin: Further Evidence that Ageing Enhances Testosterone Negative Feedback. The Testoderm Study Group*, Clin Endocrinol (Oxf) Sep. 1997; 47(3): 317–322.

Meikle, et al., *Enhanced Transdermal Delivery of Testosterone Across Nonscrotal Skin Produces Physiological Concentrations of Testosterone and Its Metabolites in Hypogonadal Men*, J Clin Endocrinol Metab, Mar. 1992; 74(3): 623–628.

Winters, *The Gonadotropin–Suppressive Activity of Androgen is Increased in Elderly Men;* Metabolism, Nov. 1984; 33(11): 1052–1059.

Tenover, et al., *The Effects of Aging in Normal Men on Bioavailable Testosterone and Luteinizing Hormone Secretion: Response to Clomiphene Citrate,* J Clin Endocrinol Metab, Dec. 1987; 65(6): 1118–1126.

Nankin, et al., *Decreased Bioavailable Testosterone in Aging Normal and Impotent Men,* J Clin Endocrinol Metab, Dec. 1986; 63(6):1418–11420.

Schaison, et al., *On the Role of Dihydrotestosterone in Regulating Luteinizing Hormone Secretion in Man,* J Clin Endocrinol Metab, Nov. 1980; 51(5): 1133–1137.

Mitchell, et al., *Age Related Changes in the Pituitary–Testicular Axis in Normal Men; Lower Serum Testosterone Results from Decreased Bioactive LH Drive,* Clin Endocrinol (Oxf), May 1995; 42(5): 501–507.

Korenman, et al., *Androgen Therapy of Hypogonadal Men with Transscrotal Testosterone Systems,* Am J Med, Sep. 1987; 83(3): 471–478.

Zeginiadou, et al., *NonLinear Binding of Sex Steroids to Albumin and Sex Hormone Binding Globulin,* Eur J Drug Metab Pharmacokinet, Jul. 1997; 22(3): 229–235.

Mendel, *Rates of Dissociation of Sex Steroid Hormones from Human Sex Hormone–Binding Globulin: a Reassessment,* J Steroid Biochem Mol Biol, Oct. 1990; 37(2): 251–255.

Iqbal, et al., *Binding of Testosterone and Oestradiol to Sex Hormone Binding Globulin, Human Serum Albumin and Other Plasma Proteins: Evidence for Non–Specific Binding of Oestradiol to Sex Hormone Binding Globulin,* Clin Sci, Mar. 1983; 64(3): 307–314.

Mean, et al., *Study on the Binding of Dihydrotestosterone, Testosterone and Oestradiol Sex Hormone Binding Globulin,* Clin Chim Acta, Oct. 1, 1977; 80(1): 171–180.

Belgorosky, et al., *Changes in Serum Sex Hormone–Binding Globulin and in Serum Non–Sex Hormone–Binding Globulin–Bound Testosterone During Prepuberty in Boys,* J Steroid Biochem, 1987; 27(1–3): 291–295.

Shanbhag, et al., *The Temperature Dependence of the Binding of 5 Alpha–Dihydrotestosterone and Estradiol to the Sex Hormone Globulin (SHBG) of Human Plasma,* J Steroid Biochem, Feb. 1986; 24(2): 549–555.

Meikle, et al., *Familial Effects on Plasma Sex–Steroid Content in Man: Testosterone, Estradiol and Sex–Hormone–Binding Globulin,* Metabolism, Jan. 1982; 31(1): 6–9.

Bartsch, *Interrelationships Between Sex Hormone–Binding Globulin and Testosterone, 5 alpha–dihydrotestosterone and Oestradiol–17 beta in Blood of Normal Men,* Maturitas, Jul. 1980; 2(2): 109–118.

Signorello, et al., *Serum Steroids in Relation to Prostate Cancer Risk in a Case–Control Study (Greece),* Cancer Causes Control, Jul. 1997; 8(4): 632–636.

Plymate, et al., *Effects of Sex Hormone Binding Globulin (SHBG) on Human Prostatic Carcinoma,* J Steroid Biochem Mol Biol, 1991; 40(4–6): 833–839.

Bartsch, et al., *Interrelationships Between Sex Hormone–Binding Globulin and 17 beta–Estradiol, Testosterone, 5 alpha–Dihydrotestosterone, Thyroxine, and Triiodothyronine in Prepubertal and Pubertal Girls,* J Clin Endocrinol Metab, Jun. 1980; 50(6): 1053–1056.

Schottner, et al., *Lignans Interering with 5 alph–Dihydrotestosterone Binding to Human Sex Hormone–Binding Globulin,* J Natl Prod, Jan. 1988; 61(1): 119–121.

Bocchinfuso, et al., *Expression and Differential Glycosylation of Human Sex Hormone–Binding Globulin by Mammalian Cell Lines,* Mol Endocrinol, Nov. 1991; 5(11): 1723–1729.

Tsai, et al., *Metabolic Approaches to Enhance Transdermal Drug Delivery. 1. Effect of Lipid Synthesis Inhibitors,* J Pharm Sci, Jun. 1996; 85(6): 643–648.

Man, et al., *Optimization of Physiological Lipid Mixtures for Barrier Repair,* J Invest Dermatol, May 1996; 106(5): 1096–1101.

Labrie, et al., *Physiological Changes in Dehydroepiandrosterone are not Reflected by Serum Levels of Active Androgens and Estrogens but of their Metabolites: Intracrinology,* J Clin Endocrinol Metab, Aug. 1997; 82(8): 2403–2409.

Grinspoon, et al, *Body Composition and Endocrine Function in Women with Acquired Immunodeficiency Syndrome Wasting,* J. Clin Endocrinol Metab, May 1997; 82(5): 1332–7.

Navarro, et al., *Salivary Testosterone in Postmenopausal Women with Rheumatoid Arthritis,* J Rheumatol, Jun. 1998; 25(6): 1059–62.

Bloch, et al. *Pituitary–Adrenal Hormones and Testosterone Across the Menstrual Cycle in Women with Premenstrual Syndrome and Controls,* Biol Psychiatry, Jun. 15, 1998; 43(12): 897–903.

Khosla, et al., *Relationship of Serum Sex Steroid Levels and Bone Turnover with Bone Mineral density in Men and Women: A Key Role for Bioavailable Estrogen,* J Clin Endocrinol Metab, Jul. 1998; 83(7): 2266–74.

Padova, et al., *Pubarche Induction with Testosterone Treatment in Women with Panhypopituitarism,* Fertil Steril, Feb. 1996; 65(2): 437–9.

Tutten, et al., *Discrepancies Between Genital Responses and Subjective Sexual Function during Testosterone Substitution in Women with Hypothalamic Amenorrhea,* Psychosom Med, May–Jun. 1996; 58(3): 234–41.

Casson, et al., *Androgen Replacement Therapy in Women: Myths and Realities,* Int J Fertil Menopausal Stud; Jul.–Aug. 1996; 41(4):412–22.

Davis, et al., *Clinical Review 82: Androgens and the Postmenopausal Woman,* J. Clin Endocrinol Metab, Aug. 1996; 81(8): 2759–63.

Booji, et al., *Androgens as Adjuvant Treatment in Postmenopausal Female Patients with Rheumatoid Arthritis,* Ann Rheum Dis, Nov. 1996; 55(11): 811–5.

Bancroft, et al., *Androgens and the Menopause; a Study of 40–60–Year–Old Women,* Clin Endocrinol (Oxf), Nov. 1996; 45(5): 577–87.

Davis, et al., *Use of Androgens in Postmenopausal Women,* Curr Opin Obstet Gynecol, Jun. 1997; 9(3): 177–80.

Rouru, et al., *Serum Leptin Concentrations in Women with Polycystic Ovary Syndrome,* J Clin Endocrinol Metab, Jun. 1997; 82(6): 1697–700.

Mantzoros, et al., *Leptin Concentrations in the Polycystic Ovary Syndrome,* J Clin Endocrinol Metab, Jun. 1997; 82(6): 1687–91.

Krahe, et al., *Risk Factors for Decreased Bone Density in Premenopausal Women,* Braz J Med Biol Res, Sep. 1997; 30(9): 1061–6.

Greendale, et al., *Endogenous Sex Steroids and Bone Mineral Density in Older Women and Men: the Rancho Bernardo Study,* J Bone Miner Res, Nov. 1997; 12(11): 1833–43.

Goggin, et al., *The Relationship of Mood, Endocrine, and Sexual Disorders in Human Immunodeficiency Virus Positive (HIV+) Women: an Exploratory Study,* Psychosom Med, Jan.–Feb. 1998; 60(1): 11–6.

Zamberlan, et al., *Effect of Hyperandrogenism and Menstrual Cycle Abnormalities Bone Mass and Bone Turnover in Young Women,* Clin Endocrinol (Oxf), Feb. 1998; 48(2): 169–73.

Sinha–Hikim, et al., *The Use of a Sensitive Equilibrium Dialysis Method for the Measurement of Free Testosterone Levels in Healthy, Cycling Women and in Human Immunodeficiency Virus–Infected Women;* J Clin Endocrinol Metab, Apr. 1998; 83(4): 1312–8.

Heikkila, et al., *Serum Androgen–Anabolic Hormones and the Risk of Rheumatoid Arthritis,* Ann Rheum Dis, May 1998; 57(5): 281–5.

Watts, et al. *Comparison of Oral Estrogens and Estrogens Plus Androgen on Mineral Density, Menopausal Symptoms, and Lipid–Lipoprotein Profiles in Surgical Menopause,* Obstet Gynecol, Apr. 1995; 85(4):529–37.

Heiss, et al., *Associations of Body Fat Distribution, Circulating Sex Hormones Bone Density in Postmenopausal Women,* J Clin Endocrinol Metab, May 1995; 80(5): 1591–6.

Pedersen, et al., *Relationship Between Sex Hormones, Body Composition and Metabolic Risk Parameters in Premenopausal Women,* Eur J Endocrinol, Aug. 1995; 133(2): 200–6.

Van Gaal, et al., *Sex Hormones, Body Fat Distribution, Resting Metabolic Rate and Glucose–Induced Thermogenesis in Premenopausal Obese Women,* Int J Obes Relat Metab Disord, May 1994; 18(5): 333–.

Sands, et al., *Exogenous Androgens in Postmenopausal Women,* Am J Med, Jan. 16, 1995; 98(1A): 76S–79S.

Bernini, et al., *Endogenous Androgens and Carotid Intimal–Medical Thickness in Women,* J Clin Endocrinol Metab, Jun. 1999; 84(6): 2008–12.

van Honk, et al., *Correlations Among Salivary Testosterone, Mood, and Selective Attention to Threat in Humans,* Horm Behav, Aug. 1999; 36(1): 17–24.

Good, et al., *Bone Mineral Density and Body Composition in Lean Women with Polycystic Ovary Syndrome,* Fertil Steril, Jul. 1999; 72(1): 21–5.

Buckler, et al., *Which Androgen Replacement Therapy for Women?,* J Clin Endocrinol Metab, Nov. 1998; 83(11):3920–4.

Cutolo, et al., *Hypothalamic–Pituitary–Adrenocortical Axis Function in Premenopausal Women with Rheumatoid Arthritis Not Treated with Glucocorticoids,* J Rheumatol, Feb. 1999; 26(2): 282–8.

Baumgartner, et al., *Predictors of Skeletal Muscle Mass in Elderly Men and Women,* Mech Ageing Dev, Mar. 1, 1999; 107(2): 123–36.

Exton, et al., *Cardiovascular and Endocrine Alternations after Masturbation–Induced Orgasm in Women,* Psychosom Med, May–Jun. 1999; 61(3): 280–9.

Davis, *Androgen Replacement in Women: a Commentary,* J Clin Endocrinol Metab, Jun. 1999; 84(6): 1886–91.

Rako, *Testosterone Deficiency: a Key Factor in the Increased Cardiovascular RIsk to Women Following Hysterectomy or with Natural Aging?* J Womens Health, Sep. 1998; 7(7): 825–9.

ABCNews.com: *Testosterone Patch Increases Women's Sex Drive,* http://abcnews.go.com/sections/living/DailyNews/testosterone990615.html.

Miller, et al., *Transdermal Testosterone Administration in Women with Acquired Immunodeficiency Syndrome Wasting: a Pilot Study,* J Clin Endocrinol Metab, Aug. 1998; 83(8): 2717–25.

Belgorosky, *Sex Hormone Binding Globulin Response to Testosterone. An Androgen Sensitivity Test,* Acta Endocrinol (Copenh), May 1985; 109(1): 130–138.

Choi, et al., *Transdermal Dihydrotestosterone Therapy and its Effects on Patients with Microphallus,* J Urol, Aug. 1993; 150(2 Pt 2): 657–660.

Ernesti, et al., *Absorption and Metabolism of Topically Applied Testosterone in an Organotypic Skin Culture,* Skin Pharmacol, 1992; 5(3): 146–153.

Findlay, et al., *Treatment of Primary Hypogonadism in Men by the Transdermal Administration of Testosterone,* J Clin Endocrinol Metab, Feb. 1989; 68(2): 369–373.

Kao, et al., *Skin Absorption and Cutaneous First Pass Metabolism of Topical Steroids: in vitro Studies with Mouse Skin in Organ Culture,* J Pharmacol Exp Ther, May 1987; 241(2): 482–487.

Wang, et al., *Pharmacokinetics of Transdermal Testosterone Gel in Hypogonadal Men,* Endo '98 Submission Program, 1998N Abstract Form.

*Androgel,* Information Release, date unknown.

* cited by examiner

PHARMACEUTICAL COMPOSITION AND METHOD FOR TREATING HYPOGONADISM

FIELD OF THE INVENTION

The present invention is directed to a pharmaceutical composition comprising testosterone in a gel formulation, and to methods of using the same.

BACKGROUND OF THE INVENTION

A. Testosterone Metabolism in Men

Testosterone is the major circulating androgen in men. More than 95% of the 6–7 mg of testosterone produced per day is secreted by the approximately 500 million Leydig cells in the testes. Two hormones produced by the pituitary gland, luteinizing hormone ("LH") and follicle stimulating hormone ("FSH"), are required for the development and maintenance of testicular function.

The most important hormone for the regulation of Leydig cell number and function is LH. In eugonadal men, LH secretion from the pituitary is inhibited through a negative-feedback pathway by increased concentrations of testosterone through the inhibition of the release of gonadotropin-releasing hormone ("GRH") by the hypothalamus. FSH promotes spermatogenesis and is essential for the normal maturation of sperm. FSH secretion from the pituitary normally is inhibited through a negative-feedback pathway by increased testosterone concentrations.

Testosterone is responsible primarily for the development and maintenance of secondary sex characteristics in men. In the body, circulating testosterone is metabolized to various 17-keto steroids through two different pathways. Testosterone can be metabolized to dihydrotestosterone ("DHT") by the enzyme 5α-reductase. There are two forms of 5α-reductase in the body: one form is found predominately in the liver and non-genital skin while another form is found in the urogenital tract of the male and the genital skin of both sexes. Testosterone can also be metabolized to estradiol ("$E_2$") by an aromatase enzyme complex found in the liver, fat, and the testes.

Testosterone circulates in the blood 98% bound to protein. In men, approximately 40% of the binding is to the high-affinity sex hormone binding globulin ("SHBG"). The remaining 60% is bound weakly to albumin. Thus, a number of measurements for testosterone are available from clinical laboratories. The term "free" testosterone as used herein refers to the fraction of testosterone in the blood that is not bound to protein. The term "total testosterone" or "testosterone" as used herein means the free testosterone plus protein-bound testosterone. The term "bioavailable testosterone" as used herein refers to the non-SHBG bound testosterone and includes testosterone weakly bound to albumin.

The conversion of testosterone to DHT is important in many respects. For example, DHT binds with greater affinity to SHBG than does testosterone. In addition, in many tissues, the activity of testosterone depends on the reduction to DHT, which binds to cytosol receptor proteins. The steroid-receptor complex is then transported to the nucleus where it initiates transcription and cellular changes related to androgen action. DHT is also thought to lower prostate volume and inhibit tumor development in the prostate. Thus, given the importance of DHT and testosterone in normal body functioning, researchers frequently assess and report androgen concentrations in patients as total androgen ("DHT+T") or as a ratio of DHT to testosterone ("DHT/T ratio").

The following table from the UCLA-Harbor Medical Center summarizes the hormone concentrations in normal adult men range:

TABLE 1

| Hormone Levels in Normal Men | |
|---|---|
| Hormone | Normal Range |
| Testosterone | 298 to 1043 ng/dL |
| Free testosterone | 3.5 to 17.9 ng/dL |
| DHT | 31 to 193 ng/dL |
| DHT/T Ratio | 0.052 to 0.33 |
| DHT + T | 372 to 1349 ng/dL |
| SHBG | 10.8 to 46.6 nmol/L |
| FSH | 1.0 to 6.9 mIU/mL |
| LH | 1.0 to 8.1 mIU/mL |
| $E_2$ | 17.1 to 46.1 pg/mL |

There is considerable variation in the half-life of testosterone reported in the literature, ranging from 10 to 100 minutes. Researchers do agree, however, that circulating testosterone has a diurnal variation in normal young men. Maximum levels occur at approximately 6:00 to 8:00 a.m. with levels declining throughout the day. Characteristic profiles have a maximum testosterone level of 720 ng/dL and a minimum level of 430 ng/dL. The physiological significance of this diurnal cycle, if any, however, is not clear.

B. Hypogonadal Men and Current Treatments for Hypogonadism

Male hypogonadism results from a variety of pathophysiological conditions in which testosterone concentration is diminished below the normal range. The hypogonadic condition is sometimes linked with a number of physiological changes, such as diminished interest in sex, impotence, reduced lean body mass, decreased bone density, lowered mood, and energy levels.

Researchers generally classify hypogonadism into one of three types. Primary hypogonadism includes the testicular failure due to congenital or acquired anorchia, XYY Syndrome, XX males, Noonan's Syndrome, gonadal dysgenesis, Leydig cell tumors, maldescended testes, varicocele, Sertoli-Cell-Only Syndrome, cryptorchidism, bilateral torsion, vanishing testis syndrome, orchiectomy, Klinefelter's Syndrome, chemotherapy, toxic damage from alcohol or heavy metals, and general disease (renal failure, liver cirrhosis, diabetes, myotonia dystrophica). Patients with primary hypogonadism show an intact feedback mechanism in that the low serum testosterone concentrations are associated with high FSH and LH concentrations. However, because of testicular or other failures, the high LH concentrations are not effective at stimulating testosterone production.

Secondary hypogonadism involves an idiopathic gonadotropin or LH-releasing hormone deficiency. This type of hypogonadism includes Kallman's Syndrome, Prader-Labhart-Willi's Syndrome, Laurence-Moon-Biedl's Syndrome, pituitary insufficiency/adenomas, Pasqualini's Syndrome, hemochromatosis, hyperprolactinemia, or pituitary-hypothalamic injury from tumors, trauma, radiation, or obesity. Because patients with secondary hypogonadism do not demonstrate an intact feedback pathway, the lower testosterone concentrations are not associated with increased LH or FSH levels. Thus, these men have low testosterone serum levels but have gonadotropins in the normal to low range.

Third, hypogonadism may be age-related. Men experience a slow but continuous decline in average serum testosterone after approximately age 20 to 30 years. Researchers estimate that the decline is about 1–2% per year. Cross-sectional studies in men have found that the mean testosterone value at age 80 years is approximately 75%, of that at age 30 years. Because the serum concentration of SHBG increases as men age, the fall in bioavailable and free testosterone is even greater than the fall in total testosterone. Researchers have estimated that approximately 50% of healthy men between the ages of 50 and 70 have levels of bioavailable testosterone that are below the lower normal limit. Moreover, as men age, the circadian rhythm of testosterone concentration is often muted, dampened, or completely lost. The major problem with aging appears to be within the hypothalamic-pituitary unit. For example, researchers have found that with aging, LH levels do not increase despite the low testosterone levels. Regardless of the cause, these untreated testosterone deficiencies in older men may lead to a variety of physiological changes, including sexual dysfunction, decreased libido, loss of muscle mass, decreased bone density, depressed mood, and decreased cognitive function. The net result is geriatric hypogonadism, or what is commonly referred to as "male menopause."

Today, hypogonadism is the most common hormone deficiency in men, affecting 5 in every 1,000 men. At present, it is estimated that only five percent of the estimated four to five million American men of all ages with hypogonadism currently receive testosterone replacement therapy. Thus, for years, researchers have investigated methods of delivering testosterone to men. These methods include intramuscular injections (43%), oral replacement (24%), pellet implants (23%), and transdermal patches (10%). A summary of these methods is shown in Table 2.

TABLE 2

Mode of Application and Dosage of Various Testosterone Preparations

| Preparation | Route Of Application | Full Substitution Dose |
| --- | --- | --- |
| In Clinical Use | | |
| Testosterone enanthate | Intramuscular injection | 200–25.0 g every 2–3 weeks |
| Testosterone cypionate | Intramuscular injection | 200 mg every 2 weeks |
| Testosterone undecanoate | Oral | 2–4 capsules at 40 mg per day |
| Transdermal testosterone patch | Scrotal skin | 1 membrane per day |
| Transdermal testosterone patch | Non-scrotal skin | 1 or 2 systems per day |
| Testosterone implants | Implantation under the abdominal skin | 3–6 implants of 200 mg every 6 months |
| Under Development | | |
| Testosterone cyclodextrin | Sublingual | 2.5–5.0 mg twice daily |
| Testosterone undecanoate | Intramuscular injection | 1000 mg every 8–10 weeks |
| Testosterone buciclate | Intramuscular injection | 1000 mg every 12–16 weeks |
| Testosterone microspheres | Intramuscular injection | 315 mg for 11 weeks |
| Obsolete | | |
| 17α-Methyltestosterone | Oral | 25–5.0 g per day |
| Fluoxymesterone | Sublingual | 10–25 mg per day |
| | Oral | 10–20 mg per day |

As discussed below, all of the testosterone replacement methods currently employed suffer from one or more drawbacks, such as undesirable pharmacokinetic profiles or skin irritation. Thus, although the need for an effective testosterone replacement methodology has existed for decades, an alternative replacement therapy that overcomes these problems has never been developed. The present invention is directed to a 1% testosterone hydroalcoholic gel that overcomes the problems associated with current testosterone replacement methods.

1. Subdermal Pellet Implants

Subdermal implants have been used as a method of testosterone replacement since the 1940s. The implant is produced by melting crystalline testosterone into a cylindrical form. Today, pellet implants are manufactured to contain either 100 mg (length 6 mm, surface area 117 mm$^2$) or 200 mg of testosterone (length 12 mm, surface area 202 mm$^2$). Patients receive dosages ranging from 100 to 1,200 mg, depending on the individual's requirements. The implants are inserted subcutaneously either by using a trocar and cannula or by open surgery into an area where there is relatively little movement. Frequently, the implant is placed in the lower abdominal wall or the buttock. Insertion is made under local anesthesia, and the wound is closed with an adhesive dressing or a fine suture.

Implants have several major drawbacks. First, implants require a surgical procedure which many hypogonadal men simply do not wish to endure. Second, implant therapy includes a risk of extrusion (8.5%), bleeding (2.3%), or infection (0.6%). Scarring is also a risk. Perhaps most important, the pharmacokinetic profile of testosterone pellet implant therapy fails to provide men with a suitable consistent testosterone level. In general, subdermal testosterone implants produce supra-physiologically high serum testosterone levels which slowly decline so that before the next injection subnormally low levels of testosterone are reached. For example, in one recent pharmacokinetic study, hypogonadal patients who received six implants (1,200 mg testosterone) showed an initial short-lived burst release of testosterone within the first two days after application. A stable plateau was then maintained over then next two months (day 2: 1,015 ng/dL; day 63: 990 ng/dL). Thereafter, the testosterone levels declined to baseline by day 300. DHT serum concentrations also rose significantly above the baseline, peaking at about 63 days after implementation and greatly exceeding the upper limit of the normal range. From day 21 to day 189, the DHT/T ratio was significantly increased. The pharmacokinetic profiles for testosterone, DHT, and DHT/T in this study are shown in FIG. 1. See Jockenhovel et al., *Pharmacokinetics and Pharmacodynamics of Subcutaneous Testosterone Implants in Hypogonadal Men*, 45 CLINICAL ENDOCRINOLOGY 61–71 (1996). Other studies involving implants have reported similar undesirable pharmacokinetic profiles.

2. Injection of Testosterone Esters

Since the 1950s, researchers have experimented with the intermuscular depot injection of testosterone esters (such as enanthate, cypionate) to increase testosterone serum levels in hypogonadal men. More recent studies have involved injection of testosterone buciclate or testosterone undecanoate in an oil-based vehicle. Other researchers have injected testosterone microcapsule formulations.

Testosterone ester injection treatments suffer from many problems. Patients receiving injection therapy often complain that the delivery mechanism is painful and causes local skin reactions. In addition, testosterone microcapsule treatment requires two simultaneous intramuscular injections of a relatively large volume, which may be difficult to administer due to the high viscosity of the solution and the tendency to block the needle. Other men generally find testosterone injection therapy inconvenient because injection usually requires the patient to visit his physician every two to three weeks.

Equally important, injection-based testosterone replacement treatments still create an undesirable pharmacokinetic profile. The profile generally shows a supra-physiologic testosterone concentration during the first 24 to 48 hours followed by a gradual fall—often to sub-physiologic levels—over the next few weeks. These high serun testosterone levels, paralleled by increases in $E_2$ are also considered the reason for acne and gynecomastia occurring in some patients, and for polycythaemia, occasionally encountered especially in older patients using injectable testosterone esters. In the case of testosterone buciclate injections, the treatment barely provides normal androgen serum levels and the maximal increase of serum testosterone over baseline does not exceed 172 ng/dL (6 nmol/dL) on average. Because libido, potency, mood, and energy are thought to fluctuate with the serum testosterone level, testosterone injections have largely been unsuccessful in influencing these variables. Thus, testosterone injection remains an undesirable testosterone replacement treatment method.

3. Oral/Sublingual/Buccal Preparations of Androgens

In the 1970s, researchers began using oral, sublingual, or buccal preparations of androgens (such as fluoxyrnesterone, 17α-methyl-testosterone or testosterone undecanoate) as a means for testosterone replacement. More recently, researchers have experimented with the sublingual administration of testosterone-hydroxypropyl-beta-cyclodextrin inclusion complexes. Predictably, both fluoxymesterone and methyl testosterone are 17-alkylated and thus associated with liver toxicity. Because these substances must first pass through the liver, they also produce an unfavorable effect on serum lipid profile, increasing LDL and decreasing HDL, and carbohydrate metabolism. while testosterone undecanoate has preferential absorption through the intestinal lymphatics, it has not been approved in the United States.

The pharmacokinetic profiles for oral, sublingual, and buccal delivery mechanisms are also undesirable because patients are subjected to super-physiologic testosterone levels followed by a quick return to the baseline. For example, one recent testing of a buccal preparation showed that patients obtained a peak serum hormone levels within 30 minutes after administration, with a mean serum testosterone concentration of 2,688+/−147 ng/dL and a return to baseline in 4 to 6 hours. See Dobs et al., *Pharmacokinetic Characteristics, Efficacy and Safety of Buccal Testosterone in Hypogonadal Males: A Pilot Study*, 83 J. CLINICAL ENDOCRINOLOGY & METABOLISM 33–39 (1998). To date, the ability of these testosterone delivery mechanisms to alter physiological parameters (such as muscle mass, muscle strength, bone resorption, urinary calcium excretion, or bone formation) is inconclusive. Likewise, researchers have postulated that super-physiologic testosterone levels may not have any extra beneficial impact on mood parameters such as anger, nervousness, and irritability.

4. Testosterone Transdermal Patches

The most recent testosterone delivery systems have involved transdermal patches. Currently, there are three patches used in the market: TESTODERM®, TESTODERM® TTS, and ANDRODERM®.

a. TESTODERM®

TESTODERM® (Alza Pharmaceuticals, Mountain View, Calif.) was the first testosterone-containing patch developed. The TESTODERM® patch is currently available in two sizes (40 or 60 cm$^2$). The patch contains 10 or 15 mg of testosterone and delivers 4.0 mg or 6.0 mg of testosterone per day. TESTODERM® is placed on shaved scrotal skin, aided by application of heat for a few seconds from a hair dryer.

FIG. 2 shows a typical pharmacokinetic testosterone profile for both the 40 cm$^2$ and 60 cm$^2$ patch. Studies have also shown that after two to four weeks of continuous daily use, the average plasma concentration of DHT and DHT/T increased four to five times above normal. The high serum DHT levels are presumably caused by the increased metabolism of 5α-reductase in the scrotal skin.

Several problems are associated with the TESTODERM® patch. Not surprisingly, many men simply do not like the unpleasant experience of dry-shaving the scrotal hair for optimal contact. In addition, patients may not be able to wear close-fitting underwear when undergoing treatment. Men frequently experience dislodgment of the patch, usually with exercise or hot weather. In many instances, men experience itching and/or swelling in the scrotal area. Finally, in a number of patients, there is an inability to achieve adequate serum hormone levels.

b. TESTODERM® TTS

The most recently developed non-scrotal patch is TESTODERM® TTS (Alza Pharmaceuticals, Mountain View, Calif.). It is an occlusive patch applied once daily to the arm, back, or upper buttocks. The system is comprised of a flexible backing of transparent polyester/ethylene-vinyl acetate copolymer film, a drug reservoir of testosterone, and an ethylene-vinyl acetate copolymer membrane coated with a layer of polyisobutylene adhesive formulation. A protective liner of silicone-coated polyester covers the adhesive surface.

Upon application, serum testosterone concentrations rise to a maximum at two to four hours and return toward baseline within two hours after system removal. Many men, however, are unable to obtain and/or sustain testosterone levels within the normal range. The pharmacokinetic parameters for testosterone concentrations are shown as follows:

TABLE 3

TESTODERM ® TTS Testosterone Parameters

| Parameters | Day 1 | Day 5 |
|---|---|---|
| $C_{max}$ (ng/dL) | 482 ± 149 | 473 ± 148 |
| $T_{max}$ (h) | 3.9 | 3.0 |
| $C_{min}$ (ng/dL) | 164 ± 104 | 189 ± 86 |
| $T_{min}$ (h) | 0 | 0 |

The typical 24-hour steady state testosterone concentration achieved with TESTODERM® TTS patch is shown in FIG. 3.

Because of TESTODERM® patch is applied to the scrotal skin while the TESTODERM TTS® patch is applied to non-scrotal skin, the two patches provide different steady-state concentrations of the two major testosterone metabolites, DTH and $E_2$,:

TABLE 4

Hormone Levels Using TESTODERM ® and TESTODERM ® TTS

| Hormone | Placebo | TESTODERM ® | TESTODERM ® TTS |
|---|---|---|---|
| DHT (ng/dL) | 11 | 134 | 38 |
| $E_2$ (pg/ml) | 3.8 | 10 | 21.4 |

Likewise, in contrast to the scrotal patch, TESTODERM TTS® treatment creates a DHT/T ratio that is not different from that of a placebo treatment. Both systems, however, suffer from similar problems. In clinical studies, TESTODERM® TTS is associated with transient itching in 12% of patients, erythema in 3% of patients, and puritus in 2% of patients. Moreover, in one 14-day study, 42% of patients reported three or more detachments, 33% of which occurred during exercise.

c. ANDRODERM®

ANDRODERM® (Watson Laboratories, Inc., Corona, Calif.) is a testosterone-containing patch applied to non-scrotal skin. The circular patch has a total surface area of 37 cm$^2$. The patch consists of a liquid reservoir containing 12.2 mg of testosterone and a permeation-enhanced vehicle containing ethanol, water, monoglycerides, fatty acid esters, and gelling agents. The suggested dose of two patches, applied each night in a rotating manner on the back, abdomen, upper arm, or thigh, delivers 4.1 to 6.8 mg of testosterone.

The steady state pharmacokinetic profile of a clinical study involving ANDRODERM® is shown in FIG. 4. In general, upon repeated application of the ANDRODERM® patch, serum testosterone levels increase gradually for eight hours after each application and then remain at this plateau level for about another eight hours before declining.

In clinical trials, ANDRODERM® is associated with skin irritation in about a third of the patients, and 10% to 15% of subjects have been reported to discontinue the treatment because of chronic skin irritation. Preapplication of corticosteroid cream at the site of application of ANDRODERM® has been reported to decrease the incidence and severity of the skin irritation. A recent study, however, found that the incidence of skin reactions sufficiently noxious enough to interrupt therapy was as high as 52%. See Parker et al., *Experience with Transdermal Testosterone Replacement in Hypogonadal Men*, 50 CLINICAL ENDOCRINOLOGY (OXF) 57–62 (1999). The study reported:

> Two-thirds of respondents found the Andropatch unsatisfactory. Patches were variously described as noisy, visually indiscrete, embarrassing, unpleasant to apply and remove, and generally to be socially unacceptable. They fell off in swimming pools and showers, attracted ribald comments from sporting partners, and left bald red marks over trunk and limbs. Dogs, wives, and children were distracted by noise of the patches with body movements. Those with poor mobility or manual dexterity (and several were over 70 years of age) found it difficult to remove packaging an apply patches dorsally.

d. Transdermal Patch Summary

In sum, the transdermal patch generally offers an improved pharmacokinetic profile compared to other currently used testosterone delivery mechanisms. However, as discussed above, the clinical and survey data shows that all of these patches suffer from significant drawbacks, such as buritus, burn-like blisters, and erythema. Moreover, one recent study has concluded that the adverse effects associated with transdermal patch systems are "substantially higher" than reported in clinical trials. See Parker, supra. Thus, the transdermal patch still remains an inadequate testosterone replacement therapy alternative for most men.

5. DHT Gels

Researchers have recently begun investigating the application of DHT to the skin in a transdernal gel. However, the pharmacokinetics of a DHT-gel is markedly different from that of a testosterone gel. Application of DHT-gel results in decreased serum testosterone, $E_2$, LH, and FSH levels. Thus, DHT gels are not effective at increasing testosterone levels in hypogonadal men.

Accordingly, there is a definite need for a testosterone formulation that safely and effectively provides an optimal and predictable pharmacokinetic profile.

SUMMARY OF THE INVENTION

The foregoing problems are solved and a technical advance is achieved with the present invention. The present invention generally comprises a testosterone gel. Daily transdermal application of the gel in hypogonadal men results in a unique pharmacokinetic steady-state profile for testosterone. Long-term treatment further results in increased bone mineral density, enhanced libido, enhanced erectile frequency and satisfaction, increased positive mood, increased muscle strength, and improved body composition without significant skin irritation. The present invention is also directed to a unique method of administering the testosterone gel employing a packet having a polyethylene liner compatible with the components of the gel.

DESCRIPTION OF THE INVENTION

Figure 1:
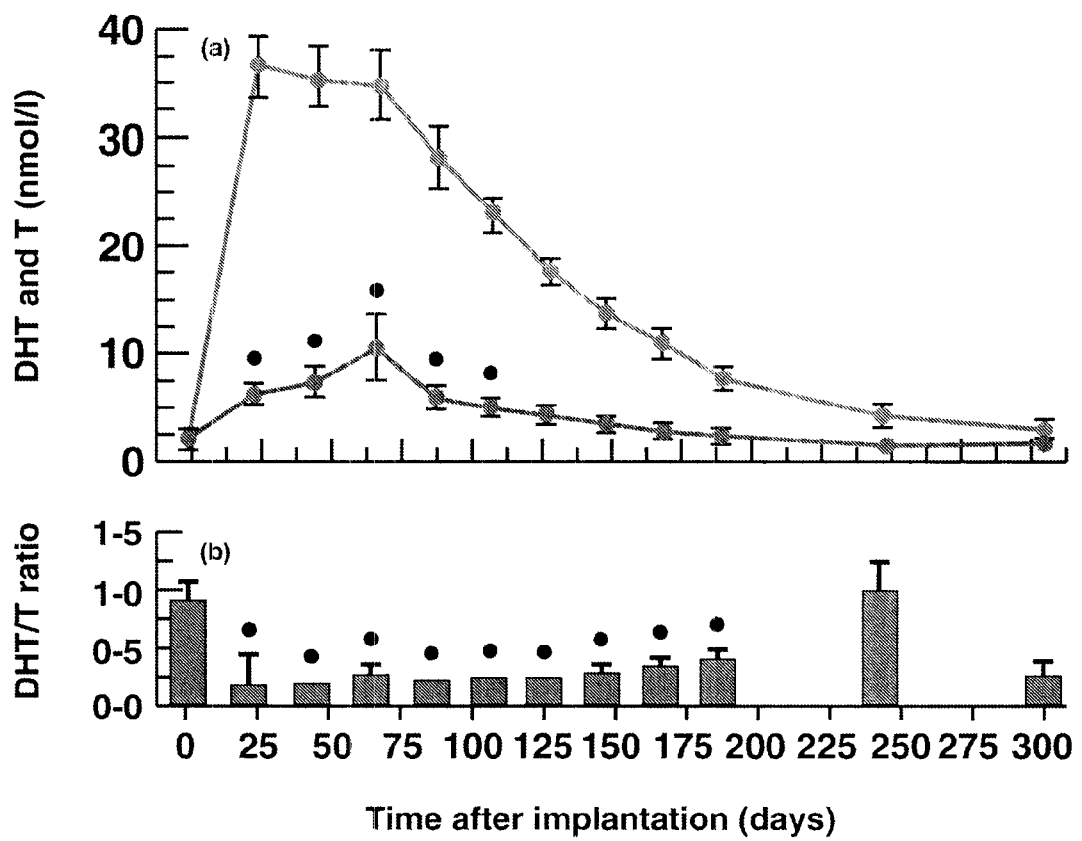
FIG. 1 is a graph of testosterone concentrations, DHT concentrations, and the DHT/T ratio for patients receiving a subdermal testosterone pellet implant over a period of 300 days after implantation.
Figure 2:
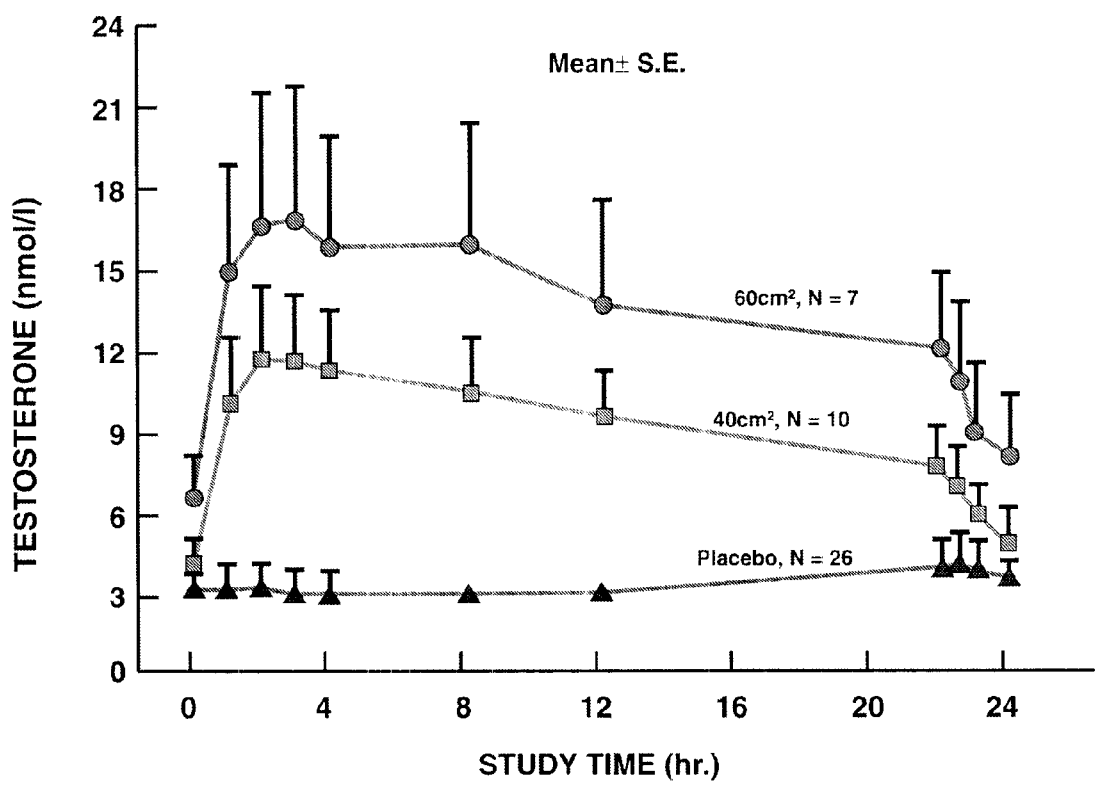
FIG. 2 is a 24-hour testosterone pharmacokinetic profile for patients receiving the 40 cm$^2$ or 60 cm$^2$ TESTODERM® patch.
Figure 3:
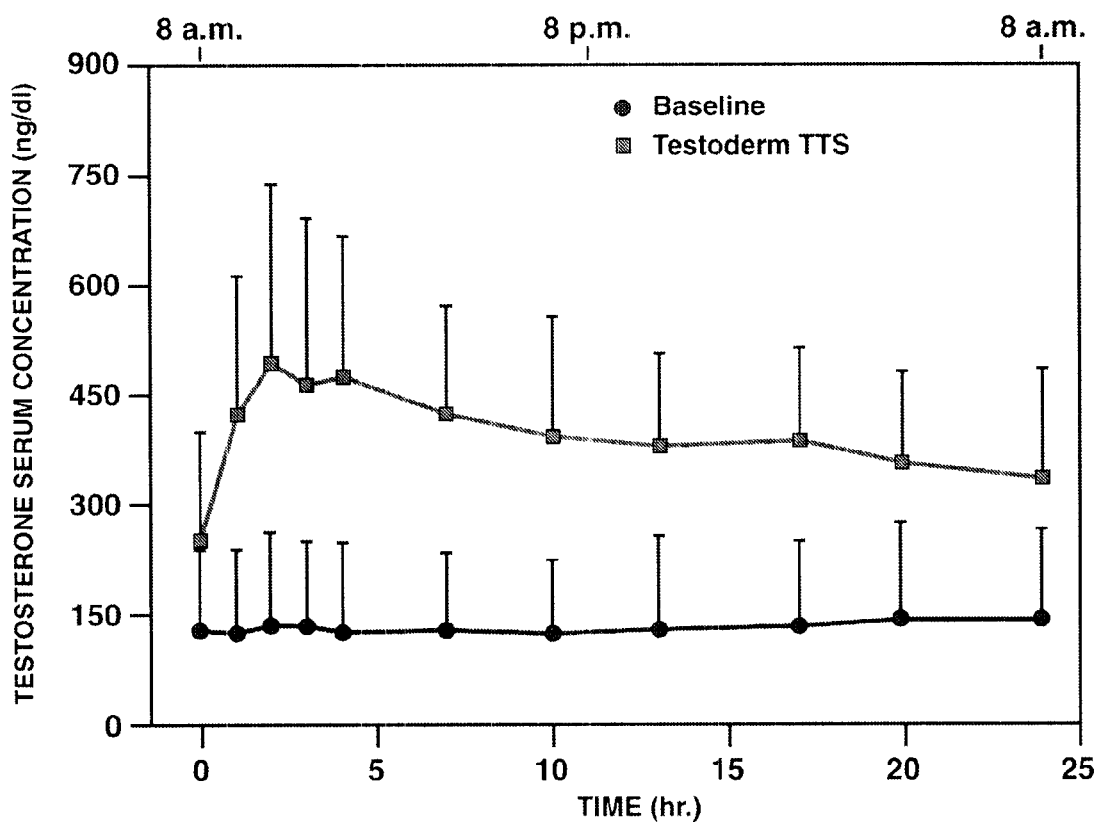
FIG. 3 is a 24-hour testosterone pharmacokinetic profile for patients receiving the TESTODERM® TTS patch.
Figure 4:
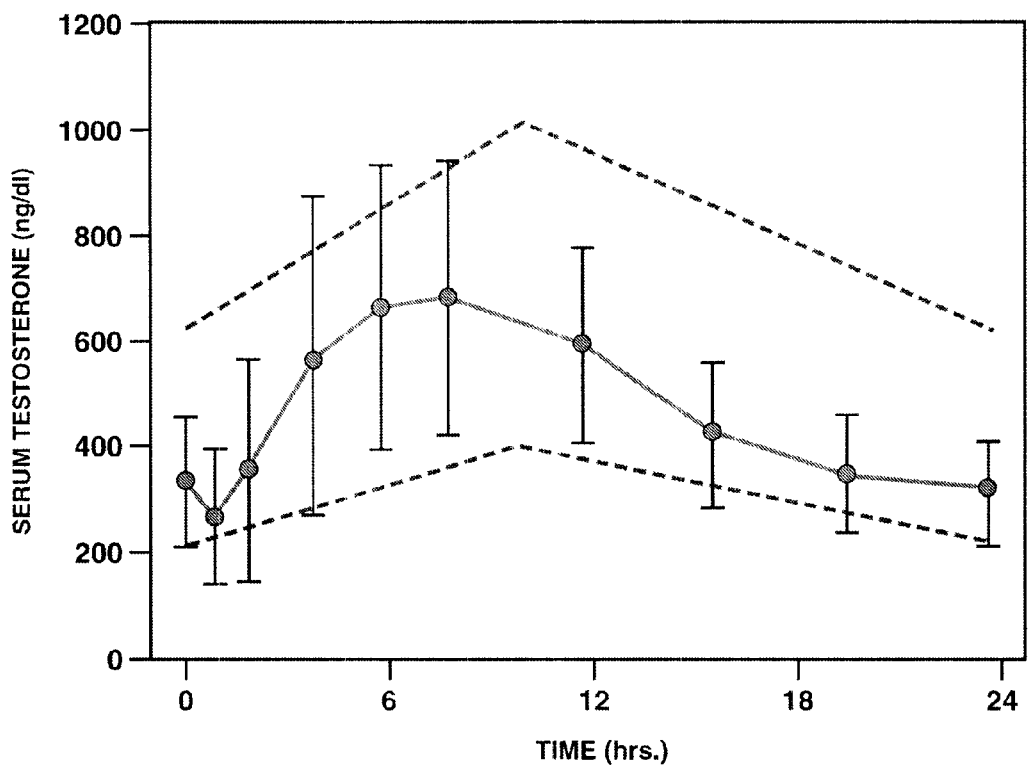
FIG. 4 is a 24-hour testosterone pharmacokinetic profile for patients receiving the ANDRODERM® patch.

While the present invention may be embodied in many different forms, several specific embodiments are discussed herein with the understanding that the present disclosure is to be considered only as an exemplification of the principles of the invention, and it is not intended to limit the invention to the embodiments illustrated.

The present invention is directed to a pharmaceutical composition for percutaneous administration comprising at least one active pharmaceutical ingredient (e.g., testosterone) in a hydroalcoholic gel. In a broad aspect of the invention, the active ingredients employed in the composition may include anabolic steroids such as androisoxazole, bolasterone, clostebol, ethylestrenol, formyldienolone, 4-hydroxy-19-nortestosterone, methenolone, methyltrienolone, nandrolone, okymesterone, quinbolone, stenbolone, trenbolone; androgenic steroids such as boldenone, fluoxymesterone, mestanolone, mesterolone, methandrostenolone, 17-methyltestosterone, 17α-methyltestosterone 3-cyclopentyl enol ether, norethandrolone, normethandrone, oxandrolone, oxymetholone, prasterone, stanlolone, stanozolol, dihydrotestosterone, testosterone; and progestogens such as anagestone, chlormadinone acetate, delmadinone acetate, demegestone, dimethisterone, dihydrogesterone, ethinylestrenol, ethisterone, ethynodiol, ethynodiol diacetate, flurogestone acetate, gestodene, gestonorone caproate, haloprogesterone, 17-hydroxy-16-methylene-progesterone, 17 β-hydroxyprogesterone, 17 α-hydroxyprogesterone caproate, medrogestone, medroxyprogesterone, megestrol acetate, melengestrol, norethindrone, norethindrone acetate, norethynodrel, norgesterone, norgestimate, norgestrel, norgestrienone, 19-norprogesterone, norvinisterone, pentagestrone, progesterone, promegestone, quingestrone, and trengestone; and all enantiomers, isomers and derivatives of these compounds. (Based upon the list provided in *The Merck Index*, Merck & Co. Rahway, N.J. (1998)).

In addition to the active ingredient, the gel comprises one or more lower alcohols, such as ethanol or isopropanol; a penetration enhancing agent; a thickener; and water. Additionally, the present invention may optionally include salts, emollients, stabilizers, antimicrobials, fragrances, and propellants.

A "penetration enhancer" is an agent known to accelerate the delivery of the drug through the skin. These agents also have been referred to as accelerants, adjuvants, and absorption promoters, and are collectively referred to herein as "enhancers." This class of agents includes those with diverse mechanisms of action including those which have the function of improving the solubility and diffusibility of the drug, and those which improve percutaneous absorption by changing the ability of the stratum corneum to retain moisture, softening the skin, improving the skin's permeability, acting as penetration assistants or hair-follicle openers or changing the state of the skin such as the boundary layer.

The penetration enhancer of the present invention is a functional derivative of a fatty acid, which includes isosteric modifications of fatty acids or non-acidic derivatives of the carboxylic functional group of a fatty acid or isosteric modifications thereof. In one embodiment, the functional derivative of a fatty acid is an unsaturated alkanoic acid in which the —COOH group is substituted with a functional derivative thereof, such as alcohols, polyols, amides and substituted derivatives thereof. The term "fatty acid" means a fatty acid that has four (4) to twenty-four (24) carbon atoms. Non-limiting examples of penetration enhancers include C8–C22 fatty acids such as isostearic acid, octanoic acid, and oleic acid; C8–C22 fatty alcohols such as oleyl alcohol and lauryl alcohol; lower alkyl esters of C8–C22 fatty acids such as ethyl oleate, isopropyl myristate, butyl stearate, and methyl laurate; di(lower)alkyl esters of C6–C8 diacids such as diisopropyl adipate; monoglycerides of C8–C22 fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes.

The thickeners used herein may include anionic polymers such as polyacrylic acid (CARBOPOL® by B.F. Goodrich Specialty Polymers and Chemicals Division of Cleveland, Ohio), carboxymethylcellulose and the like. Additional thickeners, enhancers and adjuvants may generally be found in *United States Pharmacopeia/National Formulary* (2000); *Remington's The Science and Practice of Pharmacy*, Meade Publishing Co.

The amount of drug to be incorporated in the composition varies depending on the particular drug, the desired therapeutic effect, and the time span for which the gel is to provide a therapeutic effect. The composition is used in a "pharmacologically effective amount." This means that the concentration of the drug is such that in the composition it results in a therapeutic level of drug delivered over the term that the gel is to be used. Such delivery is dependent on a number of variables including the drug, the form of drug, the time period for which the individual dosage unit is to be used, the flux rate of the drug from the gel, surface area of application site, etc. The amount of drug necessary can be experimentally determined based on the flux rate of the drug through the gel, and through the skin when used with and without enhancers.

One such testosterone gel has only recently been made available in the United States under the trademark AndroGel® by Unimed Pharmaceuticals, Inc., Deerfield, Ill., one of the assignees of this application. In one embodiment, the gel is comprised of the following substances in approximate amounts:

TABLE 5

Composition of AndroGel ®

| SUBSTANCE | AMOUNT (w/w) PER 100 g OF GEL |
|---|---|
| Testosterone | 1.0 g |
| Carbopol 980 | 0.90 g |
| Isopropyl myristate | 0.50 g |
| 0.1 N NaOH | 4.72 g |
| Ethanol (95% w/w) | 72.5 g* |
| Purified water (qsf) | 100 g |

*corresponding to 67 g of ethanol.

One skilled in the art will appreciate that the constituents of this formulation may be varied in amounts yet continue to be within the spirit and scope of the present invention. For example, the composition may contain about 0.1 to about 10.0 g of testosterone, about 0.1 to about 5.0 g Carbopol, about 0.1 to about 5.0 g isopropyl myristate, and about 30.0 to about 98.0 g ethanol.

A therapeutically effective amount of the gel is rubbed onto a given area of skin by the user. The combination of the lipophilic testosterone with the hydroalcoholic gel helps drive the testosterone in to the outer layers of the skin where it is absorbed and then slowly released into the blood stream. As demonstrated by the data presented herein, the administration of the gel of the present invention has a sustained effect.

Toxicity and therapeutic efficacy of the active ingredients can be determined by standard pharmaceutical procedures, e.g., for determining $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The term "treatment" as used herein refers to any treatment of a human condition or disease and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

Although the examples of the present invention involve the treatment of disorders associated with hypogonadal men, the composition and method of the present invention may be used to treat these disorders in humans and animals of any kind, such as dogs, pigs, sheep, horses, cows, cats, zoo animals, and other commercially bred farm animals.

The present invention is further illustrated by the following examples, which should not be construed as limiting in any way. The contents of all cited references throughout this application are hereby expressly incorporated by reference. The practice of the present invention will employ, unless otherwise indicated, conventional techniques of pharmacology and pharmaceutics, which are within the skill of the art.

EXAMPLES

Example 1

Treatment of Hypogonadism in Male Subjects

One embodiment of the present invention involves the transdermal application of AndroGel® as a method of treating male hypogonadism. As demonstrated below, application of the gel results in a unique pharmacokinetic profile for testosterone, as well as concomitant modulation of several other sex hormones. Application of the testosterone gel to hypogonadal male subjects also results in: (1) increased bone mineral density, (2) enhanced libido, (3) enhanced erectile capability and satisfaction, (4) increased positive mood, (5) increased muscle strength, and (6) better body composition, such increased total body lean mass and decreased total body fat mass. Moreover, the gel is not associated with significant skin irritation.

Methods

In this example, hypogonadal men were recruited and studied in 16 centers in the United States. The patients were between 19 and 68 years and had single morning serum testosterone levels at screening of less than or equal to 300 ng/dL (10.4 nmol/L). A total of 227 patients were enrolled: 73, 78, and 76 were randomized to receive 5.0 g/day of AndroGel® (delivering 50 mg/day of testosterone to the skin of which about 10% or 5 mg is absorbed), 10.0 g/day of AndroGel® (delivering 100 mg/day of testosterone to the skin of which about 10% or 10 mg is absorbed), or the ANDRODERM® testosterone patch ("T patch") (delivering 50 mg/day of testosterone), respectively.

As shown in the following table, there were no significant group-associated differences of the patients' characteristics at baseline.

TABLE 6

Baseline Characteristics of the Hypogonadal Men

| Treatment Group | T patch | AndroGel ® (5.0 g/day) | AndroGel ® (10.0 g/day) |
|---|---|---|---|
| No of subjects enrolled | 76 | 73 | 78 |
| Age (years) | 51.1 | 51.3 | 51.0 |
| Range (years) | 28–67 | 23–67 | 19–68 |
| Height (cm) | 179.3 ± 0.9 | 175.8 ± 0.8 | 178.6 ± 0.8 |
| Weight (kg) | 92.7 ± 1.6 | 90.5 ± 1.8 | 91.6 ± 1.5 |
| Serum testosterone (nmol/L) | 6.40 ± 0.41 | 6.44 ± 0.39 | 6.49 ± 0.37 |

TABLE 6-continued

Baseline Characteristics of the Hypogonadal Men

| Treatment Group | T patch | AndroGel ® (5.0 g/day) | AndroGel ® (10.0 g/day) |
|---|---|---|---|
| Causes of hypogonadism | | | |
| Primary hypogonadism | 34 | 26 | 34 |
| Klinefelter's Syndrome | 9 | 5 | 8 |
| Post Orchidectomy/Anorchia | 2 | 1 | 3 |
| Primary Testicular Failure | 23 | 20 | 23 |
| Secondary hypogonadism | 15 | 17 | 12 |
| Kallman's Syndrome | 2 | 2 | 0 |
| Hypothalimic Pituitary Disorder | 6 | 6 | 3 |
| Pituitary Tumor | 7 | 9 | 9 |
| Aging | 6 | 13 | 6 |
| Not classified | 21 | 17 | 26 |
| Years diagnosed | 5.8 +1.1 | 4.4 ± 0.9 | 5.7 ± 1.24 |
| Number previously treated with testosterone | 50 (65.8%) | 38 (52.1%) | 46 (59.0%) |
| Type of Previous Hormonal Treatment | | | |
| Intramuscular injections | 26 | 20 | 28 |
| Transdermal patch | 12 | 7 | 8 |
| All others | 12 | 11 | 10 |
| Duration of treatment (years) | 5.8 ± 1.0 | 5.4 ± 0.8 | 4.6 ± 80.7 |

Forty-one percent (93/227) of the subjects had not received prior testosterone replacement therapy. Previously treated hypogonadal men were withdrawn from testosterone ester injection for at least six weeks and oral or transdermal androgens for four weeks before the screening visit. Aside from the hypogonadism, the subjects were in good health as evidenced by medical history, physical examination, complete blood count, urinalysis, and serum biochemistry. If the subjects were on lipid-lowering agents or tranquilizers, the doses were stabilized for at least three months prior to enrollment. Less than 5% of the subjects were taking supplemental calcium or vitamin D during the study. The subjects had no history of chronic medical illness, alcohol or drug abuse. They had a normal rectal examination, a PSA level of less than 4 ng/mL, and a urine. flow rate of 12 mL/s or greater. Patients were excluded if they had a generalized skin disease that might affect the testosterone absorption or prior history of skin irritability with ANDRODERM® patch. Subjects weighing less than 80% or over 140% of their ideal body weight were also excluded.

The randomized, multi-center, parallel study compared two doses of AndroGel® with the ANDRODERM® testosterone patch. The study was double-blind with respect to the AndroGel® dose and open-labeled for the testosterone patch group. For the first three months of the study (days 1 to 90), the subjects were randomized to receive 5.0 g/day of AndroGel®, 10.0 g/day of AndroGel®, or two non-scrotal patches. In the following three months (days 91 to 180), the subjects were administered one of the following treatments: 5.0 g/day of AndroGel®, 10.0 g/day of AndroGel®, 7.5 g/day of AndroGel®, or two non-scrotal patches. Patients who were applying AndroGel® had a single, pre-application serum testosterone measured on day 60 and, if the levels were within the normal range of 300 to 1,000 ng/dL (10.4 to 34.7 nmol/L), then they remained on their original dose. Patients with testosterone levels less than 300 ng/dL and who were originally assigned to apply 5.0 g/day of Andro-Gel® and those with testosterone levels more than 1,000 ng/dL who had received. 10.0 g/day of AndroGel® were then reassigned to administer 7.5 g/day of AndroGel® for days 91 to 180.

Accordingly, at 90 days, dose adjustments were made in the AndroGel® groups based on the pre-application serum testosterone levels on day 60. Twenty subjects in the 5.0 g/day AndroGel® group had the dose increased to 7.5 g/day. Twenty patients in the 10.0 g/day AndroGel® group had the AndroGel® dose reduced to 7.5 g/day. There were three patients in the testosterone patch group who were switched to 5.0 g/day AndroGel® because of patch intolerance. One 10.0 g/day AndroGel® subject was adjusted to receive 5.0 g/day and one 5.0 g/day AndroGel® subject had the dose adjusted to 2.5 g/day. The number of subjects enrolled into day 91 to 180 of the study thus consisted of 51 receiving 5.0 g/day of AndroGel®, 40 receiving 7.5 g/day of AndroGel®, 52 receiving 10.0 g/day of AndroGel®, and 52 continuing on the ANDRODERM® patch. The treatment groups in this example may thus be characterized in two ways, either by "initial" or by the "final" treatment group.

Subjects returned to the study center on days 0, 30, 60, 90, 120, 150, and 180 for a clinical examination, skin irritation and adverse event assessments. Fasting blood samples for calcium, inorganic phosphorus, parathyroid hormone ("PTH"), osteocalcin, type I procollagen, and skeletal specific alkaline phosphatase ("SALP") were collected on days 0, 30, 90, 120, and 180. In addition, a fasting two-hour timed urine collection for urine creatinine, calcium, and type 1 collagen cross-linked N-telopeptides ("N-telopeptide") were collected on days 0, 30, 90, 120, and 180. Other tests performed were as follows:

(1) Hematology: hemoglobin, hematocrit, red blood cell count, platelets, white blood cell counts with differential analysis (neutrophils, lymphocytes, monocytes, eosinophils, and basophils);

(2) Chemistry: alkaline phosphatase, alanine aminotransferase, serum glutamic pyruvic transaminase ("ALT/SGPT"), asparate aminotransferase/serum glutamin axaloacetic transaminase ("AST/SGOT"), total bilirubin, creatinine, glucose, and elecrolytes (sodium, potassium, choride, bicarbonate, calcium, and inorganic phosphorus);

(3) Lipids: total cholesterol, high-density lipoprotein ("HDL"), low-density lipoprotein ("LDL"), and triglycerides;

(4) Urinalysis: color, appearance, specific gravity, pH, protein, glucose, ketones, blood, bilirubin, and nitrites; and (5) Other: PSA (screening days 90–180), prolactin (screening), and testosterone (screening) including electrolytes, glucose, renal, and liver function tests and lipid profile, were performed at all clinic visits. Bone mineral density ("BMD") was analyzed at day 0 and day 180.

A. AndroGel® and ANDRODERM® patch

Approximately 250 g of AndroGel® was packaged in multidose glass bottles that delivered 2.25 g of the gel for each actuation of the pump. Patients assigned to apply 5.0 g/day of AndroGel® testosterone were given one bottle of AndroGel® and one bottle of placebo gel (containing vehicle but no testosterone), while those assigned to receive 10.0 g/day of AndroGel® were dispensed two bottles of the active AndroGel®. The patients were then instructed to apply the bottle contents to the right and left upper arms/ shoulders and to the right and left sides of the abdomen on an alternate basis. For example, on the first day of the study, patients applied two actuations from one bottle, one each to the left and right upper arm/shoulder, and two actuations from the second bottle, one each to the left and right abdomen. On the following day of treatment, the applications were reversed. Alternate application sites continued throughout the study. After application of the gel to the skin, the gel dried within a few minutes. Patients washed their hands thoroughly with soap and water immediately after gel application.

The 7.5 g/day AndroGel® group received their dose in an open-label fashion. After 90 days, for the subjects titrated to the AndroGel® 7.5 g/day dose, the patients were supplied with three bottles, one containing placebo and the other two AndroGel®. The subjects were instructed to apply one actuation from the placebo bottle and three actuations from a AndroGel® bottle to four different sites of the body as above. The sites were rotated each day taking the same sequence as described above.

ANDRODERM® testosterone patches each delivering 2.5 mg/day of testosterone were provided to about one-third of the patients in the study. These patients were instructed to apply two testosterone patches to a clean, dry area of skin on the back, abdomen, upper arms, or thighs once per day. Application sites were rotated with approximately seven days interval between applications to the same site.

On study days when the patients were evaluated, the gel/patches were applied following pre-dose evaluations. On the remaining days, the testosterone gel or patches were applied at approximately 8:00 a.m. for 180 days.

B. Study Method and Results

1. Hormone Pharmacokinetics

On days 0, 1, 30, 90, and 180, the patients had multiple blood samples for testosterone and free testosterone measurements at 30, 15 and 0 minutes before and 2, 4, 8, 12, 16, and 24 hours after AndroGel® or patch application. In addition, subjects returned on days 60, 120, and 150 for a single blood sampling prior to application of the gel or patch. Serum DHT, $E_2$, FSH, LH and SHBG were measured on samples collected before gel application on days 0, 30, 60, 90, 120, 150, and 180. Sera for all hormones were stored frozen at −20° C. until assay. All samples for a patient for each hormone were measured in the same assay whenever possible. The hormone assays were then measured at the Endocrine Research Laboratory of the UCLA-Harbor Medical Center.

The following table summarizes the pharmacokinetic parameters were measured for each patient:

TABLE 7

| | Pharmacokinetic Parameters |
|---|---|
| $AUC_{0-24}$ | area under the curve from 0 to 24 hours, determined using the linear trapezoidal rule. |
| $C_{base}$ or $C_o$ | Baseline concentration |
| $C_{avg}$ | time-averaged concentration over the 24-hour dosing interval determined by $AUC_{0-24}/24$ |
| $C_{max}$ | maximum concentration during the 24-hour dosing interval |
| $C_{min}$ | minimum concentration during the 24-hour dosing interval |
| $T_{max}$ | time at which $C_{max}$ occurred |
| $T_{min}$ | time at which $C_{min}$ occurred |
| Fluctuation Index | extent of variation in the serum concentration over the course of a single day, calculated as $(C_{max}-C_{min})/C_{avg}$ |

TABLE 7-continued

| | Pharmacokinetic Parameters |
|---|---|
| Accumulation ratio | increase in the daily drug exposure with continued dosing, calculated as the ratio of the AUC at steady on a particular day over the AUC on day 1 (e.g., $AUC_{day\ 30}/AUC_{day\ 1}$) |
| Net $AUC_{0-24}$ | $AUC_{0-24}$ on days 30, 90, 180 − $AUC_{0-24}$ on day 0 | a. Testosterone Pharmacokinetics (1) Methods

Serum testosterone levels were measured after extraction with ethylacetate and hexane by a specific radioimmunoassay ("RIA") using reagents from ICN (Costa Mesa, Calif.). The cross reactivities of the antiserum used in the testosterone RIA were 2.0% for DHT, 2.3% for androstenedione, 0.8% for 3-β-androstanediol, 0.6% for etiocholanolone and less than 0.01% for all other steroids tested. The lower limit of quantitation ("LLQ") for serum testosterone measured by this assay was 25 ng/dL (0.87 nmol/L). The mean accuracy of the testosterone assay, determined by spiking steroid free serum with varying amounts of testosterone (0.9 nmol/L to 52 nmol/L), was 104% and ranged from 92% to 117%. The intra-assay and interassay coefficients of the testosterone assay were 7.3 and 11.1%, respectively, at the normal adult male range. In normal adult men, testosterone concentrations range from 298 to 1,043 ng/dL (10.33 to 36.17 nmol/L) as determined at the UCLA-Harbor Medical Center.

(2) Baseline Concentration

Figure 5A:
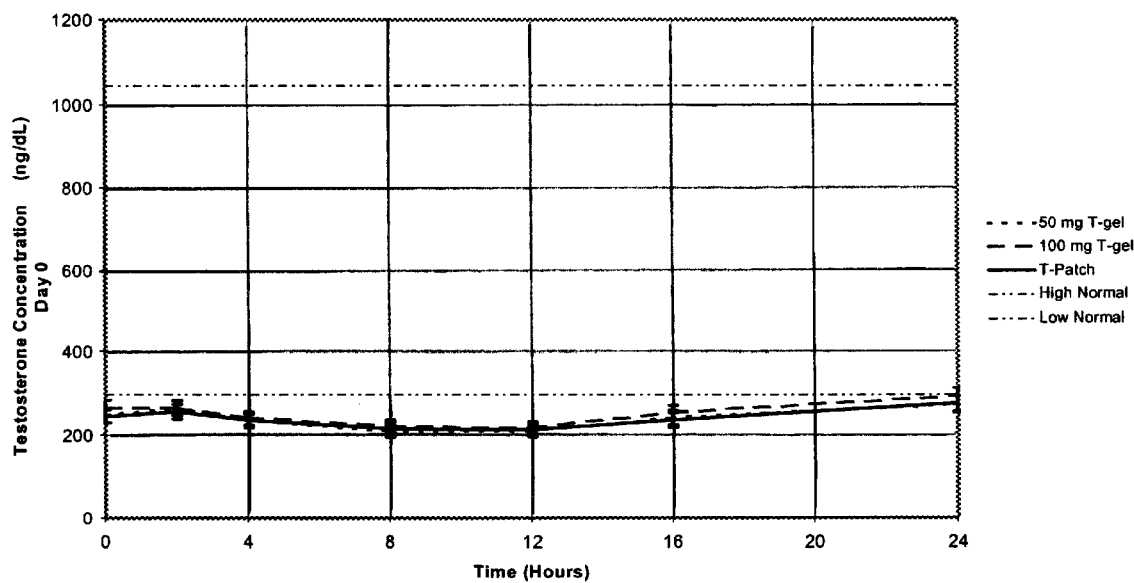
FIG. 5(a) is a graph showing the 24-hour testosterone pharmacokinetic profile for hypogonadal men prior to receiving 5.0 g/day of AndroGel®, 10.0 g/day of AndroGel®, or the testosterone patch (by initial treatment group).

As shown in Table 8 and FIG. 5(a), at baseline, the average serum testosterone concentrations over 24 hours ($C_{avg}$) were similar in the groups and below the adult normal range. Moreover the variations of the serum concentration (based on maximum and minimum concentrations during the 24-hour period, $C_{max}$ and $C_{min}$, respectively) during the day were also similar in the three groups. FIG. 5(a) shows that the mean testosterone levels had a maximum level between 8 to 10 a.m. (i.e., at 0 to 2 hours) and the minimum 8 to 12 hours later, demonstrating a mild diurnal variation of serum testosterone. About one-third of the patients in each group had $C_{avg}$ within the lower normal adult male range on day 0 (24/73 for the 5.0 g/day AndroGel® group, 26/78 for the 10.0 g/day AndroGel® group, and 25/76 for testosterone patch group). All except three of the subjects met the enrollment criterion of serum testosterone less than 300 ng/dL (10.4 nmol/L) on admission.

TABLE 8(a)

Baseline Phamacokinetic Parameters
by Initial Treatment Group (Mean ± SD)

| | 5.0 g/day T-Gel | 10.0 g/day T-gel | T-patch |
|---|---|---|---|
| N | 73 | 78 | 76 |
| $C_{avg}$ (ng/dL) | 237 ± 130 | 248 ± 140 | 237 ± 139 |
| $C_{max}$ (ng/dL) | 328 ± 178 | 333 ± 194 | 314 ± 179 |
| $T_{max}$* (hr) | 4.0 (0.0–24.5) | 7.9 (0.0–24.7) | 4.0 (0.0–24.3) |
| $C_{min}$ (ng/dL) | 175 ± 104 | 188 ± 112 | 181 ± 112 |
| $T_{min}$* (hr) | 8.01 (0.0–24.1) | 8.0 (0.0–24.0) | 8.0 (0.0–23.9) |
| Fluc Index (ratio) | 0.627 ± 0.479 | 0.556 ± 0.384 | 0.576 ± 0.341 |

*Median (Range*)

TABLE 8(b)

Baseline Testosterone Pharmacokinetic Parameters by Final Treatment Group (Mean ± SD)

| | Doses Received During Initial => Extended Treatment Phases | | | | |
|---|---|---|---|---|---|
| | 5.0 g/day T-gel | 5.0 => 7.5 g/day T-gel | 10.0 => 7.5 g/day T-gel | 10.0 g/day T-gel | T-patch |
| N | 53 | 20 | 20 | 58 | 76 |
| $C_{avg}$ (ng/dL) | 247 ± 137 | 212 ± 109 | 282 ± 157 | 236 ± 133 | 237 ± 140 |
| $C_{max}$ (ng/dL) | 333 ± 180 | 313 ± 174 | 408 ± 241 | 307 ± 170 | 314 ± 179 |
| $T_{max}$* (hr) | 4.0 (0.0–24.5) | 4.0 (0.0–24.0) | 19.7 (0.0–24.3) | 4.0 (0.0–24.7) | 4.0 (0.0–24.3) |
| $C_{min}$ (ng/dL) | 185 ± 111 | 150 ± 80 | 206 ± 130 | 182 ± 106 | 181 ± 112 |
| $T_{min}$* (hr) | 8.0 (0.0–24.1) | 11.9 (0.0–24.0) | 8.0 (0.0–23.3) | 8.0 (0.0–24.0) | 8.0 (0.0–23.9) |
| Fluc Index (ratio) | 0.600 ± 0.471 | 0.699 ± 0.503 | 0.678 ± 0.580 | 0.514 ± 0.284 | 0.576 ± 0.341 |

*Median (range)

(3) Day 1

Figure 5B:
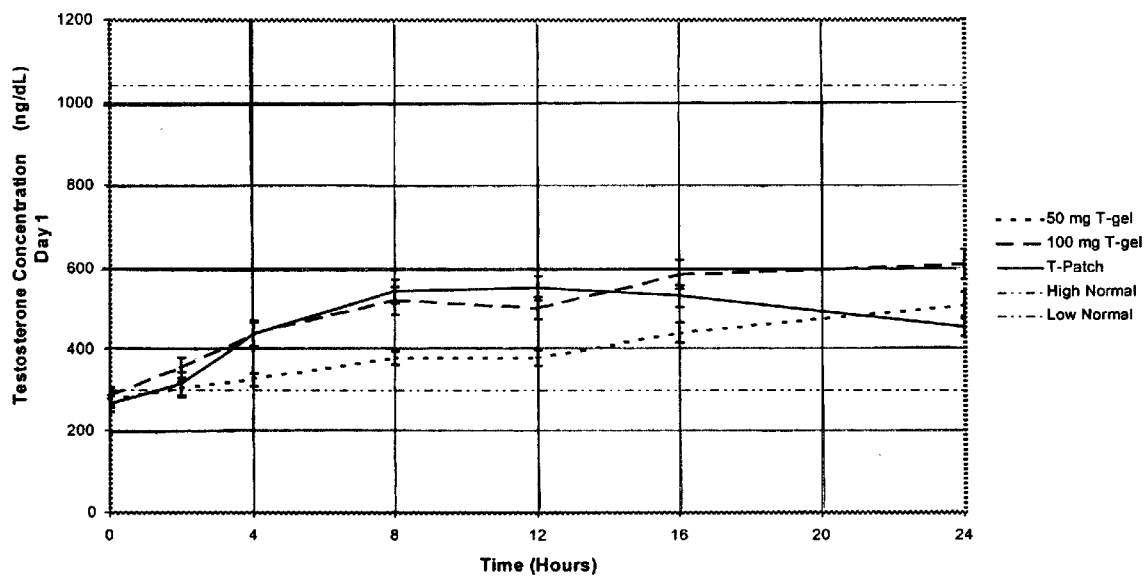
FIG. 5(b) is a graph showing the 24-hour testosterone pharmacokinetic profile for hypogonadal men on the first day of treatment with either 5.0 g/day of AndroGel®, 10.0 g/day of AndroGel®, or the testosterone patch (by initial treatment group).

FIG. 5(b) and Tables 8(c)–(d) show the pharmacokinetic profile for all three initial treatment groups after the first application of transdermnal testosterone. In general, treatment with AndroGel® and the testosterone patch produced increases in testosterone concentrations sufficiently large to bring the patients into the normal range in just a few hours. However, even on day 1, the pharmacokinetic profiles were markedly different in the AndroGel® and patch groups. Serum testosterone rose most rapidly in the testosterone patch group reaching a maximum concentration ($C_{max}$) at about 12 hours ($T_{max}$). In contrast, serum testosterone rose steadily to the normal range after AndroGel® application with $C_{max}$ levels achieved by 22 and 16 hours in the 5.0 g/day AndroGel® group and the 10.0 g/day AndroGel® group, respectively.

TABLE 8(c)

Testosterone Pharmacokinetic Parameters on Day 1 by Initial Treatment Group (Mean ± SD)

| | 5.0 g/day T-Gel | 10.0 g/day T-gel | T-patch |
|---|---|---|---|
| N | 73 | 76 | 74 |
| $C_{avg}$ (ng/dL) | 398 ± 156 | 514 ± 227 | 482 ± 204 |
| $C_{max}$ (ng/dL) | 560 ± 269 | 748 ± 349 | 645 ± 280 |
| $T_{max}$* (hr) | 22.1 (0.0–25.3) | 16.0 (0.0–24.3) | 11.8 (1.8–24.0) |
| $C_{min}$ (ng/dL) | 228 ± 122 | 250 ± 143 | 232 ± 132 |
| $T_{min}$* (hr) | 1.9 (0.0–24.0) | 0.0 (0.0–24.2) | 1.5 (0.0–24.0) |

*Median (Range)

(4) Days 30, 90, and 180

Figure 5C:
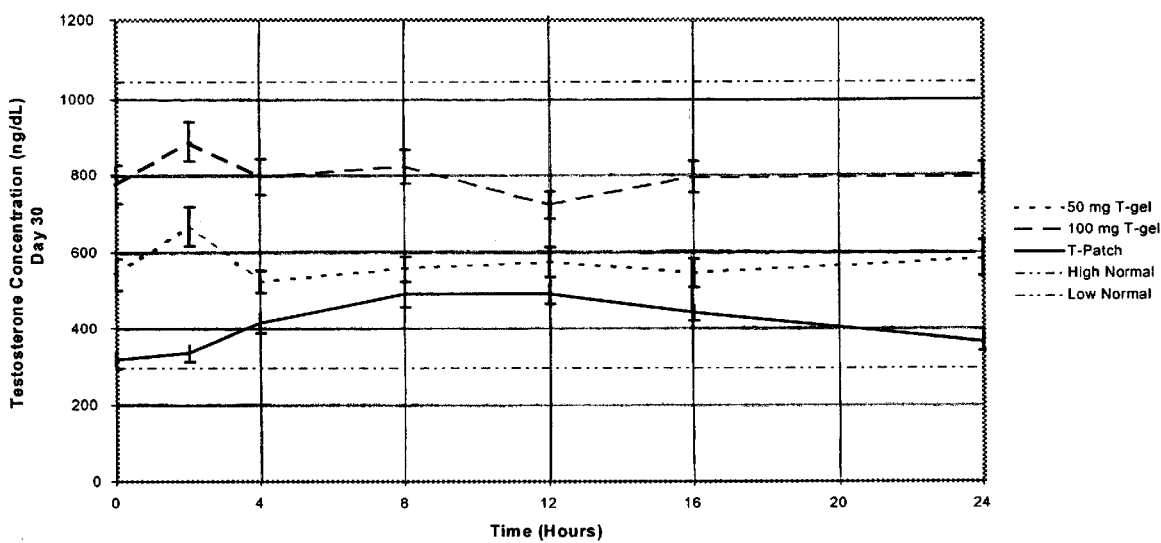
FIG. 5(c) is a graph showing the 24-hour testosterone pharmacokinetic profile for hypogonadal men on day 30 of treatment with either 5.0 g/day of AndroGel®, 10.0 g/day of AndroGel®, or the testosterone patch (by initial treatment group).
Figure 5D:
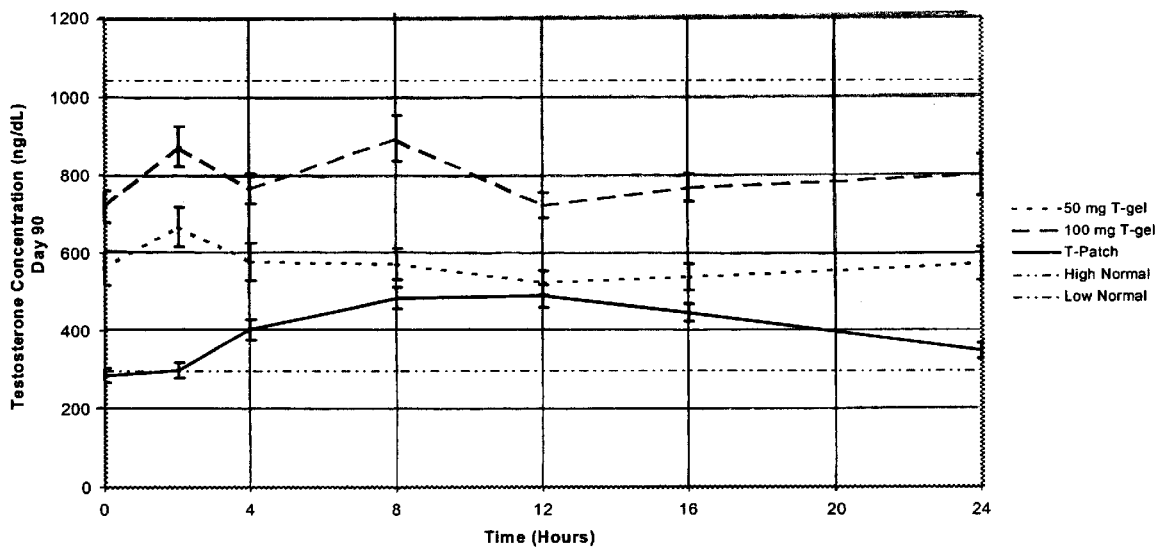
FIG. 5(d) is a graph showing the 24-hour testosterone pharmacokinetic profile for hypogonadal men on day 90 of treatment with either 5.0 g/day of AndroGel®, 10.0 g/day of AndroGel®, or the testosterone patch (by initial treatment group).

FIGS. 5(c) and 5(d) show the unique 24-hour pharmacokinetic profile of AndroGel®-treated patients on days 30 and 90. In the AndroGel® groups, serum testosterone levels showed small and variable increases shortly after dosing. The levels then returned to a relatively constant level. In contrast, in the testosterone patch group, patients exhibited a rise over the first 8 to 12 hours, a plateau for another 8 hours, and then a decline to the baseline of the prior day. Further, after gel application on both days 30 and 90, the $C_{avg}$ in the 10.0 g/day AndroGel® group was 1.4 fold higher than in the 5.0 g/day AndroGel® group and 1.9 fold higher than the testosterone patch group. The testosterone patch group also had a $C_{min}$ substantially below the lower limit of the normal range. On day 30, the accumulation ratio was 0.94 for testosterone patch group, showing no accumulation. The accumulation ratios at 1.54 and 1.9 were significantly higher in the 5.0 g/day AndroGel® group and 10.0 g/day AndroGel® group, respectively. The differences in accumulation ratio among the groups persisted on day 90. This data indicates that the AndroGel® preparations had a longer effective half-life than testosterone patch.

Figure 5E:
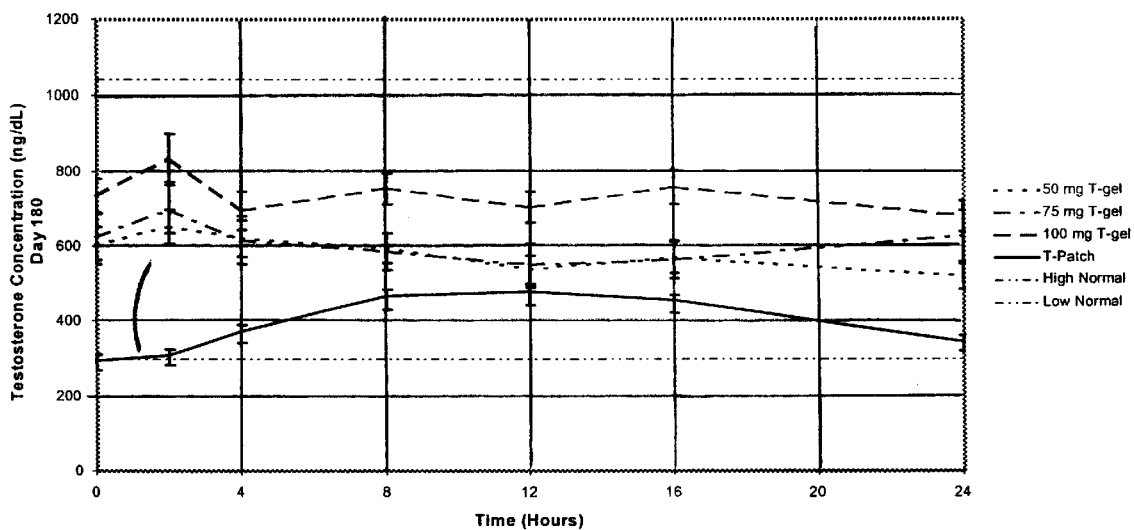
FIG. 5(e) is a graph showing the 24-hour testosterone pharmacokinetic profile for hypogonadal men on day 180 of treatment with either 5.0 g/day of AndroGel®, 10.0 g/day of AndroGel®, or the testosterone patch (by final treatment group).

FIG. 5(e) shows the 24-hour pharmacokinetic profile for the treatment groups on day 180. In general, as Table 8(e) shows, the serum testosterone concentrations achieved and the pharmacokinetic parameters were similar to those on days 30 and 90 in those patients who continued on their initial randomized treatment groups. Table 8(f) shows that the patients titrated to the 7.5 g/day AndroGel® group were not homogeneous. The patients that were previously in the 10.0 g/day group tended to have higher serum testosterone TABLE 8(d)

Testosterone Phamacokinetic Parameters on Day 1 by Final Treatment Group (Mean ± SD)

| | Doses Received During Initial => Extended Treatment Phases | | | | |
|---|---|---|---|---|---|
| | 5.0 g/day T-gel | 5.0 => 7.5 g/day T-gel | 10.0 => 7.5 g/day T-gel | 10.0 g/day T-gel | T-patch |
| N | 53 | 20 | 19 | 57 | 74 |
| $C_{avg}$ (ng/dL) | 411 ± 160 | 363 ± 143 | 554 ± 243 | 500 ± 223 | 482 ± 204 |
| $C_{max}$ (ng/dL) | 573 ± 285 | 525 ± 223 | 819 ± 359 | 724 ± 346 | 645 ± 280 |
| $T_{max}$* (hr) | 22.1 (0.0–25.3) | 19.5 (1.8–24.3) | 15.7 (3.9–24.0) | 23.0 (0.0–24.3) | 11.8 (1.8–24.0) |
| $C_{min}$ (ng/dL) | 237 ± 125 | 204 ± 112 | 265 ± 154 | 245 ± 140 | 232 ± 132 |
| $T_{min}$* (hr) | 1.8 (0.0–24.0) | 3.5 (0.0–24.0) | 1.9 (0.0–24.2) | 0.0 (0.0–23.8) | 1.5 (0.0–24.0) |
| Fluc Index (ratio) | 0.600 ± 0.471 | 0.699 ± 0.503 | 0.678 ± 0.580 | 0.514 ± 0.284 | 0.576 ± 0.341 |

*Median (range)

levels than those previously receiving 5.0 g/day. On day 180, the $C_{avg}$ in the patients in the 10.0 g/day group who converted to 7.5 g/day on day 90 was 744 ng/dL, which was 1.7 fold higher than the $C_{avg}$ of 450 ng/dL in the patients titrated to 7.5 g/day from 5.0 g/day. Despite adjusting the dose up by 2.5 g/day in the 5.0 to 7.5 g/day group, the $C_{avg}$ remained lower than those remaining in the 5.0 g/day group. In the 10.0 to 7.5 g/day group, the $C_{avg}$ became similar to those achieved by patients remaining in the 10.0 g/day group without dose titration. These results suggest that many of the under responders may actually be poorly compliant patients. For example, if a patient does not apply AndroGel® properly (e.g., preferentially from the placebo container or shortly before bathing), then increasing the dose will not provide any added benefit.

Figure 5F:
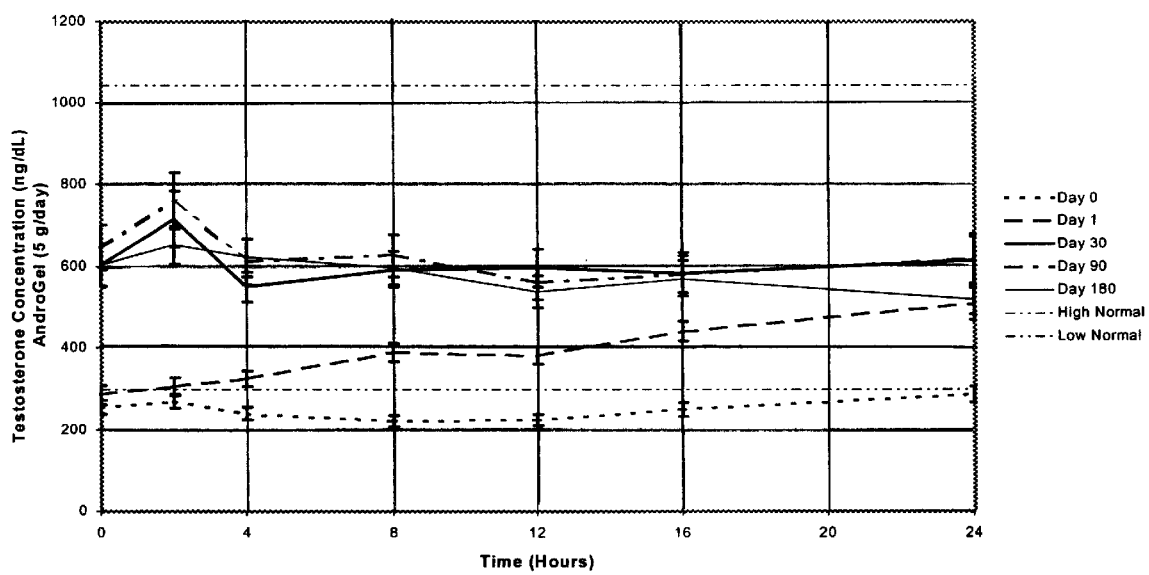
FIG. 5(f) is a graph showing the 24-hour testosterone pharmacokinetic profile for hypogonadal men on day 0, 1, 30, 90, and 180 of treatment with 5.0 g/day of AndroGel®.
Figure 5G:
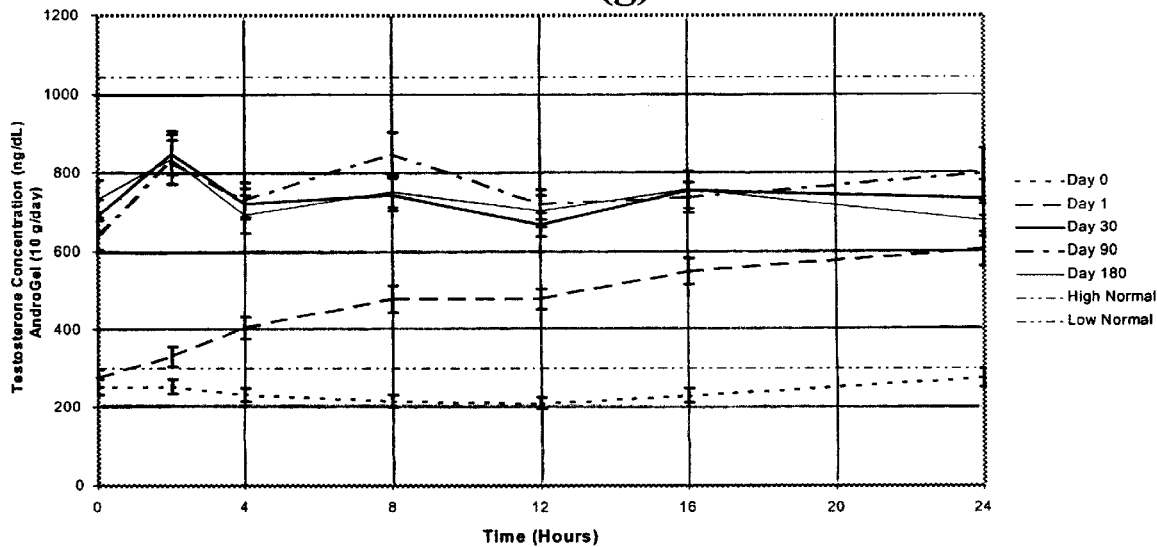
FIG. 5(g) is a graph showing the 24-hour testosterone pharmacokinetic profile for hypogonadal men on day 0, 1, 30, 90, and 180 of treatment with 10.0 g/day of AndroGel®.
Figure 5H:
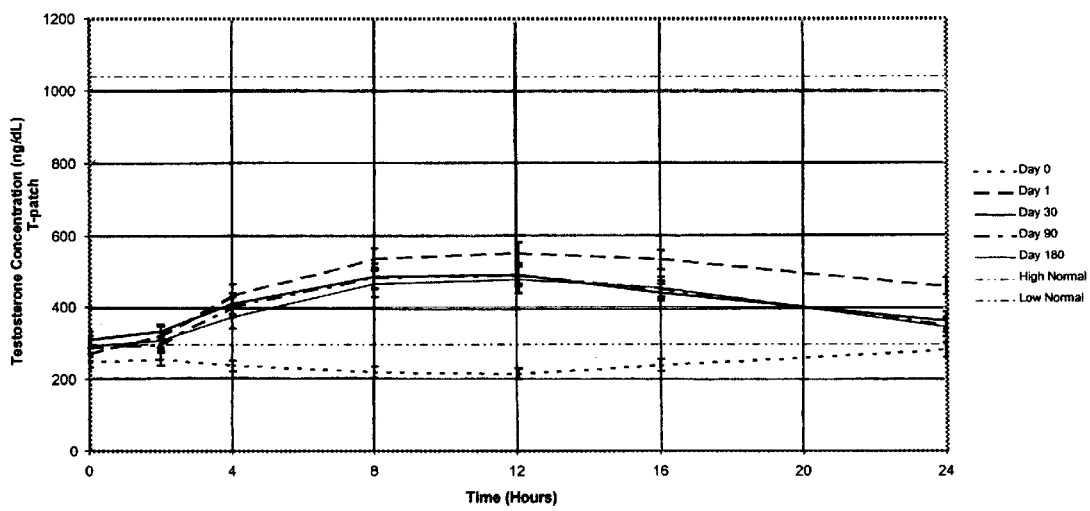
FIG. 5(h) is a graph showing the 24-hour testosterone pharmacokinetic profile for hypogonadal men on day 0, 1, 30, 90, and 180 of treatment with the testosterone patch.

FIGS. 5(f)–(h) compare the pharmacokinetic profiles for the 5.0 g/day AndroGel® group, the 10.0 g/day AndroGel® [g/day] group, and the testosterone patch group at days 0, 1, 30, 90, and 180, respectively. In general, the mean serum testosterone levels in the testosterone patch group remained at the lower limit of the normal range throughout the treatment period. In contrast, the mean serum testosterone levels remained at about 490–570 ng/dL for the 5.0 g/day AndroGel® group and about 630–860 ng/dL AndroGel® for the 10.0 g/day group.

TABLE 8(e)

Testosterone Phamacokinetic Parameters on Day 1 by Initial Treatment Group (Mean ± SD)

|  | 5.0 g/day T-Gel | 10.0 g/day T-gel | T-patch |
|---|---|---|---|
| Day 30 | N = 66 | N = 74 | N = 70 |
| $C_{avg}$ (ng/dL) | 566 ± 262 | 792 ± 294 | 419 ± 163 |

TABLE 8(e)-continued

Testosterone Phamacokinetic Parameters on Day 1 by Initial Treatment Group (Mean ± SD)

|  | 5.0 g/day T-Gel | 10.0 g/day T-gel | T-patch |
|---|---|---|---|
| $C_{max}$ (ng/dL) | 876 ± 466 | 1200 ± 482 | 576 ± 223 |
| $T_{max}$* (hr) | 7.9 (0.0–24.0) | 7.8 (0.0–24.3) | 11.3 (0.0–24.0) |
| $C_{min}$ (ng/dL) | 361 ± 149 | 505 ± 233 | 235 ± 122 |
| $T_{min}$* (hr) | 8.0 (0.0–24.1) | 8.0 (0.0–25.8) | 2.0 (0.0–24.2) |
| Fluc Index (ratio) | 0.857 ± 0.331 | 0.895 ± 0.434 | 0.823 ± 0.289 |
| Accum Ratio (ratio) | 1.529 ± 0.726 | 1.911 ± 1.588 | 0.937 ± 0.354 |
| Day 90 | N = 65 | N = 73 | N = 64 |
| $C_{avg}$ (ng/dL) | 553 ± 247 | 792 ± 276 | 417 ± 157 |
| $C_{max}$ (ng/dL) | 846 ± 444 | 1204 ± 570 | 597 ± 242 |
| $T_{max}$* (hr) | 4.0 (0.0–24.1) | 7.9 (0.0–25.2) | 8.1 (0.0–25.0) |
| $C_{min}$ (ng/dL) | 354 ± 147 | 501 ± 193 | 213 ± 105 |
| $T_{min}$* (hr) | 4.0 (0.0–25.3) | 8.0 (0.0–24.8) | 2.0 (0.0–24.0) |
| Fluc Index (ratio) | 0.851 ± 0.402 | 0.859 ± 0.399 | 0.937 ± 0.442 |
| Accum Ratio (ratio) | 1.615 ± 0.859 | 1.927 ± 1.310 | 0.971 ± 0.453 |
| Day 180 | N = 63 | N = 68 | N = 45 |
| $C_{avg}$ (ng/dL) | 520 ± 227 | 722 ± 242 | 403 ± 163 |
| $C_{max}$ (ng/dL) | 779 ± 359 | 1091 ± 437 | 580 ± 240 |
| $T_{max}$* (hr) | 4.0 (0.0–24.0) | 7.9 (0.0–24.0) | 10.0 (0.0–24.0) |
| $C_{min}$ (ng/dL) | 348 ± 164 | 485 ± 184 | 223 ± 114 |
| $T_{min}$* (hr) | 11.9 (0.0–24.0) | 11.8 (0.0–27.4) | 2.0 (0.0–25.7) |
| Fluc Index (ratio) | 0.845 ± 0.379 | 0.829 ± 0.392 | 0.891 ± 0.319 |
| Accum Ratio (ratio) | 1.523 ± 1.024 | 1.897 ± 2.123 | 0.954 ± 0.4105 |

*Median (Range)

TABLE 8(f)

Testosterone Phamacokinetic Parameters on Days 30, 90, 180 by Final Treatment Group (Mean ± SD)

Doses Received During Initial => Extended Treatment Phases

|  | 5.0 g/day T-gel | 5.0 => 7.5 g/day T-gel | 10.0 => 7.5 g/day T-gel | 10.0 g/day T-gel | T-patch |
|---|---|---|---|---|---|
| Day 30 | N = 47 | N = 19 | N = 19 | N = 55 | N = 70 |
| $C_{avg}$ (ng/dL) | 604 ± 288 | 472 ± 148 | 946 ± 399 | 739 ± 230 | 419 ± 163 |
| $C_{max}$ (ng/dL) | 941 ± 509 | 716 ± 294 | 1409 ± 556 | 1128 ± 436 | 576 ± 223 |
| $T_{max}$* (hr) | 7.9 (0.0–24.0) | 8.0 (0.0–24.0) | 8.0 (0.0–24.3) | 7.8 (0.0–24.3) | 11.3 (0.0–24.0) |
| $C_{min}$ (ng/dL) | 387 ± 159 | 296 ± 97 | 600 ± 339 | 471 ± 175 | 235 ± 122 |
| $T_{min}$* (hr) | 8.1 (0.0–24.1) | 1.7 (0.0–24.1) | 11.4 (0.0–24.1) | 8.0 (0.0–25.8) | 2.0 (0.0–24.2) |
| Fluc Index (ratio) | 0.861 ± 0.341 | 0.846 ± 0.315 | 0.927 ± 0.409 | 0.884 ± 0.445 | 0.823 ± 0.289 |
| Accum Ratio (ratio) | 1.543 ± 0.747 | 1.494 ± 0.691 | 2.053 ± 1.393 | 1.864 ± 1.657 | 0.937 ± 0.354 |
| Day 90 | N = 45 | N = 20 | N = 18 | N = 55 | N = 64 |
| $C_{avg}$ (ng/dL) | 596 ± 266 | 455 ± 164 | 859 ± 298 | 771 ± 268 | 417 ± 157 |
| $C_{max}$ (ng/dL) | 931 ± 455 | 654 ± 359 | 1398 ± 733 | 1141 ± 498 | 597 ± 242 |
| $T_{max}$* (hr) | 3.8 (0.0–24.1) | 7.7 (0.0–24.0) | 7.9 (0.0–24.0) | 7.9 (0.0–25.2) | 8.1 (0.0–25.0) |
| $C_{min}$ (ng/dL) | 384 ± 147 | 286 ± 125 | 532 ± 181 | 492 ± 197 | 213 ± 105 |
| $T_{min}$* (hr) | 7.9 (0.0–25.3) | 0.0 (0.0–24.0) | 12.0 (0.0–24.1) | 4.0 (0.0–24.8) | 2.0 (0.0–24.0) |
| Fluc Index (ratio) | 0.886 ± 0.391 | 0.771 ± 0.425 | 0.959 ± 0.490 | 0.826 ± 0.363 | 0.937 ± 0.442 |
| Accum Ratio (ratio) | 1.593 ± 0.813 | 1.737 ± 1.145 | 1.752 ± 0.700 | 1.952 ± 1.380 | 0.971 ± 0.453 |
| Day 180 | N = 44 | N = 18 | N = 19 | N = 48 | N = 41 |
| $C_{avg}$ (ng/dL) | 555 ± 225 | 450 ± 219 | 744 ± 320 | 713 ± 209 | 408 ± 165 |
| $C_{max}$ (ng/dL) | 803 ± 347 | 680 ± 369 | 1110 ± 468 | 1083 ± 434 | 578 ± 245 |

TABLE 8(f)-continued

Testosterone Phamacokinetic Parameters on Days 30, 90, 180
by Final Treatment Group (Mean ± SD)

Doses Received During Initial => Extended Treatment Phases

|  | 5.0 g/day<br>T-gel | 5.0 => 7.5 g/day<br>T-gel | 10.0 => 7.5 g/day<br>T-gel | 10.0 g/day<br>T-gel | T-patch |
|---|---|---|---|---|---|
| $T_{max}$* (hr) | 5.8 (0.0–24.0) | 2.0 (0.0–24.0) | 7.8 (0.0–24.0) | 7.7 (0.0–24.0) | 10.6 (0.0–24.0) |
| $C_{min}$ (ng/dL) | 371 ± 165 | 302 ± 150 | 505 ± 233 | 485 ± 156 | 222 ± 116 |
| $T_{min}$* (hr) | 11.9 (0.0–24.0) | 9.9 (0.0–24.0) | 12.0 (0.0–24.0) | 8.0 (0.0–27.4) | 2.0 (0.0–25.7) |
| Fluc Index (ratio) | 0.853 ± 0.402 | 0.833 ± 0.335 | 0.824 ± 0.298 | 0.818 ± 0.421 | 0.866 ± 0.311 |
| Accum Ratio (ratio) | 1.541 ± 0.917 | NA | NA | 2.061 ± 2.445 | 0.969 ± 0.415 |

*Median (range)

(5) Dose Proportionality for AndroGel®

Table 8(g) shows the increase in $AUC_{0-24}$ on days 30, 90, and 180 from the pretreatment baseline (net $AUC_{0-24}$). In order to assess dose-proportionality, the bioequivalence assessment was performed on the log-transformed AUCs using "treatment" as the only factor. The AUCs were compared after subtracting away the AUC contribution from the endogenous secretion of testosterone (the AUC on day 0) and adjusting for the two-fold difference in applied doses. The AUC ratio on day 30 was 0.95 (90% C.I.: 0.75–1.19) and on day 90 was 0.92 (90% C.I.: 0.73–1.17). When the day 30 and day 90 data was combined, the AUC ratio was 0.93 (90% C.I.: 0.79–1.10).

The data shows dose proportionality for AndroGel® treatment. The geometric mean for the increase in $AUC_{0-24}$ from day 0 to day 30 or day 90 was twice as great for the 10.0 g/day group as for the 5.0 g/day group. A 125 ng/dL mean increase in serum testosterone $C_{avg}$ level was produced by each 2.5 g/day of AndroGel®. In other words, the data shows that 0.1 g/day of AndroGel® produced, on the average, a 5 ng/dL increase in serum testosterone concentration. This dose proportionality aids dosing adjustment by the physician. Because AndroGel® is provided in 2.5 g packets (containing 25 mg of testosterone), each 2.5 g packet will produce, on average, a 125 ng/dL increase in the $C_{avg}$ for serum total testosterone.

TABLE 8(g)

Net $AUC_{0-24}$ (nmol*h/L) on Days 30, 90, and 180
after Transdermal Testosterone Application

|  | T Patch | T gel 5.0 g/day | T gel 10.0 g/day |
|---|---|---|---|
| Day 30 | 154 ± 18 | 268 ± 28 | 446 ± 30 |
| Day 90 | 157 ± 20 | 263 ± 29 | 461 ± 28 |
| Day 180 | 160 ± 25 | 250 ± 32 | 401 ± 27 |

The increase in $AUC_{0-24}$ from pretreatment baseline achieved by the 10.0 g/day and the 5.0 g/day groups were approximately 2.7 and 1.7 fold higher than that resulting from application of the testosterone patch.

b. Pharmacokinetics of Serum Free Testosterone Concentration (1) Methods

Serum free testosterone was measured by RIA of the dialysate, after an overnight equilibrium dialysis, using the same RIA reagents as the testosterone assay. The LLQ of serum free testosterone, using the equilibrium dialysis method, was estimated to be 22 pmol/L. When steroid free serum was spiked with increasing doses of testosterone in the adult male range, increasing amounts of free testosterone were recovered with a coefficient of variation that ranged from 11.0–18.5%. The intra- and interassay coefficients of free testosterone were 15% and 16.8% for adult normal male values, respectively. As estimated by the UCLA-Harbor Medical Center, free testosterone concentrations range from 3.48–17.9 ng/dL (121–620 pmol/L) in normal adult men.

(2) Pharmacokinetic Results

In general, as shown in Table 9, the pharmacokinetic parameters of serum free testosterone mirrored that of serum total testosterone as described above. At baseline (day 0), the mean serum free testosterone concentrations ($C_{avg}$) were similar in all three groups which were at the lower limit of the adult male range. The maximum serum free testosterone concentration occurred between 8 and 10 a.m., and the minimum about 8 to 16 hours later. This data is consistent with the mild diurnal variation of serum testosterone.

Figure 6A:
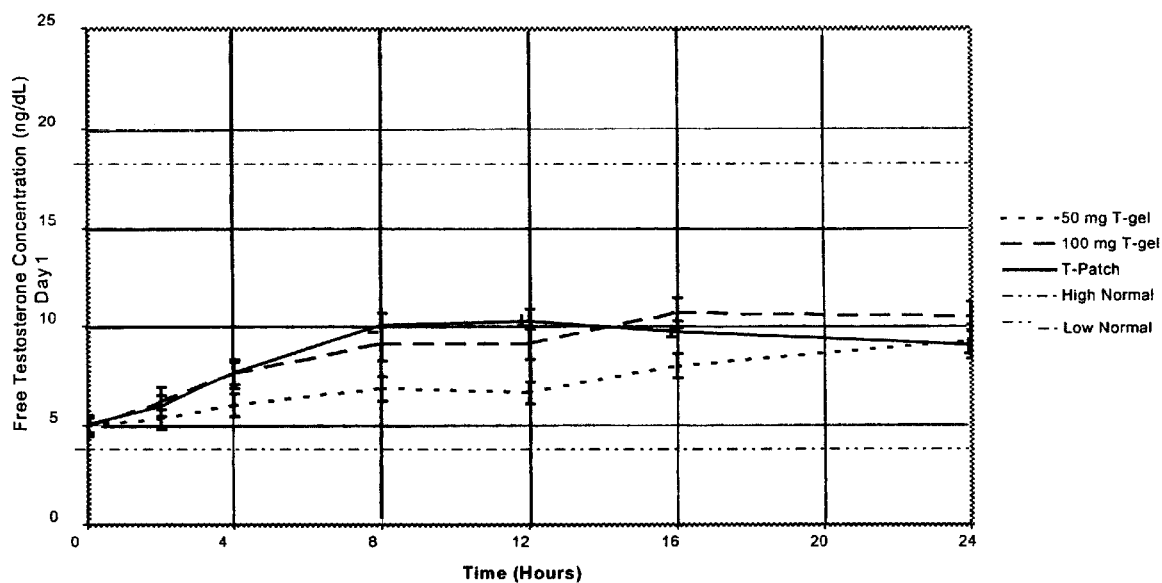
FIG. 6(a) is a graph showing the 24-hour free testosterone pharmacokinetic profile for hypogonadal men on day 1 of treatment with either 5.0 g/day of AndroGel®, 10.0 g/day of AndroGel®, or the testosterone patch (by initial treatment group).

FIG. 6(a) shows the 24-hour pharmacokinetic profiles for the three treatment groups on day 1. After application of the testosterone patch, the serum free testosterone levels peaked at 12 hours about 4 hours earlier than those achieved by the AndroGel® groups The serum free testosterone levels then declined in the testosterone patch group whereas in the AndroGel® groups, the serum free testosterone levels continued to rise.

Figure 6B:
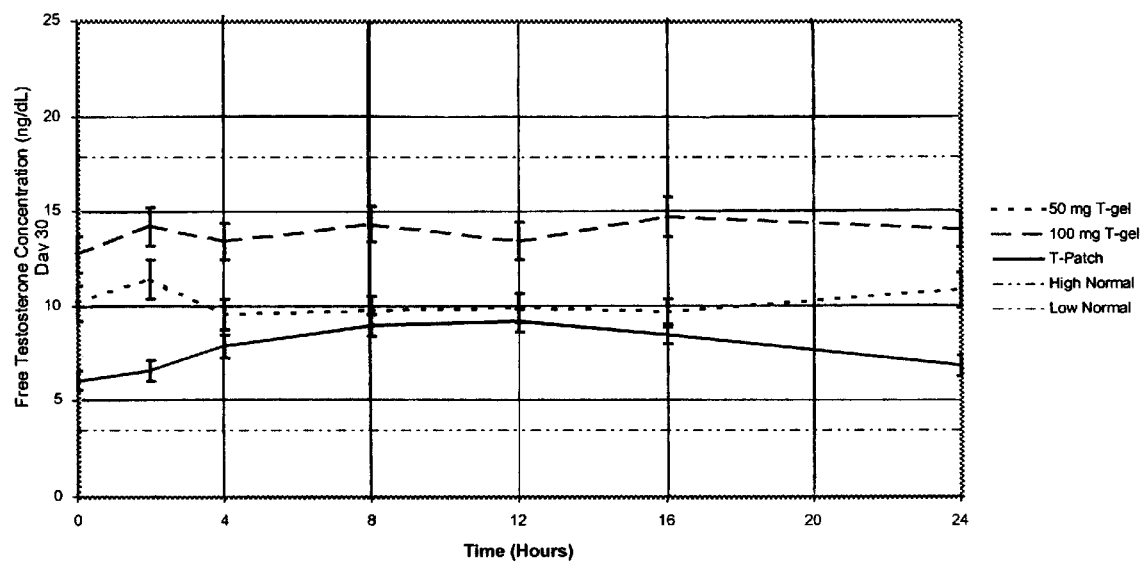
FIG. 6(b) is a graph showing the 24-hour free testosterone pharmacokinetic profile for hypogonadal men on day 30 of treatment with either 5.0 g/day of AndroGel®, 10.0 g/day of AndroGel®, or the testosterone patch (by initial treatment group).
Figure 6C:
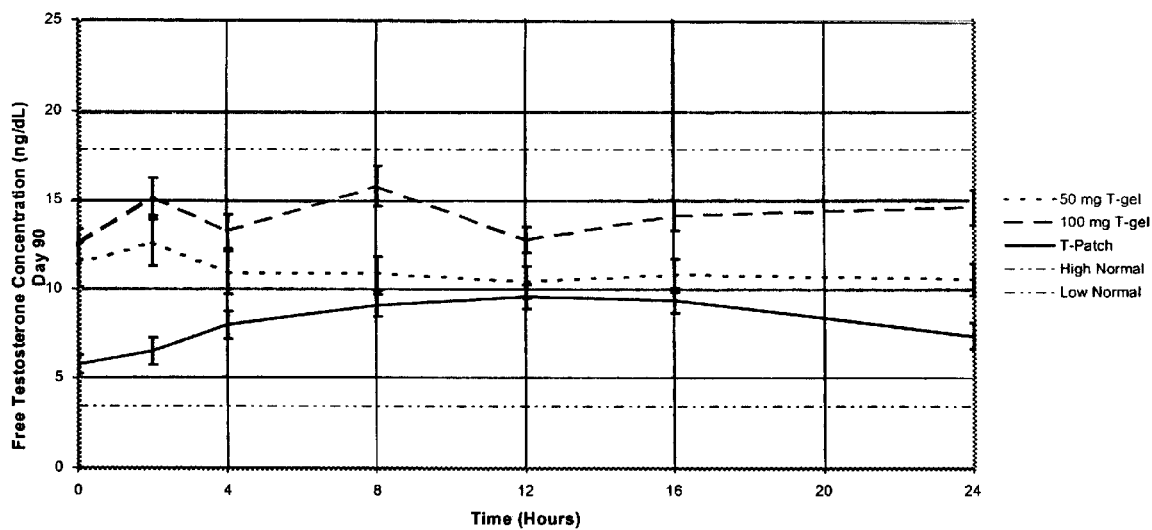
FIG. 6(c) is a graph showing the 24-hour free testosterone pharmacokinetic profile for hypogonadal men on day 90 of treatment with either 5.0 g/day of AndroGel®, 10.0 g/day of AndroGel®, or the testosterone patch (by initial treatment group).

FIGS. 6(b) and 6(c) show the pharmacokinetic profiles of free testosterone in the AndroGel®-treated groups resembled the unique testosterone profiles on days 30 and 90. After AndroGel® application, the mean serum free testosterone levels in the three groups were within normal range. Similar to the total testosterone results, the free testosterone $C_{avg}$ achieved by the 10.0 g/day group was 1.4 fold higher than the 5.0 g/day group and 1.7 fold higher than the testosterone patch group. Moreover, the accumulation ratio for the testosterone patch was significantly less than that of the 5.0 g/day AndroGel® group and the 10.0 g/day AndroGel® group.

Figure 6D:
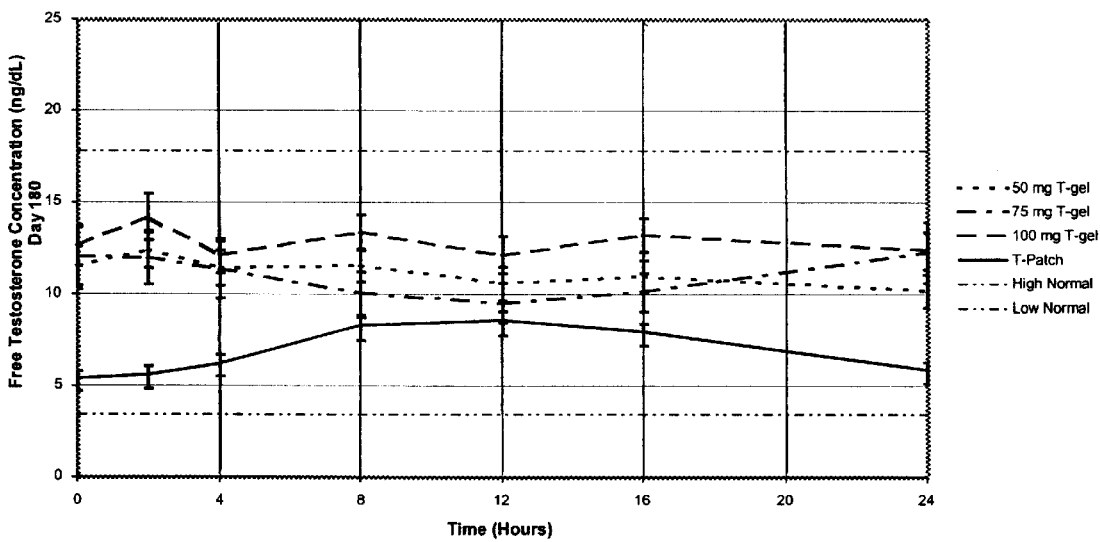
FIG. 6(d) is a graph showing the 24-hour free testosterone pharmacokinetic profile for hypogonadal men on day 180 of treatment with either 5.0 g/day of AndroGel®, 10.0 g/day of AndroGel®, or the testosterone patch (by final treatment group).

FIG. 6(d) shows the free testosterone concentrations by final treatment groups on day 180. In general, the free testosterone concentrations exhibited a similar pattern as serum testosterone. The 24-hour pharmacokinetic parameters were similar to those on days 30 and 90 in those subjects who remained in the three original randomized groups. Again, in the subjects titrated to receive 7.5 g/day of AndroGel®, the group was not homogenous. The free testosterone $C_{avg}$ in the patients with doses adjusted upwards from 5.0 to 7.5 g/day remained 29% lower than those of subjects remaining in the 5.0 g/day group. The free testosterone $C_{avg}$ in the patients whose doses were decreased from 10.0 to 7.5 g/day was 11% higher than those in remaining in the 10.0 g/day group.

Figure 6E:
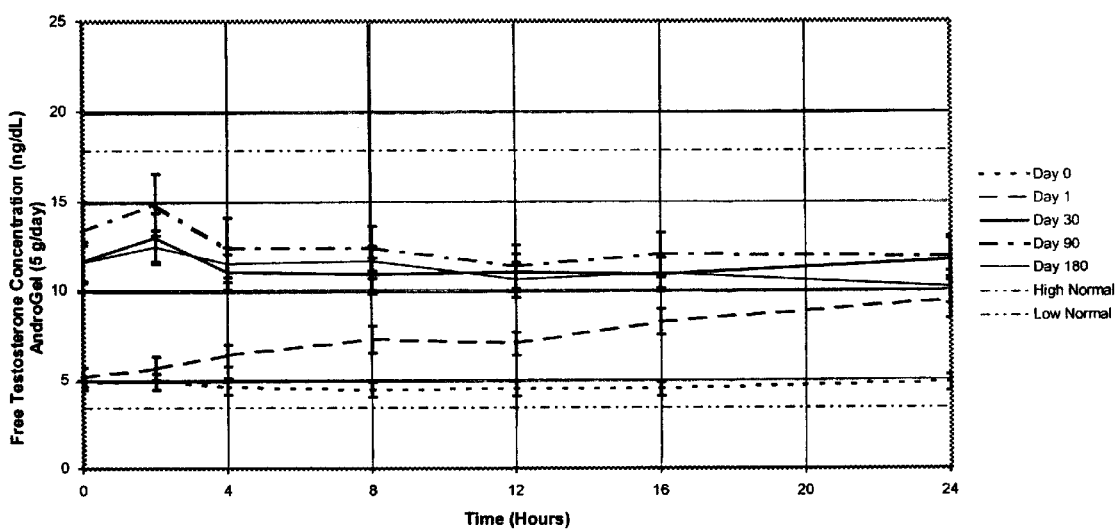
FIG. 6(e) is a graph showing the 24-hour free testosterone pharmacokinetic profile for hypogonadal men on day 0, 1, 30, 90, and 180 of treatment with 5.0 g/day of AndroGel®.
Figure 6F:
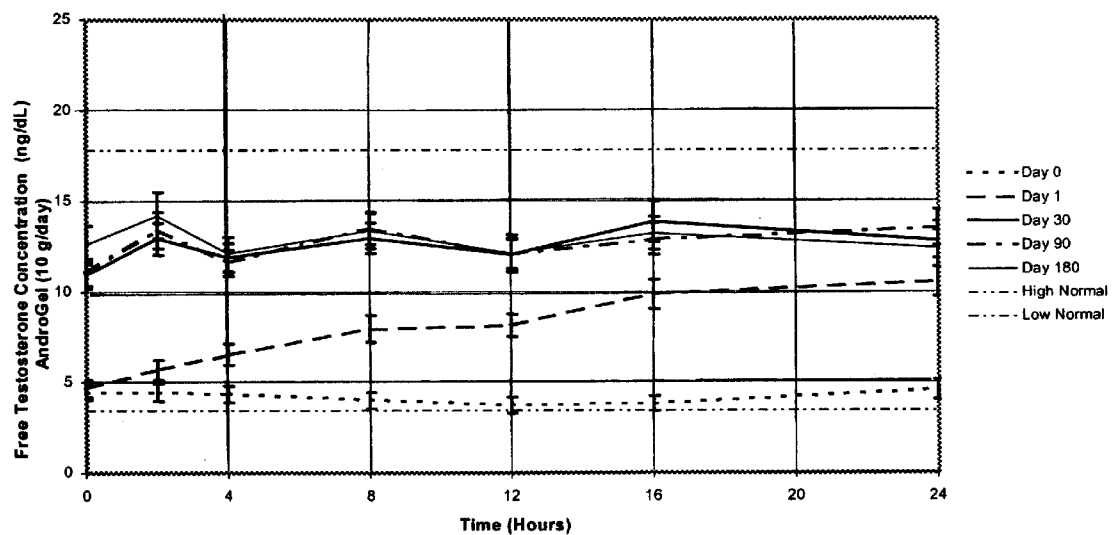
FIG. 6(f) is a graph showing the 24-hour free testosterone pharmacokinetic profile for hypogonadal men on day 0, 1, 30, 90, and 180 of treatment with 10.0 g/day of AndroGel®.
Figure 6G:
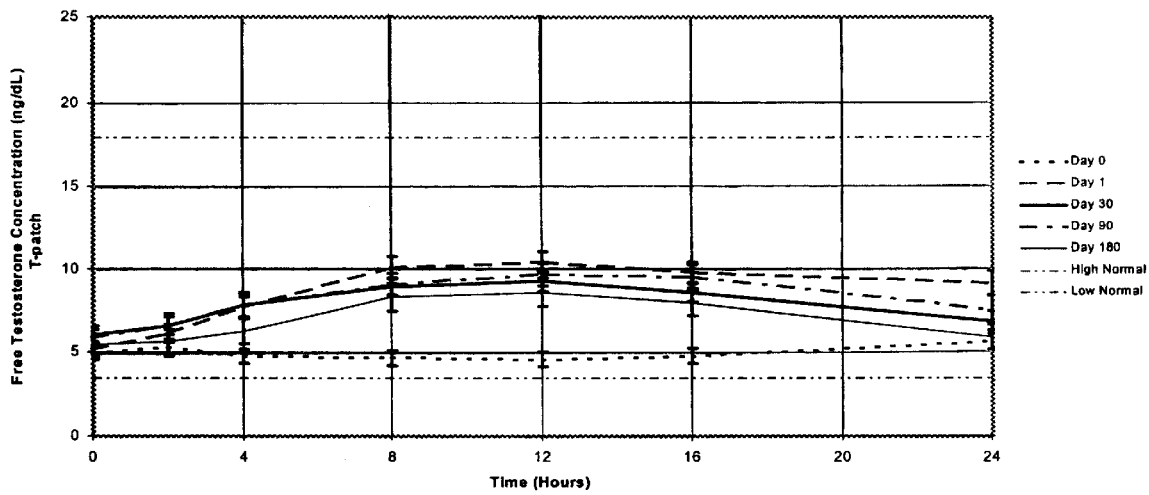
FIG. 6(g) is a graph showing the 24-hour free testosterone pharmacokinetic profile for hypogonadal men on day 0, 1, 30, 90, and 180 of treatment with the testosterone patch.

FIGS. 6(e)–(g) show the free testosterone concentrations in the three groups of subjects throughout the 180-day treatment period. Again, the free testosterone levels followed that of testosterone. The mean free testosterone levels in all three groups were within the normal range with the 10.0 g/day group maintaining higher free testosterone levels than both the 5.0 g/day and the testosterone patch groups.

114%. The intra-assay and inter-assay coefficients of variation for the DHT assay were 7.8 and 16.6%, respectively, for the normal adult male range. The normal adult male range of DHT was 30.7–193.2 ng/dL (1.06 to 6.66 nmol/L) as determined by the UCLA-Harbor Medical Center.

TABLE 9

Free Testosterone Pharmacokinetic Parameters by Final Treatment (Mean ± SD)

Doses Received During Initial => Extended Treatment Phases

|  | 5.0 g/day T-gel | 5.0 => 7.5 g/day T-gel | 10.0 => 7.5 g/day T-gel | 10.0 g/day T-gel | T-patch |
|---|---|---|---|---|---|
| Day 0 | N = 53 | N = 20 | N = 20 | N = 58 | N = 76 |
| Cavg (ng/dL) | 4.52 ± 3.35 | 4.27 ± 3.45 | 4.64 ± 3.10 | 4.20 ± 3.33 | 4.82 ± 3.64 |
| Cmax (ng/dL) | 5.98 ± 4.25 | 6.06 ± 5.05 | 6.91 ± 4.66 | 5.84 ± 4.36 | 6.57 ± 4.90 |
| Tmax* (hr) | 4.0 (0.0–24.5) | 2.0 (0.0–24.0) | 13.5 (0.0–24.2) | 2.1 (0.0–24.1) | 3.8 (0.0–24.0) |
| Cmin (ng/dL) | 3.23 ± 2.74 | 3.10 ± 2.62 | 3.14 ± 2.14 | 3.12 ± 2.68 | 3.56 ± 2.88 |
| Tmin* (hr) | 8.0 (0.0–24.2) | 9.9 (0.0–16.0) | 4.0 (0.0–23.3) | 8.0 (0.0–24.0) | 7.9 (0.0–24.0) |
| Fluc Index (ratio) | 0.604 ± 0.342 | 0.674 ± 0.512 | 0.756 ± 0.597 | 0.634 ± 0.420 | 0.614 ± 0.362 |
| Day 1 | N = 53 | N = 20 | N = 19 | N = 57 | N = 74 |
| Cavg (ng/dL) | 7.50 ± 4.83 | 6.80 ± 4.82 | 9.94 ± 5.04 | 8.93 ± 6.09 | 9.04 ± 4.81 |
| Cmax (ng/dL) | 10.86 ± 7.45 | 10.10 ± 7.79 | 15.36 ± 7.31 | 13.20 ± 8.61 | 12.02 ± 6.14 |
| Tmax* (hr) | 16.0 (0.0–25.3) | 13.9 (0.0–24.3) | 15.7 (2.0–24.0) | 23.5 (1.8–24.3) | 12.0 (1.8–24.0) |
| Cmin (ng/dL) | 4.30 ± 3.33 | 3.69 ± 3.24 | 3.88 ± 2.73 | 4.40 ± 3.94 | 4.67 ± 3.52 |
| Tmin* (hr) | 0.0 (0.0–24.1) | 1.8 (0.0–24.0) | 0.0 (0.0–24.2) | 0.0 (0.0–23.9) | 0.0 (0.0–24.0) |
| Day 30 | N = 47 | N = 19 | N = 19 | N = 55 | N = 70 |
| Cavg (ng/dL) | 11.12 ± 6.22 | 7.81 ± 3.94 | 16.18 ± 8.18 | 13.37 ± 7.13 | 8.12 ± 4.15 |
| Cmax (ng/dL) | 16.93 ± 10.47 | 11.62 ± 6.34 | 25.14 ± 10.80 | 19.36 ± 9.75 | 11.48 ± 5.78 |
| Tmax* (hr) | 8.0 (0.0–27.8) | 8.0 (0.0–26.3) | 8.0 (0.0–24.3) | 8.0 (0.0–24.3) | 8.0 (0.0–24.0) |
| Cmin (ng/dL) | 6.99 ± 3.82 | 4.78 ± 3.10 | 9.99 ± 7.19 | 8.25 ± 5.22 | 4.31 ± 3.20 |
| Tmin* (hr) | 4.0 (0.0–24.1) | 3.5 (0.0–24.1) | 11.4 (0.0–24.1) | 7.8 (0.0–25.8) | 2.0 (0.0–24.8) |
| Fluc Index (ratio) | 0.853 ± 0.331 | 0.872 ± 0.510 | 1.051 ± 0.449 | 0.861 ± 0.412 | 0.929 ± 0.311 |
| Accum Ratio (ratio) | 1.635 ± 0.820 | 1.479 ± 0.925 | 2.065 ± 1.523 | 1.953 ± 1.626 | 0.980 ± 0.387 |
| Day 90 | N = 45 | N = 20 | N = 18 | N = 55 | N = 64 |
| Cavg (ng/dL) | 12.12 ± 7.78 | 8.06 ± 3.78 | 17.65 ± 8.62 | 13.11 ± 5.97 | 8.50 ± 5.04 |
| Cmax (ng/dL) | 18.75 ± 12.90 | 10.76 ± 4.48 | 25.29 ± 12.42 | 18.61 ± 8.20 | 12.04 ± 6.81 |
| Tmax* (hr) | 4.0 (0.0–24.0) | 9.7 (0.0–24.0) | 8.0 (0.0–24.0) | 8.0 (0.0–25.2) | 11.6 (0.0–25.0) |
| Cmin (ng/dL) | 7.65 ± 4.74 | 4.75 ± 2.86 | 10.56 ± 6.07 | 8.40 ± 4.57 | 4.38 ± 3.70 |
| Tmin* (hr) | 8.0 (0.0–24.0) | 1.9 (0.0–24.0) | 5.9 (0.0–24.1) | 4.0 (0.0–24.8) | 2.0 (0.0–24.1) |
| Fluc Index (ratio) | 0.913 ± 0.492 | 0.815 ± 0.292 | 0.870 ± 0.401 | 0.812 ± 0.335 | 0.968 ± 0.402 |
| Accum Ratio (ratio) | 1.755 ± 0.983 | 1.916 ± 1.816 | 1.843 ± 0.742 | 2.075 ± 1.866 | 1.054 ± 0.498 |
| Day 180 | N = 44 | N = 18 | N = 19 | N = 48 | N = 41 |
| Cavg (ng/dL) | 11.01 ± 5.24 | 7.80 ± 4.63 | 14.14 ± 7.73 | 12.77 ± 5.70 | 7.25 ± 4.90 |
| Cmax (ng/dL) | 16.21 ± 7.32 | 11.36 ± 6.36 | 22.56 ± 12.62 | 18.58 ± 9.31 | 10.17 ± 5.90 |
| Tmax* (hr) | 7.9 (0.0–24.0) | 2.0 (0.0–23.9) | 7.8 (0.0–24.0) | 8.0 (0.0–24.0) | 11.1 (0.0–24.0) |
| Cmin (ng/dL) | 7.18 ± 3.96 | 5.32 ± 4.06 | 9.54 ± 6.45 | 8.23 ± 4.01 | 3.90 ± 4.20 |
| Tmin* (hr) | 9.9 (0.0–24.2) | 7.9 (0.0–24.0) | 8.0 (0.0–23.2) | 11.8 (0.0–27.4) | 2.5 (0.0–25.7) |
| Fluc Index (ratio) | 0.897 ± 0.502 | 0.838 ± 0.378 | 0.950 ± 0.501 | 0.815 ± 0.397 | 0.967 ± 0.370 |
| Accum Ratio (ratio) | 1.712 ± 1.071 | NA | NA | 2.134 ± 1.989 | 1.001 ± 0.580 |

*Median (Range)

c. Serum DHT Concentrations

Serum DHT was measured by RIA after potassium permanganate treatment of the sample followed by extraction. The methods and reagents of the DHT assay were provided by DSL (Webster, Tex.). The cross reactivities of the antiserum used in the RIA for DHT were 6.5% for 3-β-androstanediol, 1.2% for 3-α-androstanediol, 0.4% for 3-α-androstanediol glucuronide, and 0.4% for testosterone (after potassium permanganate treatment and extraction), and less than 0.01% for other steroids tested. This low cross-reactivity against testosterone was further confirmed by spiking steroid free serum with 35 nmol/L (1,000 pg/dL) of testosterone and taking the samples through the DHT assay. The results even on spiking with over 35 nmol/L of testosterone was measured as less than 0.1 nmol/L of DHT. The LLQ of serum DHT in the assay was 0.43 nmol/L. The mean accuracy (recovery) of the DHT assay determined by spiking steroid free serum with varying amounts of DHT from 0.43 nmol/L to 9 nmol/L was 101% and ranged from 83 to As shown in Table 10, the pretreatment mean serum DHT concentrations were between 36 and 42 ng/dL, which were near the lower limit of the normal range in all three initial treatment groups. None of the patients had DHT concentrations above the upper limit of the normal range on the pretreatment day, although almost half (103 patients) had concentrations less than the lower limit.

Figure 7:
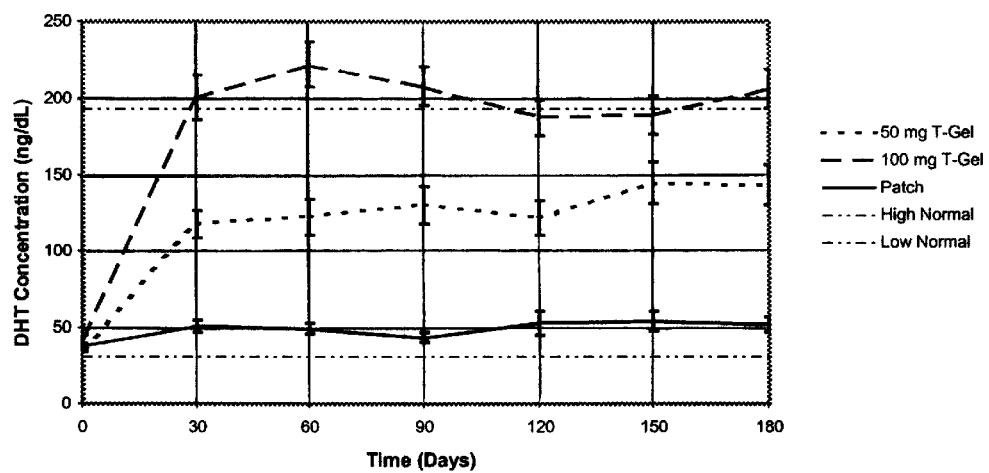
FIG. 7 is a graph showing the DHT concentrations on days 0 through 180 for hypogonadal men receiving either 5.0 g/day of AndroGel®, 10.0 g/day of AndroGel®, or the testosterone patch (by initial treatment group).

FIG. 7 shows that after treatment, the differences between the mean DHT concentrations associated with the different treatment groups were statistically significant, with patients receiving AndroGel® having a higher mean DHT concentration than the patients using the patch and showing dose-dependence in the mean serum DHT concentrations. Specifically, after testosterone patch application mean serum DHT levels rose to about 1.3 fold above the baseline. In contrast, serum DHT increased to 3.6 and 4.8 fold above baseline after application of 5.0 g/day and 10.0 g/day of AndroGel®, respectively.

TABLE 10

DHT Concentrations (ng/dL)
on Each of the Observation Days
By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day | N = 73 | N = 69 | N = 70 | N = 67 | N = 65 | N = 63 | N = 65 |
| T-gel | 36.0 ± 19.9 | 117.6 ± 74.9 | 122.4 ± 99.4 | 130.1 ± 99.2 | 121.8 ± 89.2 | 144.7 ± 110.5 | 143.7 ± 105.9 |
| 10.0 g/day | N = 78 | N = 78 | N = 74 | N = 75 | N = 68 | N = 67 | N = 71 |
| T-gel | 42.0 ± 29.4 | 200.4 ± 127.8 | 222.0 ± 126.6 | 207.7 ± 111.0 | 187.3 ± 97.3 | 189.1 ± 102.4 | 206.1 ± 105.9 |
| T-Patch | N = 76 | N = 73 | N = 68 | N = 66 | N = 49 | N = 46 | N = 49 |
|  | 37.4 ± 21.4 | 50.8 ± 34.6 | 49.3 ± 27.2 | 43.6 ± 26.9 | 53.0 ± 52.8 | 54.0 ± 42.5 | 52.1 ± 34.3 |
| Across RX | 0.6041 | 0.0001 | 0.0001 | 0.0001 | 0.0001 | 0.0001 | 0.0001 |

The increase in DHT concentrations are likely attributed to the concentration and location of 5α-reductase in the skin. For example, the large amounts of 5α-reductase in the scrotal skin presumably causes an increase in DHT concentrations in the TESTODERM® patch. In contrast, the ANDRODERM® and TESTODERM TTS® patches create little change in DTH levels because the surface area of the patch is small and little 5α-reductase is located in nonscrotal skin. AndroGel® presumably causes an increase in DHT levels because the gel is applied to a relatively large skin area and thus exposes testosterone to greater amounts of the enzyme.

To date, elevated DHT levels have not been reported to have any adverse clinical effects. Moreover, there is some evidence to suggest that increased DHT levels may inhibit prostate cancer.

d. DHT/T Ratio

Figure 8:
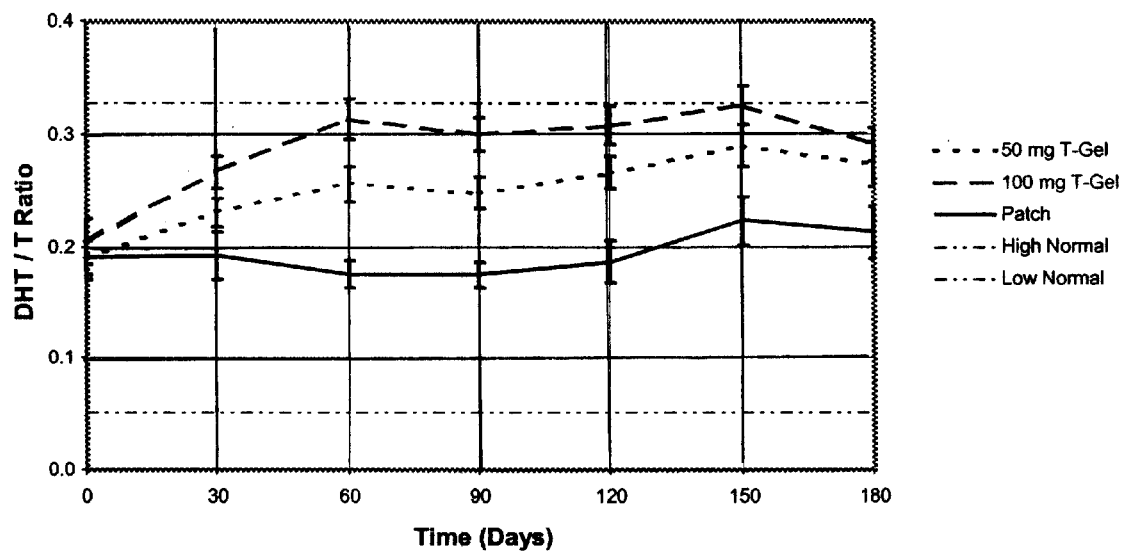
FIG. 8 is a graph showing the DHT/T ratio on days 0 through 180 for hypogonadal men receiving either 5.0 g/day of AndroGel®, 10.0 g/day of AndroGel®, or the testosterone patch (by initial treatment group).

The UCLA-Harbor Medical Center reports a DHT/T ratio of 0.052–0.328 for normal adult men. In this example, the mean ratios for all three treatments were within the normal range on day 0. As shown in FIG. 8 and Table 11, there were treatment and concentration-dependent increases observed over the 180-day period. Specifically, the AndroGel® treatment groups showed the largest increase in DHT/T ratio. However, the mean ratios for all of the treatment groups remained within the normal range on all observation days.

TABLE 11

DHT/T Ratio
on Each of the Observation Days
By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day | N = 73 | N = 68 | N = 70 | N = 67 | N = 65 | N = 62 | N = 64 |
| T-gel | 0.198 ± 0.137 | 0.230 ± 0.104 | 0.256 ± 0.132 | 0.248 ± 0.121 | 0.266 ± 0.119 | 0.290 ± 0.145 | 0.273 ± 0.160 |
| 10.0 g/day | N = 78 | N = 77 | N = 74 | N = 74 | N = 68 | N = 67 | N = 71 |
| T-gel | 0.206 ± 0.163 | 0.266 ± 0.124 | 0.313 ± 0.160 | 0.300 ± 0.131 | 0.308 ± 0.145 | 0.325 ± 0.142 | 0.291 ± 0.124 |
| T-Patch | N = 76 | N = 73 | N = 68 | N = 65 | N = 49 | N = 46 | N = 46 |
|  | 0.204 ± 0.135 | 0.192 ± 0.182 | 0.175 ± 0.102 | 0.175 ± 0.092 | 0.186 ± 0.134 | 0.223 ± 0.147 | 0.212 ± 0.160 |
| Across RX | 0.7922 | 0.0001 | 0.0001 | 0.0001 | 0.0001 | 0.0001 | 0.0002 | e. Total Androgen (DHT+T)

Figure 9:
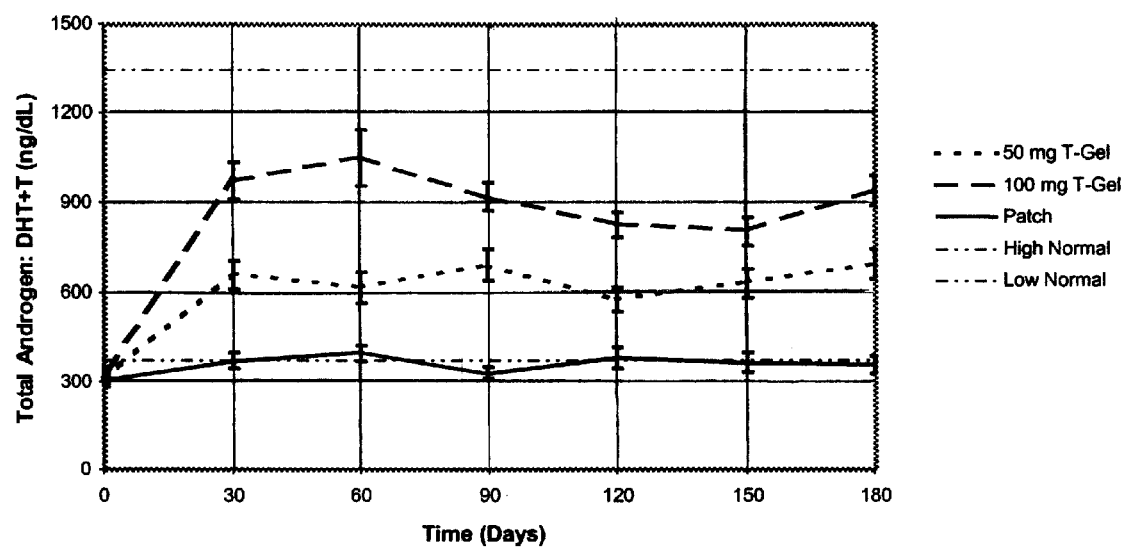
FIG. 9 is a graph showing the total androgen concentrations (DHT+T) on days 0 through 180 for hypogonadal men receiving either 5.0 g/day of AndroGel®, 10.0 g/day of AndroGel®, or the testosterone patch (by initial treatment group).

The UCLA-Harbor Medical Center has determined that the normal total androgen concentration is 372 to 1,350 ng/dL. As shown in FIG. 9 and Table 12, the mean pre-dose total androgen concentrations for all three treatments were below the lower limit of the normal range on pretreatment day 0. The total androgen concentrations for both AndroGel® groups were within the normal range on all treatment observation days. In contrast, the mean concentrations for patients receiving the testosterone patch was barely within the normal range on day 60 and 120, but were below the lower normal limit on days 30, 90, 150, and 180.

TABLE 12

Total Androgen (DHT + T) (ng/dL)
on Each of the Observation Days
By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day | N = 73 | N = 68 | N = 70 | N = 67 | N = 65 | N = 62 | N = 64 |
| T-gel | 281 ± 150 | 659 ± 398 | 617 ± 429 | 690 ± 431 | 574 ± 331 | 631 ± 384 | 694 ± 412 |
| 100 g/day | N = 78 | N = 77 | N = 74 | N = 74 | N = 68 | N = 67 | N = 71 |
| T-gel | 307 ± 180 | 974 ± 532 | 1052 ± 806 | 921 ± 420 | 827 ± 361 | 805 ± 383 | 944 ± 432 |
| T-Patch | N = 76 | N = 73 | N = 68 | N = 65 | N = 49 | N = 46 | N = 46 |
|  | 282 ± 159 | 369 ± 206 | 392 ± 229 | 330 ± 173 | 378 ± 250 | 364 ± 220 | 355 ± 202 |
| Across RX | 0.7395 | 0.0001 | 0.0001 | 0.0001 | 0.0001 | 0.0001 | 0.0001 | f. $E_2$ Concentrations

Serum $E_2$ levels were measured by a direct assay without extraction with reagents from ICN (Costa Mesa, Calif.). The intra-assay and inter-assay coefficients of variation of $E_2$ were 6.5 and 7.1% respectively. The UCLA-Harbor Medical Center reported an average $E_2$ concentration ranging from 7.1 to 46.1 pg/mL (63 to 169 pmol/L) for normal adult male range. The LLQ of the $E_2$ was 18 pmol/L. The cross reactivities of the $E_2$ antibody were 6.9% for estrone, 0.4% for equilenin, and less than 0.01% for all other steroids tested. The accuracy of the $E_2$ assay was assessed by spiking steroid free serum with increasing amount of $E_2$ (18 to 275 pmol/L). The mean recovery of $E_2$ compared to the amount added was 99.1% and ranged from 95 to 101%.

Figure 10:
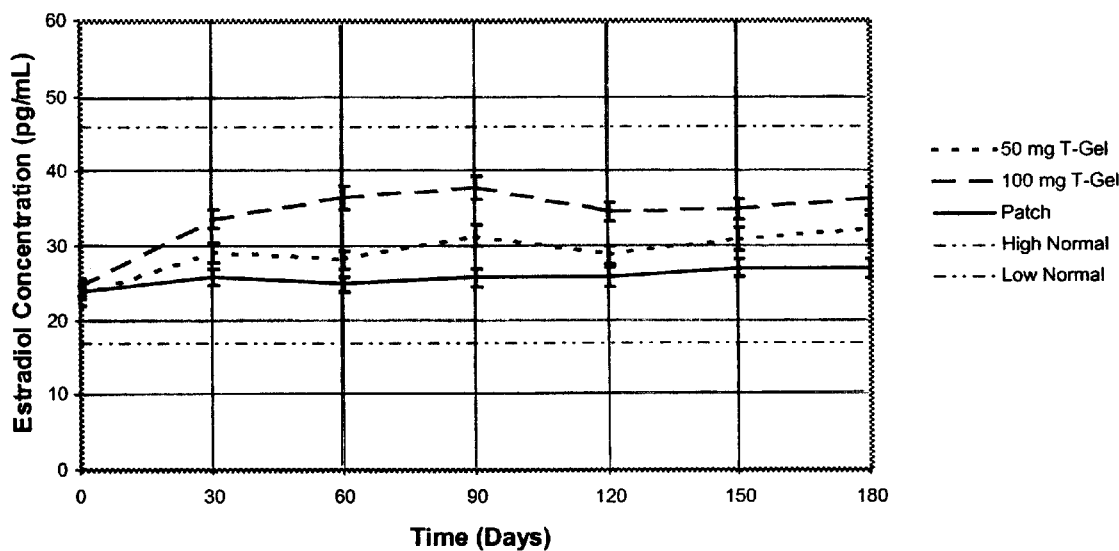
FIG. 10 is a graph showing the $E_2$ concentrations on days 0 through 180 for hypogonadal men receiving either 5.0 g/day of AndroGel®, 10.0 g/day of AndroGel®, or the testosterone patch (by initial treatment group).

FIG. 10 depicts the $E_2$ concentrations throughout the 180-day study. The pretreatment mean $E_2$ concentrations for all three treatment groups were 23–24 pg/mL. During the study, the $E_2$ levels increased by an average 9.2% in the testosterone patch during the treatment period, 30.9% in the 5.0 g/day AndroGel® group, and 45.5% in the 10.0 g/day AndroGel® group. All of the mean concentrations fell within the normal range.

$E_2$ is believed to be important for the maintenance of normal bone. In addition, $E_2$ has a positive effect on serum lipid profiles.

g. Serum SHBG Concentrations

Serum SHBG levels were measured with a fluoroimmunometric assay, ("FIA") obtained from Delfia (Wallac, Gaithersberg, Md.). The intra- and interassay coefficients were 5% and 12% respectively. The LLQ was 0.5 nmol/L. The UCLA-Harbor Medical Center determined that the adult normal male range for the SHBG assay is 0.8 to 46.6 nmol/L.

Figure 11:
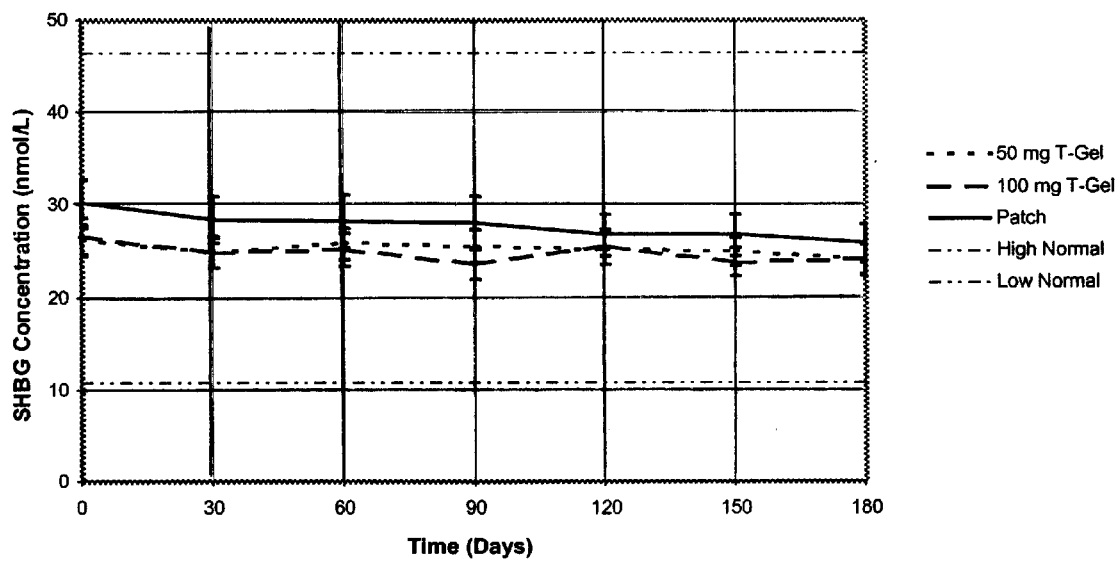
FIG. 11 is a graph showing the SHBG concentrations on days 0 through 180 for hypogonadal men receiving either 5.0 g/day of AndroGel®, 10.0 g/day of AndroGel®, or the testosterone patch (by initial treatment group).

As shown in FIG. 11 and Table 11, the serum SHBG levels were similar and within the normal adult male range in the three treatment groups at baseline. None of the treatment groups showed major changes from the baseline on any of the treatment visit days. After testosterone replacement, serum SHBG levels showed a small decrease in all three groups. The most marked change occured in the 10.0 g/day AndroGel® group.

TABLE 13

Estradiol Concentration (pg/mL)
on Each of the Observation Days
By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day | N = 73 | N = 69 | N = 68 | N = 67 | N = 64 | N = 65 | N = 65 |
| T-gel | 23.0 ± 9.2 | 29.2 ± 11.0 | 28.1 ± 10.0 | 31.4 ± 11.9 | 28.8 ± 9.9 | 30.8 ± 12.5 | 32.3 ± 13.8 |
| 10.0 g/day | N = 78 | N = 78 | N = 74 | N = 75 | N = 71 | N = 66 | N = 71 |
| T-gel | 24.5 ± 9.5 | 33.7 ± 11.5 | 36.5 ± 13.5 | 37.8 ± 13.3 | 34.6 ± 10.4 | 35.0 ± 11.1 | 36.3 ± 13.9 |
| T-Patch | N = 76 | N = 72 | N = 68 | N = 66 | N = 50 | N = 49 | N = 49 |
|  | 23.8 ± 8.2 | 25.8 ± 9.8 | 24.8 ± 8.0 | 25.7 ± 9.8 | 25.7 ± 9.4 | 27.0 ± 9.2 | 26.9 ± 9.5 |
| Across RX | 0.6259 | 0.0001 | 0.0001 | 0.0001 | 0.0001 | 0.0009 | 0.0006 |

TABLE 14

SHBG Concentration (nmol/L) on Each of the Observation Days
By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day T-gel | N = 73<br>26.2 ± 14.9 | N = 69<br>24.9 ± 14.0 | N = 69<br>25.9 ± 14.4 | N = 67<br>25.5 ± 14.7 | N = 66<br>25.2 ± 14.1 | N = 65<br>24.9 ± 12.9 | N = 65<br>24.2 ± 13.6 |
| 10.0 g/day T-gel | N = 78<br>26.6 ± 17.8 | N = 78<br>24.8 ± 14.5 | N = 75<br>25.2 ± 15.5 | N = 75<br>23.6 ± 14.7 | N = 72<br>25.5 ± 16.5 | N = 68<br>23.8 ± 12.5 | N = 71<br>24.0 ± 14.5 |
| T-Patch | N = 76<br>30.2 ± 22.6 | N = 72<br>28.4 ± 21.3 | N = 68<br>28.2 ± 23.8 | N = 66<br>28.0 ± 23.6 | N = 50<br>26.7 ± 16.0 | N = 49<br>26.7 ± 16.4 | N = 49<br>25.8 ± 15.1 |
| Across RX | 0.3565 | 0.3434 | 0.5933 | 0.3459 | 0.8578 | 0.5280 | 0.7668 | h. Gonadotropins

Serum FSH and LH were measured by highly sensitive and specific solid-phase FIA assays with reagents provided by Delfia (Wallac, Gaithersburg, Md.). The intra-assay coefficient of variations for LH and FSH fluroimmunometric assays were 4.3 and 5.2%, respectively; and the interassay variations for LH and FSH were 11.0% and 12.0%, respectively. For both LH and FSH assays, the LLQ was determined to be 0.2 IU/L. All samples obtained from the same subject were measured in the same assay. The UCLA-Harbor Medical Center reports that the adult normal male range for LH is 1.0–8.1 U/L and for FSH is 1.0–6.9 U/L.

(1) FSH

Table 15(a)–(d) shows the concentrations of FSH throughout the 180-day treatment depending on the cause of hypogonadism: (1) primary, (2) secondary, (3) age-associated, or (4) unknown.

Figure 12A:
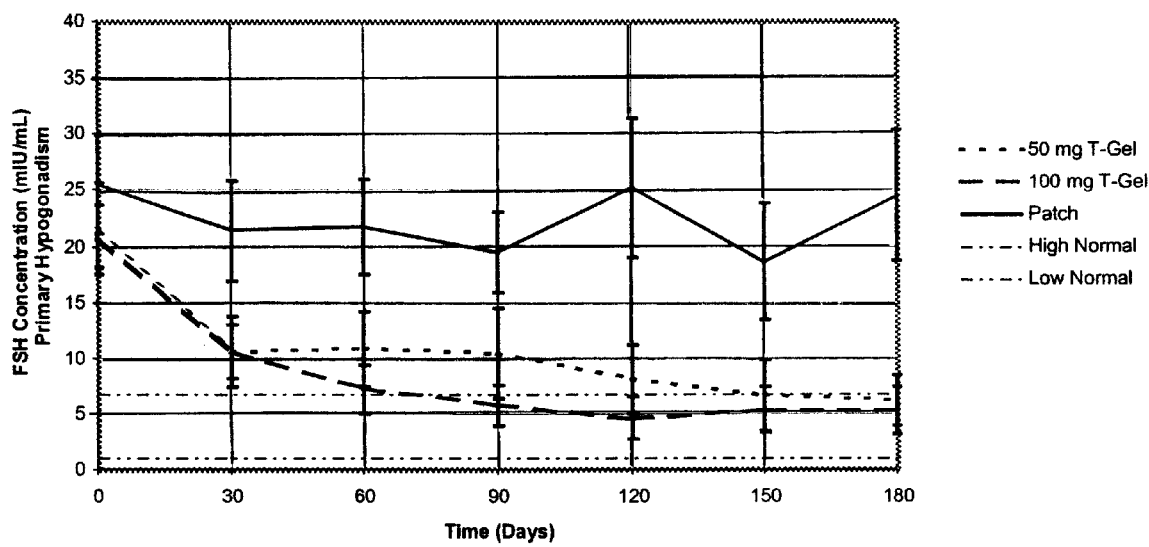
FIG. 12(a) is a graph showing the FSH concentrations on days 0 through 180 for men having primary hypogonadism and receiving either 5.0 g/day of AndroGel®, 10.0 g/day of AndroGel®, or the testosterone patch (by initial treatment group).

As discussed above, patients with primary hypogonadism have an intact feedback inhibition pathway, but the testes do not secrete testosterone. As a result, increasing serum testosterone levels should lead to a decrease in the serum FSH concentrations. In this example, a total of 94 patients were identified as having primary hypogonadism. For these patients, the mean FSH concentrations in the three treatment groups on day 0 were 21–26 mIU/mL, above the upper limit of the normal range. As shown in FIG. 12(a) and Table 15(a), the mean FSH concentrations decreased during treatment in all three treatment regimens. However, only the 10.0 g/day AndroGel® group reduced the mean concentrations to within the normal range during the first 90 days of treatment. Treatment with the 10.0 g/day AndroGel® group required approximately 120 days to reach steady state. The mean FSH concentration in patients applying 5.0 g/day of AndroGel® showed an initial decline that was completed by day 30 and another declining phase at day 120 and continuing until the end of treatment. Mean FSH concentrations in the patients receiving the testosterone patch appeared to reached steady state after 30 days but were significantly higher than the normal range.

TABLE 15(a)

FSH Concentrations (mIU/mL) on Each of the
Observation Days by Initial Treatment Group for Patients
Having Primary Hypogonadism (Mean ± SD)

|  | N | 5 g/day | N | 10 g/day | N | T-patch |
|---|---|---|---|---|---|---|
| Day 0 | 26 | 21.6 ± 21.0 | 33 | 20.9 ± 15.9 | 34 | 25.5 ± 25.5 |
| Day 30 | 23 | 10.6 ± 15.0 | 34 | 10.6 ± 14.1 | 31 | 21.4 ± 24.6 |
| Day 60 | 24 | 10.8 ± 16.9 | 32 | 7.2 ± 12.6 | 31 | 21.7 ± 23.4 |
| Day 90 | 24 | 10.4 ± 19.7 | 31 | 5.7 ± 10.1 | 30 | 19.5 ± 20.0 |
| Day 120 | 24 | 8.1 ± 15.2 | 28 | 4.6 ± 10.2 | 21 | 25.3 ± 28.4 |
| Day 150 | 22 | 6.7 ± 15.0 | 29 | 5.3 ± 11.0 | 21 | 18.6 ± 24.0 |
| Day 180 | 24 | 6.2 ± 11.3 | 28 | 5.3 ± 11.2 | 22 | 24.5 ± 27.4 |

Figure 12B:
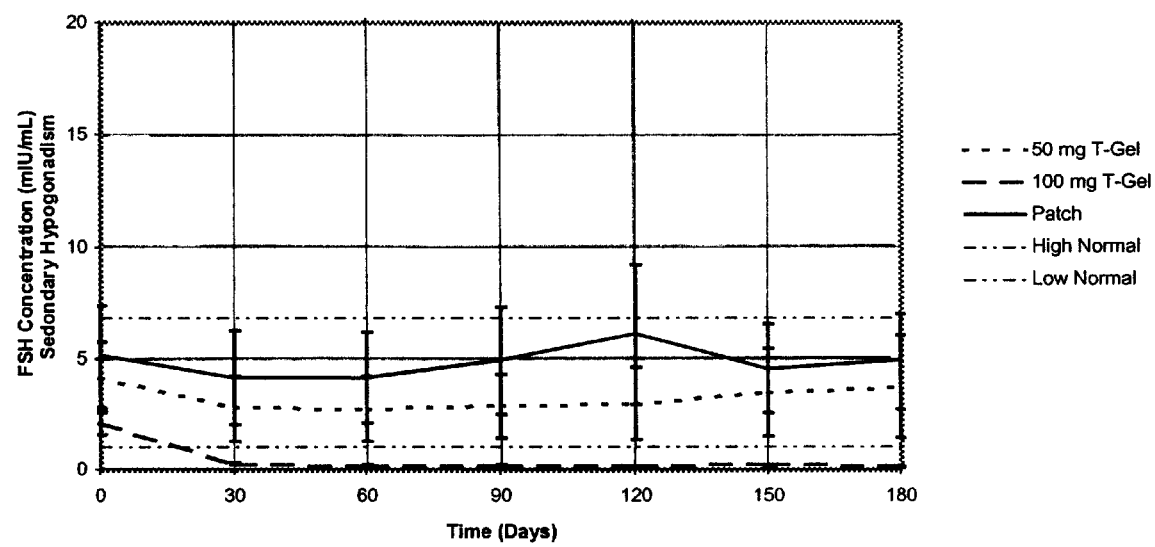
FIG. 12(b) is a graph showing the FSH concentrations on days 0 through 180 for men having secondary hypogonadism and receiving either 5.0 g/day of AndroGel®, 10.0 g/day of AndroGel®, or the testosterone patch (by initial treatment group).

Patients with secondary hypogonadism have a deficient testosterone negative feedback system. As shown in FIG. 12(b), of 44 patients identified as having secondary hypogonadism, the mean FSH concentrations decreased during treatment, although the decrease over time was not statistically significant for the testosterone patch. The patients in the 5.0 g/day AndroGel® group showed a decrease in the mean FSH concentration by about 35% by day 30, with no further decrease evident by day 60. Beyond day 90, the mean FSH concentration in the patients appeared to slowly return toward the pretreatment value. By day 30, all of the 10.0 g/day AndroGel® group had FSH concentrations less than the lower limit.

TABLE 15(b)

FSH Concentrations (mIU/mL) on Each of the
Observation Days by Initial Treatment Group for Patients
Having Secondary Hypogonadism (Mean ± SD)

|  | N | 5 g/day | N | 10 g/day | N | T-patch |
|---|---|---|---|---|---|---|
| Day 0 | 17 | 4.2 ± 6.6 | 12 | 2.1 ± 1.9 | 15 | 5.1 ± 9.0 |
| Day 30 | 16 | 2.8 ± 5.9 | 12 | 0.2 ± 0.1 | 14 | 4.2 ± 8.0 |
| Day 60 | 17 | 2.8 ± 6.1 | 12 | 0.2 ± 0.1 | 13 | 4.2 ± 7.4 |
| Day 90 | 15 | 2.9 ± 5.6 | 12 | 0.2 ± 0.1 | 14 | 4.9 ± 9.0 |
| Day 120 | 14 | 3.0 ± 6.1 | 12 | 0.1 ± 0.1 | 12 | 6.1 ± 10.7 |
| Day 150 | 14 | 3.5 ± 7.5 | 12 | 0.2 ± 0.2 | 11 | 4.6 ± 6.5 |
| Day 180 | 14 | 3.7 ± 8.6 | 12 | 0.1 ± 0.1 | 12 | 4.9 ± 7.4 |

Figure 12C:
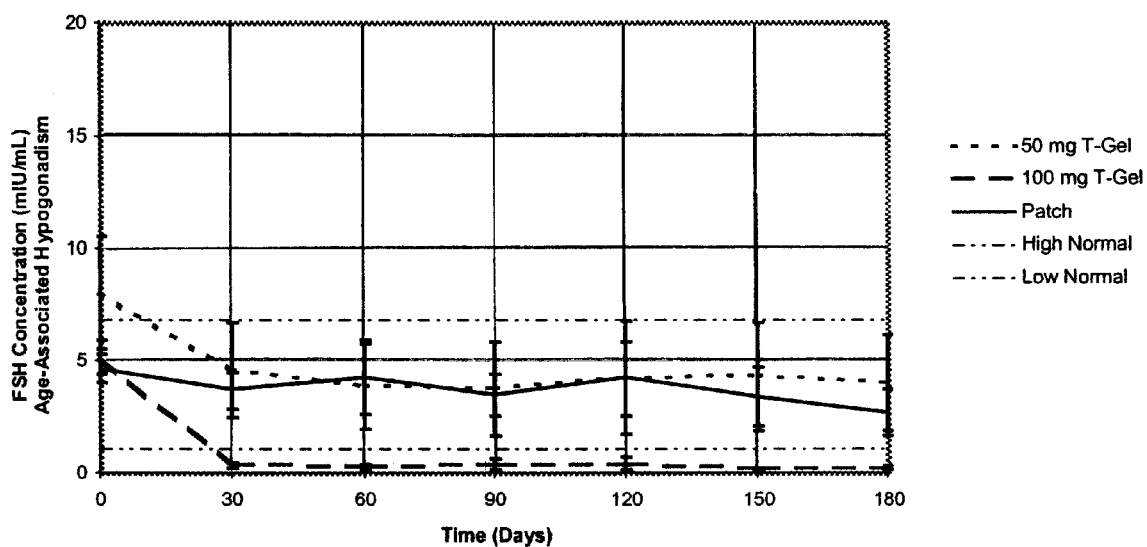
FIG. 12(c) is a graph showing the FSH concentrations on days 0 through 180 for men having age-associated hypogonadism and receiving either 5.0 g/day of AndroGel®, 10.0 g/day of AndroGel®, or the testosterone patch (by initial treatment group).

Twenty-five patients were diagnosed with age-associated hypogonadism. As shown in FIG. 12(c), the 5.0 g/day AndroGel® group had a mean pretreatment FSH concentration above the normal range. The mean concentration for this group was within the normal range by day 30 and had decreased more than 50% on days 90 and 180. The decrease in FSH mean concentration in the 10.0 g/day AndroGel® group showed a more rapid response. The concentrations in all six patients decreased to below the lower normal limit by day 30 and remained there for the duration of the study. The six patients who received the testosterone patch exhibited no consistent pattern in the mean FSH level; however, there was an overall trend towards lower FHS levels with continued treatment.

TABLE 15(c)

FSH Concentrations (mIU/mL) on Each of the
Observation Days by Initial Treatment Group for Patients
Having Age-Related Hypogonadism (Mean ± SD)

|  | N | 5 g/day | N | 10 g/day | N | T-patch |
|---|---|---|---|---|---|---|
| Day 0 | 13 | 8.0 ± 9.1 | 6 | 5.2 ± 1.9 | 6 | 4.7 ± 1.7 |
| Day 30 | 12 | 4.6 ± 7.4 | 6 | 0.4 ± 0.3 | 6 | 3.7 ± 2.0 |
| Day 60 | 12 | 3.9 ± 6.6 | 6 | 0.3 ± 0.3 | 4 | 4.3 ± 3.3 |
| Day 90 | 11 | 3.8 ± 7.0 | 6 | 0.4 ± 0.7 | 4 | 3.5 ± 1.9 |
| Day 120 | 11 | 4.2 ± 8.3 | 6 | 0.4 ± 0.7 | 4 | 4.2 ± 3.3 |
| Day 150 | 11 | 4.3 ± 8.1 | 5 | 0.2 ± 0.2 | 4 | 3.4 ± 2.7 |
| Day 180 | 11 | 4.0 ± 7.2 | 6 | 0.2 ± 0.2 | 4 | 2.7 ± 2.1 |

Figure 12D:
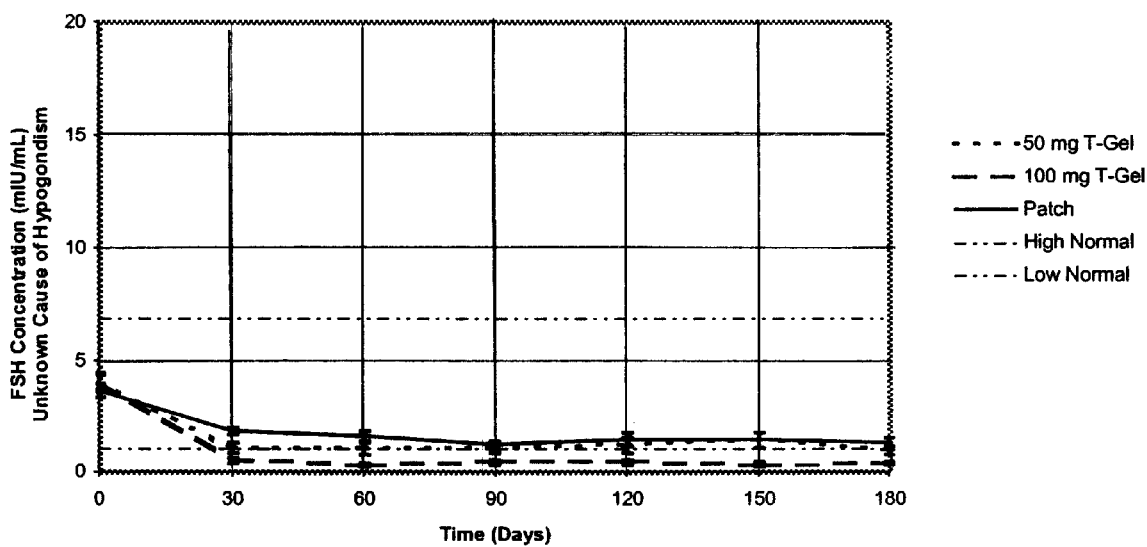
FIG. 12(d) is a graph showing the FSH concentrations on days 0 through 180 for men having hypogonadism of an unknown origin and receiving either 5.0 g/day of AndroGel®, 10.0 g/day of AndroGel®, or the testosterone patch (by initial treatment group).

Sixty-four patients in the study suffered from unclassified hypogonadism. As shown in FIG. 12(d), the patients showed a marked and comparatively rapid FSH concentration decrease in all three groups, with the greatest decrease being in the 10.0 g/day AndroGel® group. The 10.0 g/day AndroGel® group produced nearly a 90% decrease in the mean FSH concentration by day 30 and maintained the effect to day 180. The 5.0 g/day AndroGel® group produced about a 75% drop in mean FSH concentration by day 30 and stayed at that level for the remainder of treatment. The 21 patients receiving the testosterone patch had a 50% decrease in the mean FSH concentration by day 30, a trend that continued to day 90 when the concentration was about one-third of its pretreatment value.

TABLE 15(d)

Concentrations (mIU/mL) for FSH on Each of the Observation Days by Initial Treatment Group for Patients Having Unknown-Related Hypogonadism (Mean ± SD)

|  | N | 5 g/day | N | 10 g/day | N | T-patch |
| --- | --- | --- | --- | --- | --- | --- |
| Day 0 | 17 | 4.0 ± 1.8 | 26 | 4.1 ± 1.6 | 21 | 3.7 ± 1.4 |
| Day 30 | 17 | 1.1 ± 1.0 | 26 | 0.5 ± 0.5 | 21 | 1.8 ± 0.8 |
| Day 60 | 16 | 1.1 ± 1.1 | 26 | 0.3 ± 0.3 | 18 | 1.6 ± 1.0 |
| Day 90 | 17 | 1.1 ± 1.1 | 25 | 0.4 ± 0.7 | 18 | 1.2 ± 0.9 |
| Day 120 | 16 | 1.2 ± 1.4 | 26 | 0.4 ± 0.6 | 12 | 1.4 ± 1.0 |
| Day 150 | 17 | 1.4 ± 1.4 | 23 | 0.3 ± 0.5 | 13 | 1.4 ± 1.2 |
| Day 180 | 16 | 1.0 ± 0.9 | 24 | 0.4 ± 0.4 | 11 | 1.3 ± 0.9 |

This data shows that feedback inhibition of FSH secretion functioned to some extent in all four subpopulations. The primary hypogonadal population showed a dose-dependency in both the extent and rate of the decline in FSH levels. The sensitivity of the feedback process appeared to be reduced in the secondary and age-associated groups in that only the highest testosterone doses had a significant and prolonged impact on FSH secretion. In contrast, the feedback inhibition pathway in the patients in the unclassified group was quite responsive at even the lowest dose of exogenous testosterone.

(2) LH

The response of LH to testosterone was also examined separately for the same four subpopulations. Tables 16(a)–(d) shows the LH concentrations throughout the treatment period.

Figure 13A:
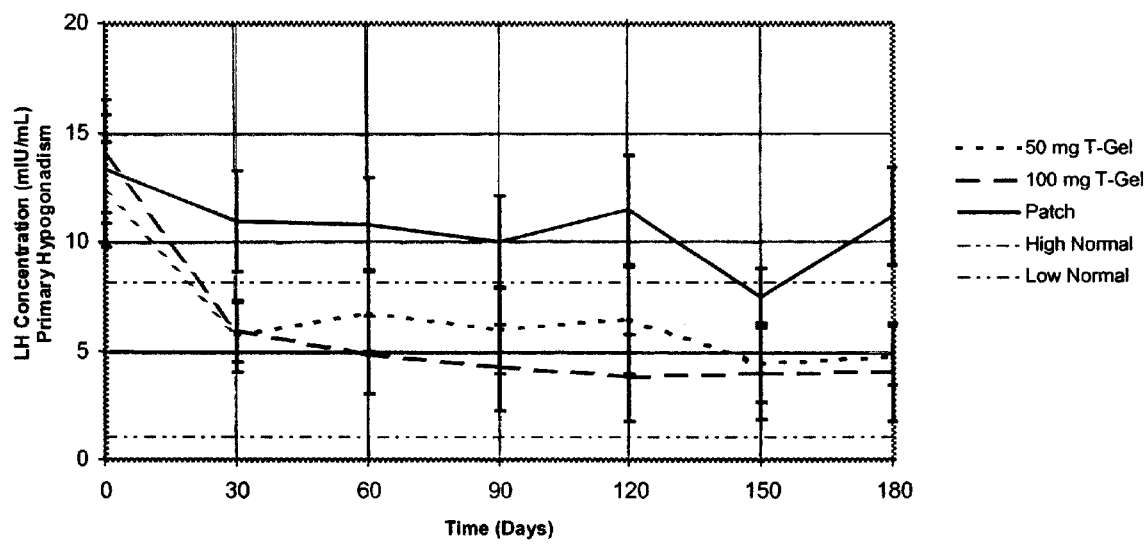
FIG. 13(a) is a graph showing the LH concentrations on days 0 through 180 for men having primary hypogonadism and receiving either 5.0 g/day of AndroGel®, 10.0 g/day of AndroGel®, or the testosterone patch (by initial treatment group).

As shown in FIG. 13(a) and Table 16(a), the LH concentrations prior to treatment were about 175% of the upper limit of the normal range in primary hypogonadal patients. The mean LH concentrations decreased during treatment in all groups. However, only the AndroGel® groups decreased the mean LH concentrations enough to fall within the normal range. As with FSH, the primary hypogonadal men receiving AndroGel® showed dose-dependence in both the rate and extent of the LH response.

TABLE 16(a)

Concentrations for LH (mIU/mL) on Each of the Observation Days for Patients Having Primary Hypogonadism (Summary of Mean ± SD)

|  | N | 5 g/day | N | 10 g/day | N | T-patch |
| --- | --- | --- | --- | --- | --- | --- |
| Day 0 | 26 | 12.2 ± 12.1 | 33 | 13.9 ± 14.9 | 33 | 13.3 ± 14.3 |
| Day 30 | 23 | 5.6 ± 7.6 | 34 | 5.9 ± 8.1 | 31 | 10.9 ± 12.9 |
| Day 60 | 24 | 6.8 ± 9.0 | 32 | 4.8 ± 10.0 | 31 | 10.8 ± 11.8 |
| Day 90 | 24 | 5.9 ± 9.5 | 31 | 4.2 ± 11.0 | 30 | 10.0 ± 11.7 |
| Day 120 | 24 | 16.4 ± 11.9 | 28 | 3.8 ± 10.4 | 21 | 11.5 ± 11.5 |
| Day 150 | 22 | 4.4 ± 8.5 | 29 | 4.0 ± 11.3 | 21 | 7.4 ± 6.0 |
| Day 180 | 24 | 4.8 ± 6.8 | 28 | 4.0 ± 11.9 | 22 | 11.2 ± 10.5 |

Figure 13B:
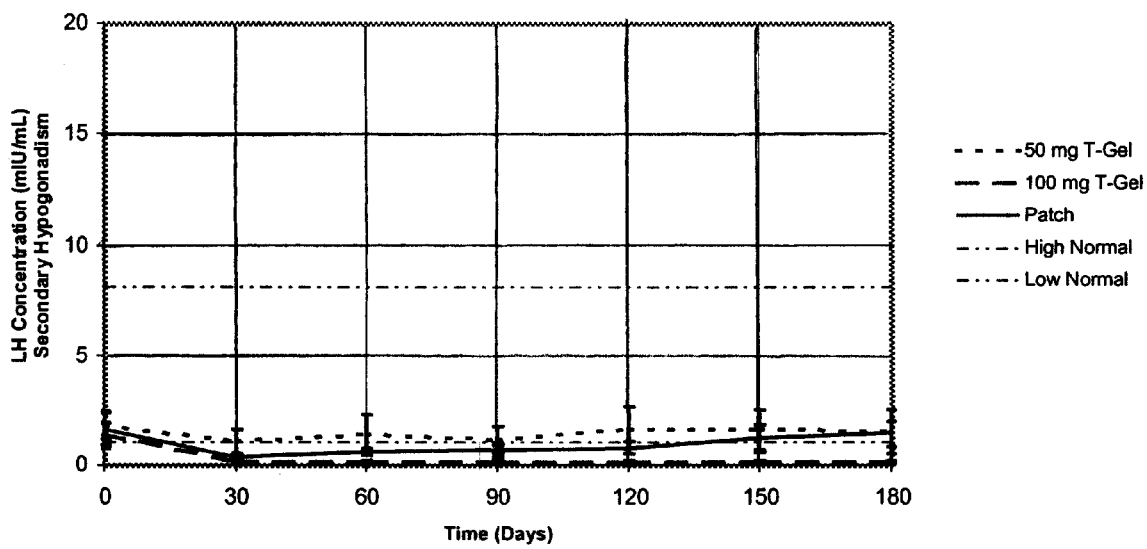
FIG. 13(b) is a graph showing the LH concentrations on days 0 through 180 for men having secondary hypogonadism and receiving either 5.0 g/day of AndroGel®, 10.0 g/day of AndroGel®, or the testosterone patch (by initial treatment group).

The secondary hypogonadal men were less sensitive to exogenous testosterone. For the 44 patients identified as having secondary hypogpnadism, the pretreatment mean concentrations were all within the lower limit normal range. The mean LH concentrations decreased during treatment with all three regimens as shown in FIG. 13(b) and Table 16(b).

TABLE 16(b)

Concentrations for LH (mIU/mL) on Each of the Observation Days for Patients Having Secondary Hypogonadism (Summary of Mean ± SD)

|  | N | 5 g/day | N | 10 g/day | N | T-patch |
| --- | --- | --- | --- | --- | --- | --- |
| Day 0 | 17 | 1.8 ± 2.6 | 12 | 1.4 ± 1.8 | 15 | 1.6 ± 3.1 |
| Day 30 | 16 | 1.1 ± 2.2 | 12 | 0.2 ± 0.2 | 14 | 0.4 ± 0.4 |
| Day 60 | 17 | 1.4 ± 3.8 | 12 | 0.2 ± 0.2 | 13 | 0.6 ± 0.5 |
| Day 90 | 15 | 1.2 ± 2.4 | 12 | 0.2 ± 0.2 | 14 | 0.7 ± 1.0 |
| Day 120 | 14 | 1.6 ± 4.0 | 12 | 0.2 ± 0.2 | 12 | 0.8 ± 0.8 |
| Day 150 | 14 | 1.6 ± 3.5 | 12 | 0.2 ± 0.2 | 11 | 1.2 ± 2.0 |
| Day 180 | 14 | 1.5 ± 3.7 | 12 | 0.2 ± 0.2 | 12 | 1.4 ± 2.1 |

Figure 13C:
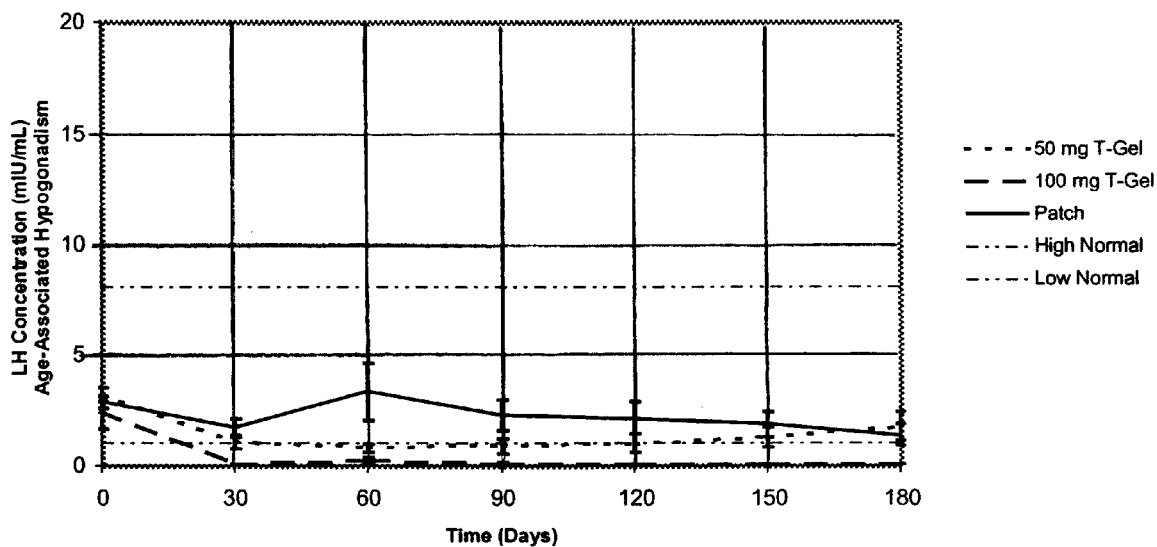
FIG. 13(c) is a graph showing the LH concentrations on days 0 through 180 for men having age-associated hypogonadism and receiving either 5.0 g/day of AndroGel®, 10.0 g/day of AndroGel®, or the testosterone patch (by initial treatment group).

None of the 25 patients suffering from age-associated hypogonadism had pretreatment LH concentrations outside of the normal range as shown in FIG. 13(c) and Table 16(c). The overall time and treatment effects were significant for the AndroGel® patients but not those patients using the testosterone patch.

TABLE 16(c)

Concentrations for LH (mIU/mL) on Each of the Observation Days for Patients Having Age-Related Hypogonadism (Summary of Mean ± SD)

|  | N | 5 g/day | N | 10 g/day | N | T-patch |
| --- | --- | --- | --- | --- | --- | --- |
| Day 0 | 13 | 3.2 ± 1.1 | 6 | 2.4 ± 1.8 | 6 | 2.9 ± 0.6 |
| Day 30 | 12 | 1.1 ± 1.0 | 6 | 0.1 ± 0.0 | 6 | 1.8 ± 1.1 |
| Day 60 | 12 | 0.8 ± 0.7 | 6 | 0.2 ± 0.3 | 5 | 3.4 ± 2.8 |
| Day 90 | 11 | 0.9 ± 1.2 | 6 | 0.1 ± 0.0 | 4 | 2.3 ± 1.4 |
| Day 120 | 11 | 1.0 ± 1.4 | 6 | 0.1 ± 0.0 | 4 | 2.2 ± 1.4 |
| Day 150 | 11 | 1.3 ± 1.5 | 5 | 0.1 ± 0.0 | 4 | 1.9 ± 1.2 |
| Day 180 | 11 | 1.8 ± 2.1 | 6 | 0.1 ± 0.0 | 4 | 1.4 ± 1.0 |

Figure 13D:
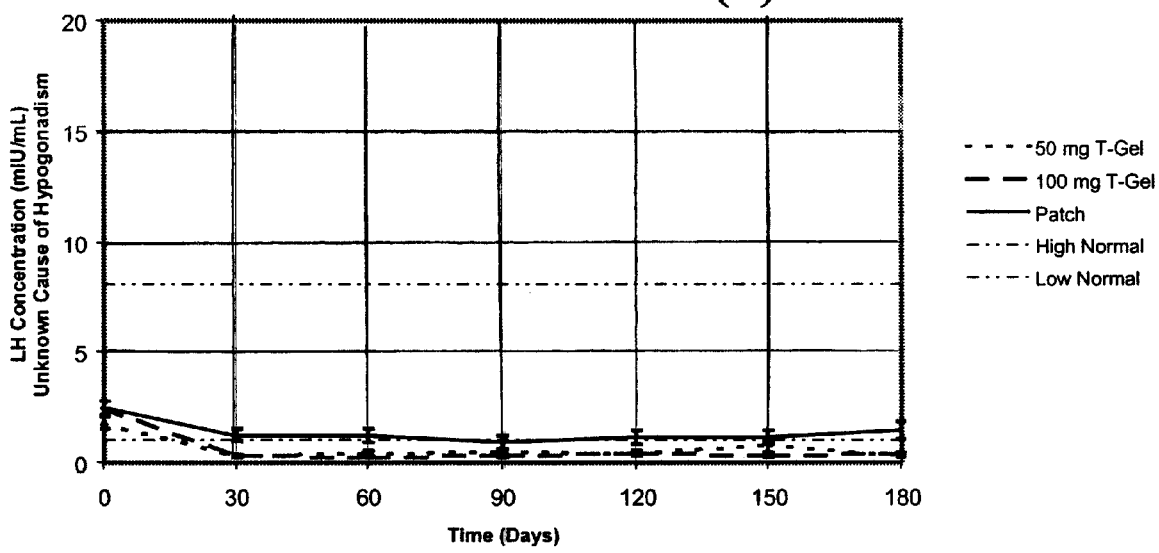
FIG. 13(d) is a graph showing the LH concentrations on days 0 through 180 for men having hypogonadism of an unknown origin and receiving either 5.0 g/day of AndroGel®, 10.0 g/day of AndroGel®, or the testosterone patch (by initial treatment group).

Of the 64 patients suffering from an unclassified hypogonadism, none of the patients had a pretreatment LH concentration above the upper limit. Fifteen percent, however, had pretreatment concentrations below the normal limit. The unclassified patients showed comparatively rapid LH concentration decreases in all treatment groups as shown in FIG. 13(d) and Table 16(d).

TABLE 16(d)

Concentrations for LH (mIU/mL) on Each of the Observation Days for Patients Having Unknown-Related Hypogonadism (Summary of Mean ± SD)

|  | N | 5 g/day | N | 10 g/day | N | T-patch |
| --- | --- | --- | --- | --- | --- | --- |
| Day 0 | 17 | 1.8 ± 1.2 | 26 | 2.5 ± 1.5 | 21 | 2.5 ± 1.5 |
| Day 30 | 17 | 0.3 ± 0.3 | 26 | 0.3 ± 0.3 | 21 | 1.3 ± 1.3 |
| Day 60 | 17 | 0.4 ± 0.5 | 26 | 0.3 ± 0.3 | 18 | 1.2 ± 1.4 |
| Day 90 | 17 | 0.5 ± 0.5 | 26 | 0.3 ± 0.4 | 18 | 1.0 ± 1.4 |
| Day 120 | 17 | 0.4 ± 0.4 | 26 | 0.4 ± 0.5 | 12 | 1.2 ± 1.1 |
| Day 150 | 17 | 0.8 ± 1.1 | 23 | 0.3 ± 0.4 | 13 | 1.1 ± 1.1 |
| Day 180 | 15 | 0.3 ± 0.4 | 25 | 0.4 ± 0.4 | 11 | 1.5 ± 1.3 |

(3) Summary: LH and FSH

Patients receiving AndroGel® or the testosterone patch achieve "hormonal steady state" only after long-term treatment. Specifically, data involving FSH and LH show that these hormones do not achieve steady-state until many weeks after treatment. Because testosterone concentrations are negatively inhibited by FSH and LH, testosterone levels do not achieve true steady state until these other hormones also achieve steady state. However, because these hormones regulate only endogenous testosterone (which is small to begin with in hypogonadal men) in an intact feedback mechanism (which may not be present depending on the cause of hypogonadism), the level of FSH and/or LH may have little effect on the actual testosterone levels achieved. The net result is that the patients do not achieve a "hormonal steady state" for testosterone even though the $C_{avg}$, $C_{min}$, and $C_{max}$ for testosterone remains relatively constant after a few days of treatment.

2. Bone Mineral Density ("BMD") and Similar Markers a. BMD

BMD was assessed by dual energy X-ray absorptiometry ("DEXA") using Hologic QDR 2000 or 4500 A (Hologic, Waltham, Mass.) on days 0 and 180 in the lumbar spine and left hip regions. BMD of spine was calculated as the average of BMD at L1 to L4. BMD of the left hip, which included Ward's triangle, was calculated by the average of BMD from neck, trochanter, and intertrochanter regions. The scans were centrally analyzed and processed at Hologic. BMD assessments were performed at 13 out of the 16 centers (206 out of 227 subjects) because of the lack of the specific DEXA equipment at certain sites.

Figure 14A:
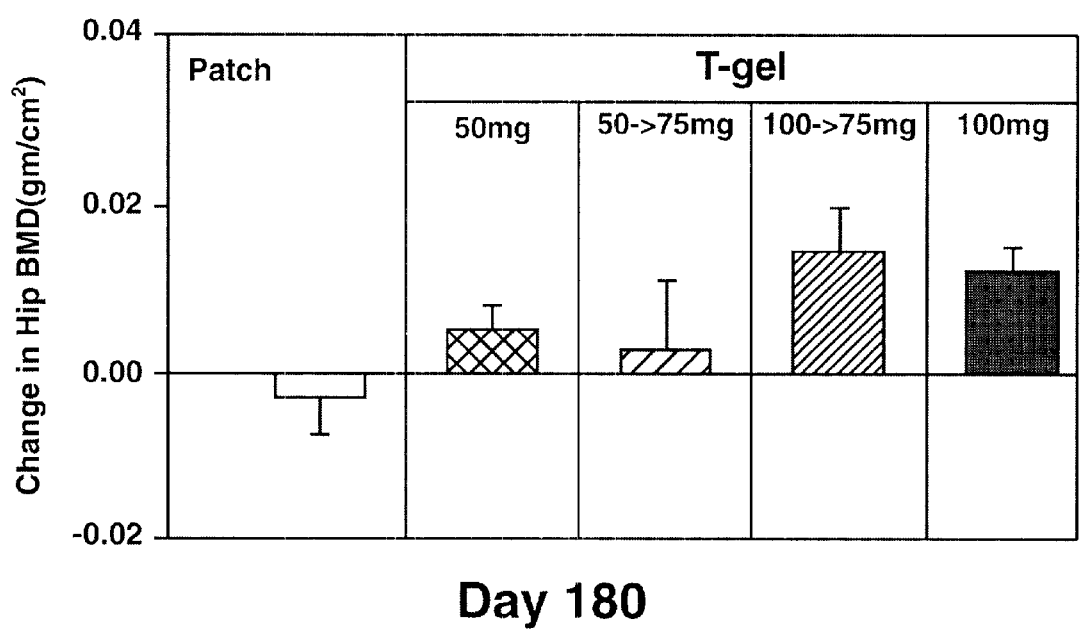
FIG. 14(a) is a bar graph showing the change in hip BMD for hypogonadal men after 180 days of treatment with 5.0 g/day of AndroGel®, 7.5 g/day of AndroGel®, 10.0 g/day of AndroGel®, or the testosterone patch.
Figure 14B:
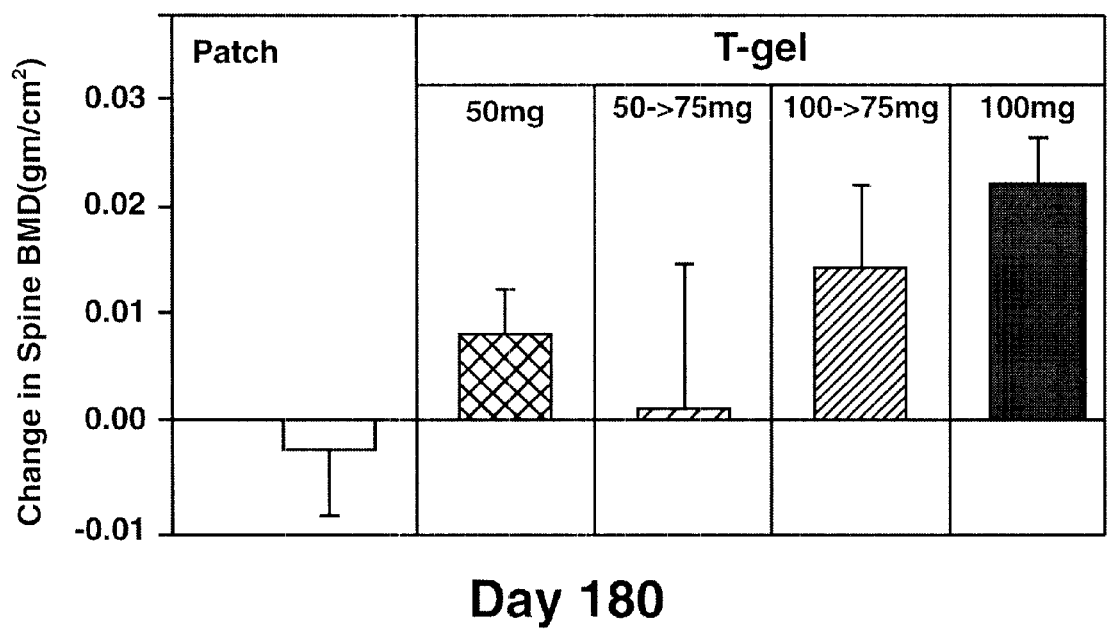
FIG. 14(b) is a bar graph showing the change in spine BMD for hypogonadal men after 180 days of treatment with 5.0 g/day of AndroGel®, 7.5 g/day of AndroGel®, 10.0 g/day of AndroGel®, or the testosterone patch

Table 17 and FIGS. 14(*a*)–14(*b*) show that before treatment, the BMD of the hip or the spine was not different among the three treatment groups. Significant increases in BMD occurred only in subjects in the AndroGel® 10.0 g/day group and those who switched from AndroGel® 10.0 to 7.5 g/day groups. The increases in BMD were about 1% in the hip and 2% in the spine during the six-month period. Average increases in BMD of 0.6% and 1% in the hip and spine were seen in those receiving 5.0 g/day of AndroGel® but no increase was observed in the testosterone patch group.

The baseline hip and spine BMD and the change in BMD on day 180 were not significantly correlated with the average serum testosterone concentration on day 0. The changes in BMD in the hip or spine after testosterone replacement were not significantly different in subjects with hypogonadism due to primary, secondary, aging, or unclassified causes; nor were they different between naive and previously testosterone replaced subjects. The change in BMD in the spine was negatively correlated with baseline BMD values, indicating that the greatest increase in BMD occurred in subjects with the lowest initial BMD. The increase in BMD in the hip (but not in the spine) after testosterone treatment was correlated with the change in serum testosterone levels.

b. Bone Osteoblastic Activity Markers

The results described above are supported by measurements of a number of serum and urine markers of bone formation. Specifically, the mean concentrations of the serum markers (PTH, SALP, osteocalcin, type I procollagen) generally increase during treatment in all treatment groups. In addition, the ratios of two urine markers of bone formation (N-telopeptide/creatinine ratio and calcium/creatinine ratio) suggests a decrease in bone resorption.

(1) PTH (Parathyroid or Calciotropic Hormone)

Serum intact PTH was measured by two site immunoradiometric assay ("IRMA") kits from Nichol's Institute (San Juan Capistrano, Calif.). The LLC for the PTH assay was 12.5 ng/L. The intra- and inter-assay coefficients of variation were 6.9 and 9.6%, respectively. The UCLA-Harbor Medical Center has reported previously that the normal male adult range of PTH is 6.8 to 66.4 ng/L.

Figure 15:
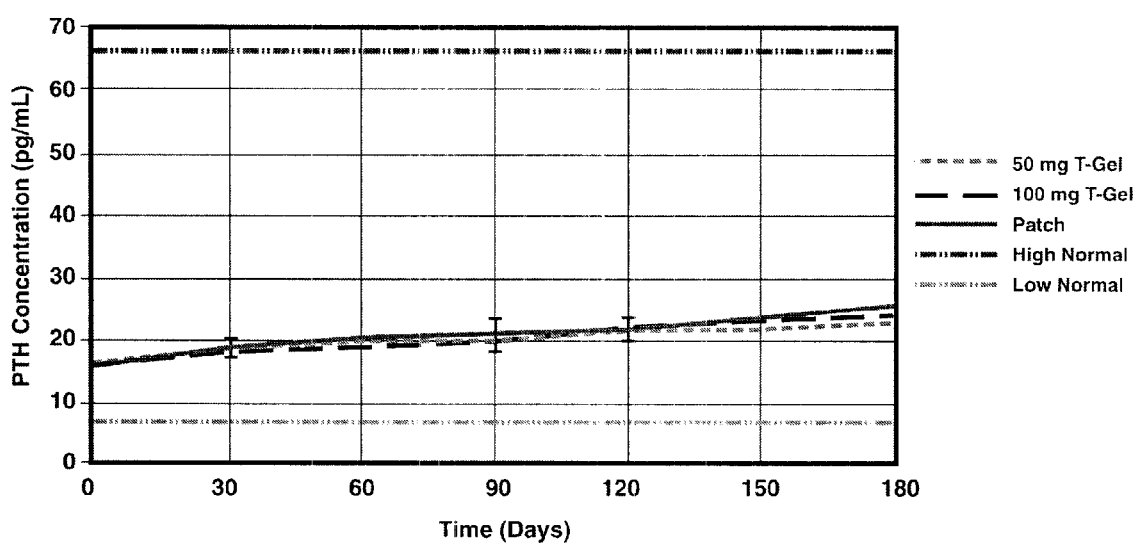
FIG. 15 is a graph showing PTH concentrations on days 0 through 180 for hypogonadal men receiving either 5.0 g/day of AndroGel®, 10.0 g/day of AndroGel®, or the testosterone patch (by initial treatment group).

Table 18 provides the PTH concentrations over the 180-day study. FIG. 15 shows that the mean serum PTH levels were within the normal male range in all treatment groups at baseline. Statistically significant increases in serum PTH were observed in all subjects as a group at day 90 without inter-group differences. These increases in serum PTH were maintained at day 180 in all three groups.

TABLE 17

BMD Concentrations on Day 0 and Day 180 by Final Treatment Group Mean (± SD)

| Final Treatment Group | N | Day 0 | N | Day 180 | N | % Change from Day 0 to Day 180 |
|---|---|---|---|---|---|---|
| Hip | | | | | | |
| 5.0 g/day T-gel | 50 | 1.026 ± 0.145 | 41 | 1.022 ± 0.145 | 41 | 0.7 ± 2.1 |
| 5.0 to 7.5 g/day T-gel | 16 | 1.007 ± 0.233 | 15 | 1.011 ± 0.226 | 15 | 1.0 ± 4.9 |
| 10.0 to 7.5 g/day T-gel | 20 | 1.002 ± 0.135 | 19 | 1.026 ± 0.131 | 19 | 1.3 ± 2.4 |
| 10.0 g/day T-gel | 53 | 0.991 ± 0.115 | 44 | 0.995 ± 0.130 | 44 | 1.1 ± 1.9 |
| T-Patch | 67 | 0.982 ± 0.166 | 37 | 0.992 ± 0.149 | 37 | −0.2 ± 2.9 |
| Spine | | | | | | |
| 5.0 g/day T-gel | 50 | 1.066 ± 0.203 | 41 | 1.072 ± 0.212 | 41 | 1.0 ± 2.9 |
| 5.0 to 7.5 g/day T-gel | 16 | 1.060 ± 0.229 | 15 | 1.077 ± 0.217 | 15 | 0.4 ± 5.5 |
| 10.0 to 7.5 g/day T-gel | 19 | 1.049 ± 0.175 | 19 | 1.067 ± 0.175 | 18 | 1.4 ± 3.2 |
| 10.0 g/day T-gel | 53 | 1.037 ± 0.126 | 44 | 1.044 ± 0.124 | 44 | 2.2 ± 3.1 |
| T-Patch | 67 | 1.058 ± 0.199 | 36 | 1.064 ± 0.205 | 36 | −0.2 ± 3.4 |

Note: Day 0 and Day 180 are arithmetic means, while percent change is a geometric mean.

TABLE 18

PTH Concentrations on Each of the Observation Days by Final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 16.31 ± 8.81 | 20 | 17.70 ± 9.66 | 20 | 18.02 ± 8.18 | 58 | 14.99 ± 6.11 | 75 | 15.60 ± 6.57 |
| Day 30 | 49 | 17.91 ± 10.36 | 20 | 18.33 ± 8.02 | 20 | 17.45 ± 5.67 | 58 | 18.04 ± 8.95 | 72 | 18.33 ± 10.92 |

TABLE 18-continued

| | | 5 g/day T-gel | | 5 => 7.5 g/day T-gel | | 10 => 7.5 g/day T-gel | | 10 g/day T-gel | | T-Patch |
|---|---|---|---|---|---|---|---|---|---|---|
| | N | | N | | N | | N | | N | |
| Day 90 | 47 | 21.32 ± 11.47 | 20 | 21.25 ± 10.96 | 19 | 17.10 ± 6.04 | 54 | 20.01 ± 9.77 | 66 | 21.45 ± 13.71 |
| Day 120 | 46 | 21.19 ± 11.42 | 19 | 21.42 ± 13.20 | 20 | 19.62 ± 9.96 | 50 | 22.93 ± 12.57 | 46 | 21.07 ± 11.44 |
| Day 180 | 46 | 22.85 ± 12.89 | 19 | 21.34 ± 11.08 | 19 | 21.02 ± 10.66 | 51 | 25.57 ± 15.59 | 46 | 25.45 ± 16.54 |

(2) SALP

SALP was quantitated by IRMA using reagents supplied by Hybritech (San Diego, Calif.). The LLQ for the SALP assay was 3.8 µg/L.; and the intra- and inter-assay precision coefficients were 2.9 and 6.5%, respectively. The UCLA-Harbor Medical Center reported that the adult normal male concentration of SALP ranges from 2.4 to 16.6 µg/L.

Figure 16:
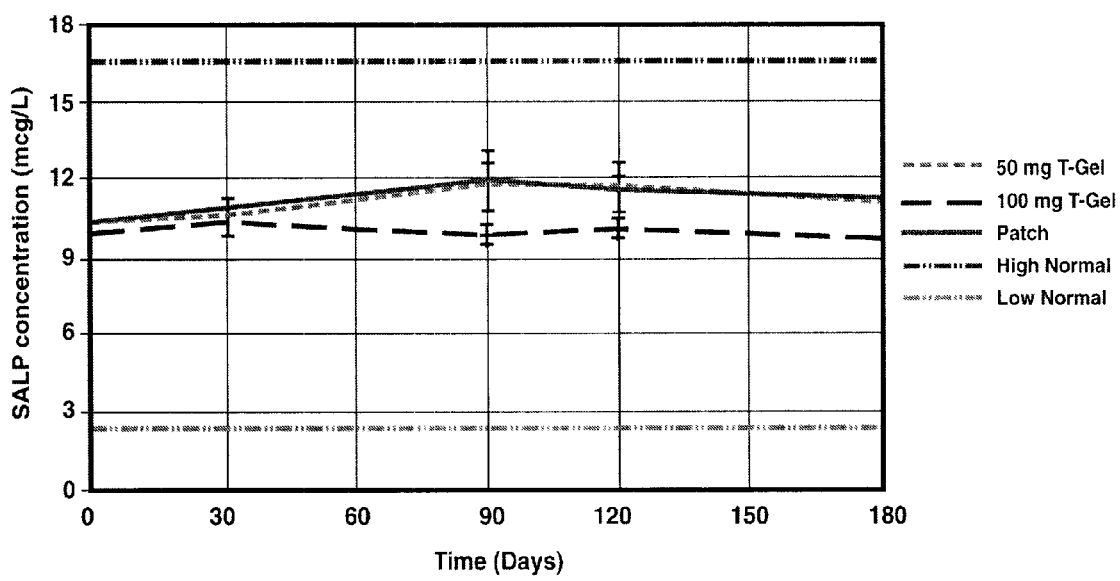
FIG. 16 is a graph showing SALP concentrations on days 0 through 180 for hypogonadal men receiving either 5.0 g/day of AndroGel®, 10.0 g/day of AndroGel®, or the testosterone patch (by initial treatment group).

The pretreatment SALP concentrations were within the normal range. FIG. 16 and Table 19 show that SALP levels increased with testosterone treatment in the first 90 days and reached statistical difference in the testosterone patch group. Thereafter serum SALP plateaued in all treatment groups.

TABLE 19

SALP Concentrations on Each of the Observation Days by Final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 9.96 ± 5.61 | 20 | 12.36 ± 4.62 | 20 | 10.48 ± 3.68 | 58 | 9.80 ± 3.57 | 76 | 10.44 ± 3.77 |
| Day 30 | 49 | 10.20 ± 6.77 | 20 | 11.38 ± 4.09 | 20 | 11.83 ± 4.32 | 58 | 9.93 ± 3.88 | 71 | 10.86 ± 3.75 |
| Day 90 | 47 | 11.64 ± 7.98 | 20 | 11.97 ± 5.03 | 20 | 10.97 ± 3.18 | 55 | 9.56 ± 3.12 | 65 | 11.99 ± 9.36 |
| Day 120 | 46 | 11.71 ± 7.85 | 19 | 12.12 ± 5.25 | 20 | 11.61 ± 2.58 | 48 | 9.63 ± 3.58 | 45 | 11.63 ± 4.72 |
| Day 180 | 45 | 11.12 ± 7.58 | 19 | 11.67 ± 5.35 | 19 | 11.22 ± 3.44 | 51 | 9.19 ± 2.42 | 46 | 11.47 ± 3.77 |

(3) Osteocalcin

Serum osteocalcin was measured by an IRMA from Immutopics (San Clemente, Calif.). The LLQ was 0.45 µg/L. The intra- and inter-assay coefficients were 5.6 and 4.4%, respectively. The UCLA-Harbor Medical Center reports that the normal male adult range for the osteocalcin assay ranges from 2.9 to 12.7 µg/L.

Figure 17:
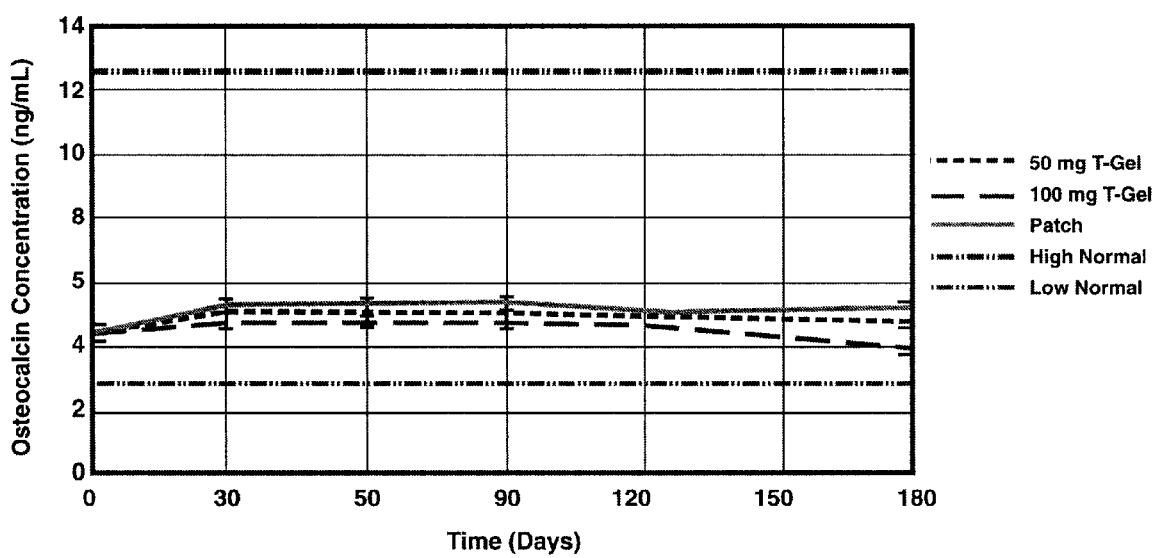
FIG. 17 is a graph showing the osteocalcin concentrations on days 0 through 180 for hypogonadal men receiving either 5.0 g/day of AndroGel®, 10.0 g/day of AndroGel®, or the testosterone patch (by initial treatment group).

As shown in FIG. 17 and Table 20, the baseline mean serum osteocalcin levels were within the normal range in all treatment groups. During the first 90-day treatment, mean serum osteocalcin increased with testosterone replacement in all subjects as a group without significant differences between the groups. With continued treatment serum osteocalcin either plateaued or showed a decrease by day 180.

TABLE 20

Osteocalcin Concentrations on Each of the Observation Days by Final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 4.62 ± 1.55 | 20 | 5.01 ± 2.03 | 20 | 4.30 ± 1.28 | 58 | 4.58 ± 1.92 | 76 | 4.53 ± 1.54 |
| Day 30 | 49 | 4.63 ± 1.65 | 20 | 5.35 ± 2.06 | 20 | 4.48 ± 1.72 | 58 | 4.91 ± 2.08 | 72 | 5.17 ± 1.61 |
| Day 90 | 47 | 4.91 ± 2.15 | 20 | 5.29 ± 1.87 | 19 | 4.76 ± 1.50 | 55 | 4.83 ± 2.13 | 66 | 5.18 ± 1.53 |
| Day 120 | 46 | 4.95 ± 1.97 | 18 | 4.97 ± 1.60 | 20 | 4.71 ± 1.39 | 49 | 4.61 ± 2.01 | 47 | 4.98 ± 1.87 |
| Day 180 | 45 | 4.79 ± 1.82 | 19 | 4.59 ± 1.54 | 19 | 4.47 ± 1.49 | 51 | 3.76 ± 1.60 | 46 | 5.15 ± 2.18 |

(4) Type I Procollagen

Serum type I procollagen was measured using a RIA kit from Incstar Corp (Stillwater, Minn.). The LLQ of the procollagen assay was 5 μg/L, and the intra- and inter-assay precisions were 6.6 and 3.6%, respectively. The UCLA-Harbor Medical Center reports that the normal adult male concentration of type I procollagen ranges from 56 to 310 μg/L.

Figure 18:
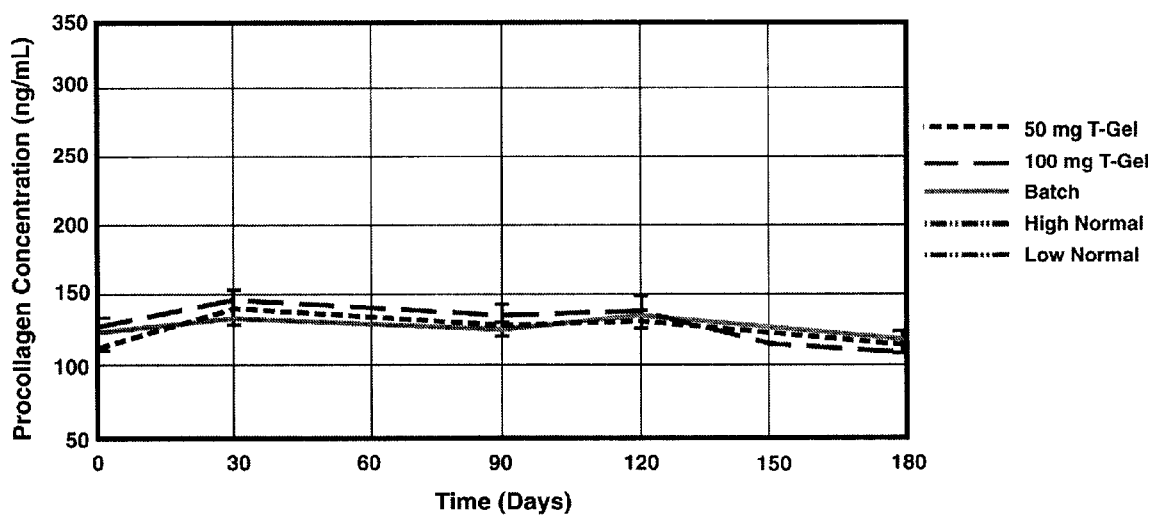
FIG. 18 is a graph showing the type I procollagen concentrations on days 0 through 180 for hypogonadal men receiving either 5.0 g/day of AndroGel®, 10.0 g/day of AndroGel®, or the testosterone patch (by initial treatment group).

FIG. 18 and Table 21 show that serum procollagen generally followed the same pattern as serum osteocalcin. At baseline the mean levels were similar and within the normal range in all treatment groups. With transdermal treatment, serum procollagen increased significantly in all subjects as a group without treatment group differences. The increase in procollagen was highest on day 30 and then plateaued until day 120. By day 180, the serum procollagen levels returned to baseline levels.

the UCLA-Harbor Medical Center, creatinine levels in normal adult men range from 2.1 mM to 45.1 mM. The sensitivity of the assay for calcium was 0.7 mg/dL and the LLQ was 0.7 mg/dL. The normal range for urine calcium is 0.21 mM to 7.91 mM.

N-telopeptides were measured by an enzyme-linked immunosorbant assay ("ELISA") from Ostex (Seattle, Wash.). The LLQ for the N-telopeptide assay was 5 nM bone collagen equivalent ("BCE"). The intra- and inter-assay had a precision of 4.6 and 8.9%, respectively. The normal range for the N-telopeptide assay was 48–2529 nM BCE. Samples containing low or high serum/urine bone marker levels were reassayed after adjusting sample volume or dilution to ensure all samples would be assayed within acceptable precision and accuracy.

Figure 19:
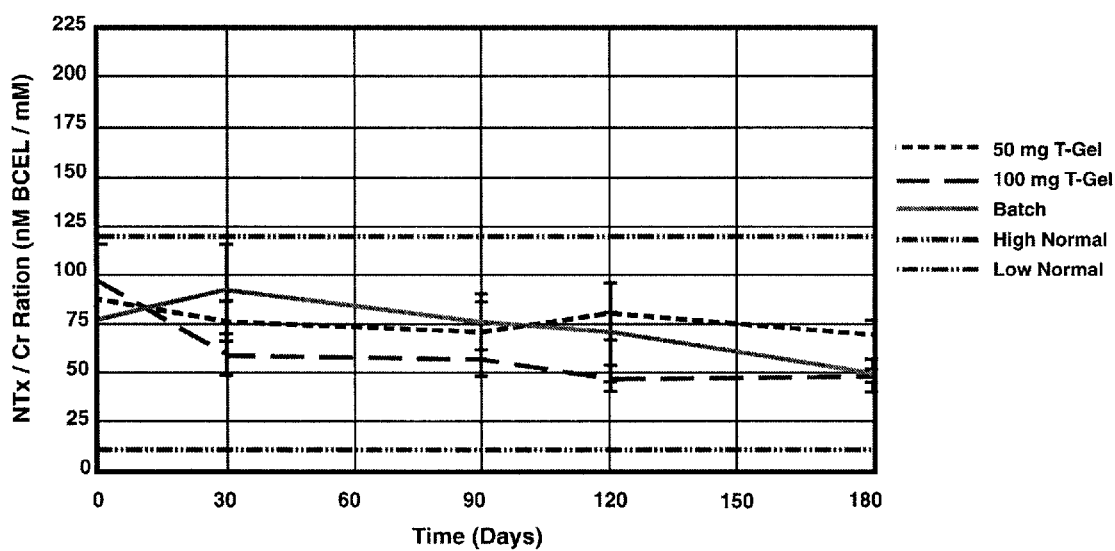
FIG. 19 is a graph showing the N-telopeptide/Cr ratio on days 0 through 180 for hypogonadal men receiving either 5.0 g/day of AndroGel®, 10.0 g/day of AndroGel®, or the testosterone patch (by initial treatment group).

The normal adult male range for the N-telopeptide/Cr ratio is 13 to 119 nM BCE/nM Cr. As shown in FIG. 19 and

TABLE 21

Procollagen Concentrations on Each of the Observation Days by Final Treatment Group (Mean ± SD)

|  | 5 g/day | | 5 => 7.5 g/day | | 10 => 7.5 | | 10 g/day | | | |
|---|---|---|---|---|---|---|---|---|---|---|
|  | N | T-gel | N | T-gel | N | g/day T-gel | N | T-gel | N | T-Patch |
| Day 0 | 53 | 115.94 ± 43.68 | 20 | 109.27 ± 32.70 | 20 | 120.93 ± 28.16 | 58 | 125.33 ± 57.57 | 76 | 122.08 ± 51.74 |
| Day 30 | 49 | 141.09 ± 64.02 | 20 | 141.41 ± 77.35 | 20 | 147.25 ± 49.85 | 58 | 149.37 ± 60.61 | 71 | 139.26 ± 59.12 |
| Day 90 | 47 | 137.68 ± 68.51 | 20 | 129.02 ± 60.20 | 29 | 144.60 ± 58.20 | 55 | 135.59 ± 51.54 | 66 | 130.87 ± 49.91 |
| Day 120 | 46 | 140.07 ± 81.48 | 19 | 133.61 ± 54.09 | 20 | 139.00 ± 64.96 | 50 | 128.48 ± 45.56 | 46 | 130.39 ± 42.22 |
| Day 180 | 45 | 119.78 ± 49.02 | 19 | 108.78 ± 35.29 | 19 | 123.51 ± 39.30 | 51 | 108.52 ± 38.98 | 45 | 120.74 ± 56.10 | c. Urine Bone Turnover Markers: N-telopeptide/Cr and Ca/Cr Ratios

Urine calcium and creatinine were estimated using standard clinical chemistry procedures by an autoanalyzer operated by the UCLA-Harbor Pathology Laboratory. The procedures were performed using the COBAS MIRA automated chemistry analyzer system manufactured by Roche Diagnostics Systems. The sensitivity of the assay for creatinine was 8.9 mg/dL and the LLQ was 8.9 mg/dL. According to Table 22, urinary N-telopeptide/Cr ratios were similar in all three treatment groups at baseline but decreased significantly in the AndroGel® 10.0 g/day group but not in the AndroGel® 5.0 g/day or testosterone patch group during the first 90 days of treatment. The decrease was maintained such that urinary N-telopeptide/Cr ratio remained lower than baseline in AndroGel® 10.0 g/day and in those subjects adjusted to 7.5 g/day from 10.0 g/day group at day 180. This ratio also decreased in the testosterone patch treatment group by day 180.

TABLE 22

N-Telopeptide/Cr Ratio on Each of the Observation Days by Initial Treatment Group (Mean ± SD)

| Initial Treatment Group | 5.0 g/day | | 10.0 g/day | | | | Across-group |
|---|---|---|---|---|---|---|---|
|  | N | T-gel | N | T-gel | N | T-Patch | p-value |
| Day 0 | 71 | 90.3 ± 170.3 | 75 | 98.0 ± 128.2 | 75 | 78.5 ± 82.5 | 0.6986 |
| Day 30 | 65 | 74.6 ± 79.3 | 73 | 58.4 ± 66.4 | 66 | 91.6 ± 183.6 | 0.3273 |
| Day 90 | 62 | 70.4 ± 92.6 | 73 | 55.2 ± 49.1 | 63 | 75.0 ± 113.5 | 0.5348 |
| Day 120 | 35 | 78.8 ± 88.2 | 36 | 46.6 ± 36.4 | 21 | 71.2 ± 108.8 | 0.2866 |
| Day 180 | 64 | 68.2 ± 81.1 | 70 | 46.9 ± 43.1 | 47 | 49.4 ± 40.8 | 0.2285 |

Figure 20:
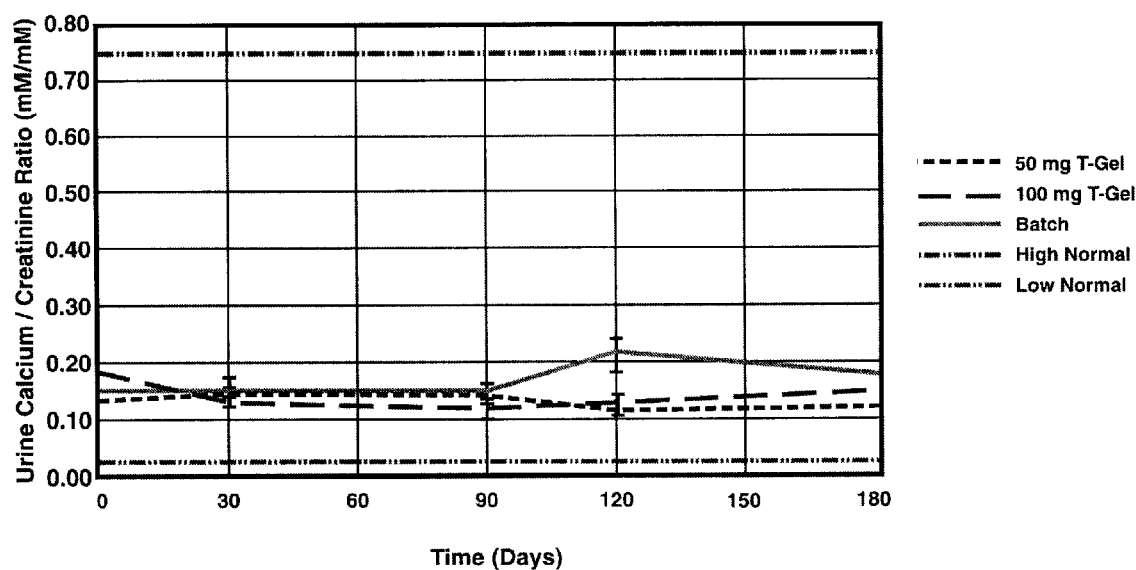
FIG. 20 is a graph showing the Ca/Cr ratio on days 0 through 180 for hypogonadal men receiving either 5.0 g/day of AndroGel®, 10.0 g/day of AndroGel®, or the testosterone patch (by initial treatment group).

The normal range for Ca/Cr ratio is 0.022 to 0.745 mM/mM. FIG. 20 shows no significant difference in baseline urinary Ca/Cr ratios in the three groups. With transdermal testosterone replacement therapy, urinary Ca/Cr ratios did not show a significant decrease in any treatment group at day 90. With continued testosterone replacement to day 180, urinary Ca/Cr showed marked variation without significant changes in any treatment groups.

TABLE 23

Ca/Cr Ratio on Each of the Observation Days by Initial Treatment Group (Mean ± SD)

| Initial Treatment Group | N | 5.0 g/day T-gel | N | 10.0 g/day T-gel | N | T-Patch | Across-group p-value |
|---|---|---|---|---|---|---|---|
| Day 0 | 71 | 0.150 ± 0.113 | 75 | 0.174 ± 0.222 | 75 | 0.158 ± 0.137 | 0.6925 |
| Day 30 | 65 | 0.153 ± 0.182 | 73 | 0.128 ± 0.104 | 66 | 0.152 ± 0.098 | 0.3384 |
| Day 90 | 63 | 0.136 ± 0.122 | 73 | 0.113 ± 0.075 | 63 | 0.146 ± 0.099 | 0.2531 |
| Day 120 | 36 | 0.108 ± 0.073 | 36 | 0.117 ± 0.090 | 21 | 0.220 ± 0.194 | 0.0518 |
| Day 180 | 64 | 0.114 ± 0.088 | 70 | 0.144 ± 0.113 | 47 | 0.173 ± 0.108 | 0.0398 |

Interestingly, the change in Ca/Cr ratio from baseline at day 90 was inversely related to the baseline Ca/Cr ratios. Similarly, the change in urine N-telopeptide/Cr ratio was also inversely proportional to the baseline N-telopeptide/Cr ratio ($r=-0.80$, $p=0.0001$). Thus subjects with the highest bone resorption markers at baseline showed the largest decreases of these markers during transdermal testosterone replacement. The decreases in urinary bone resorption markers were most prominent in subjects who had highest baseline values, suggesting that hypogonadal subjects with the most severe metabolic bone disease responded most to testosterone replacement therapy.

d. Serum Calcium

Serum calcium showed no significant inter-group differences at baseline, nor significant changes after testosterone replacement. Serum calcium levels showed insignificant changes during testosterone replacement.

3. Libido, Sexual Performance, and Mood

Sexual function and mood were assessed by questionnaires the patients answered daily for seven consecutive days before clinic visits on day 0 and on days 30, 60, 90, 120, 150, and 180 days during gel and patch application. The subjects recorded whether they had sexual day dreams, anticipation of sex, flirting, sexual interaction (e.g., sexual motivation parameters) and orgasm, erection, masturbation, ejaculation, intercourse (e.g., sexual performance parameters) on each of the seven days. The value was recorded as 0 (none) or 1 (any) for analyses and the number of days the subjects noted a parameter was summed for the seven-day period. The average of the four sexual motivation parameters was taken as the sexual motivation score and that of the five sexual motivation parameters as the sexual motivation mean score (0 to 7). The subjects also assessed their level of sexual desire, sexual enjoyment, and satisfaction of erection using a seven-point Likert-type scale (0 to 7) and the percent of full erection from 0 to 100%. The subjects rated their mood using a 0 to 7 score. The parameters assessed included positive mood responses: alert, friendly, full of energy, well/good feelings and negative mood responses: angry, irritable, sad, tired, nervous. Weekly average scores were calculated. The details of this questionnaire had been described previously and are fully incorporated by reference. See Wang et al., *Testosterone Replacement Therapy Improves Mood in Hypogonadal Men—A Clinical Research Center Study*, 81 J. CLINICAL ENDOCRINOLOGY & METABOLISM 3578–3583 (1996).

a. Libido

Figure 21A:
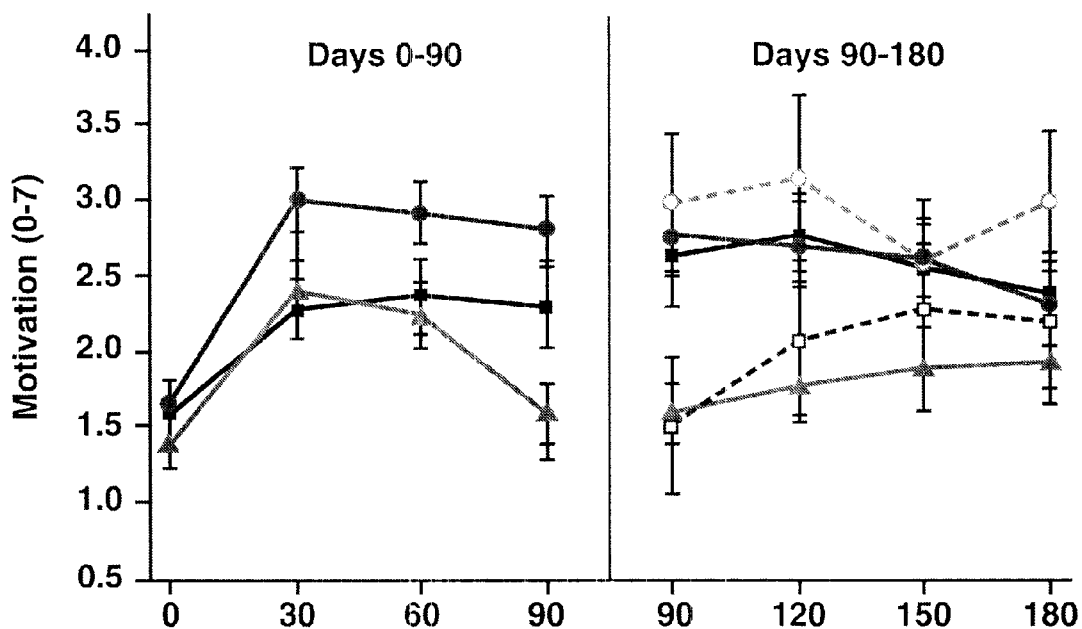
FIG. 21(a) is a graph showing sexual motivation scores on days 0 through 180 for hypogonadal men receiving either 5.0 g/day of AndroGel®, 7.5 g/day of Androgel®, 10.0 g/day of AndroGel®, or the testosterone patch.
Figure 21B:
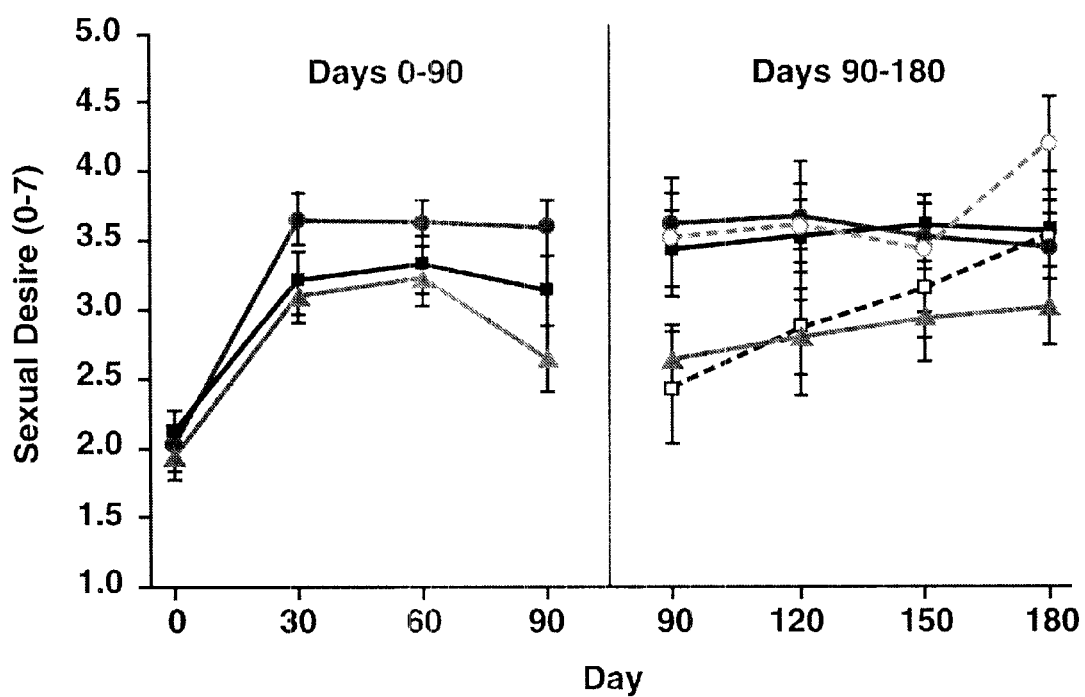
FIG. 21(b) is a graph showing overall sexual desire scores on days 0 through 180 for hypogonadal men receiving either 5.0 g/day of AndroGel®, 7.5 g/day of Androgel®, 10.0 g/day of AndroGel®, or the testosterone patch.
Figure 21C:
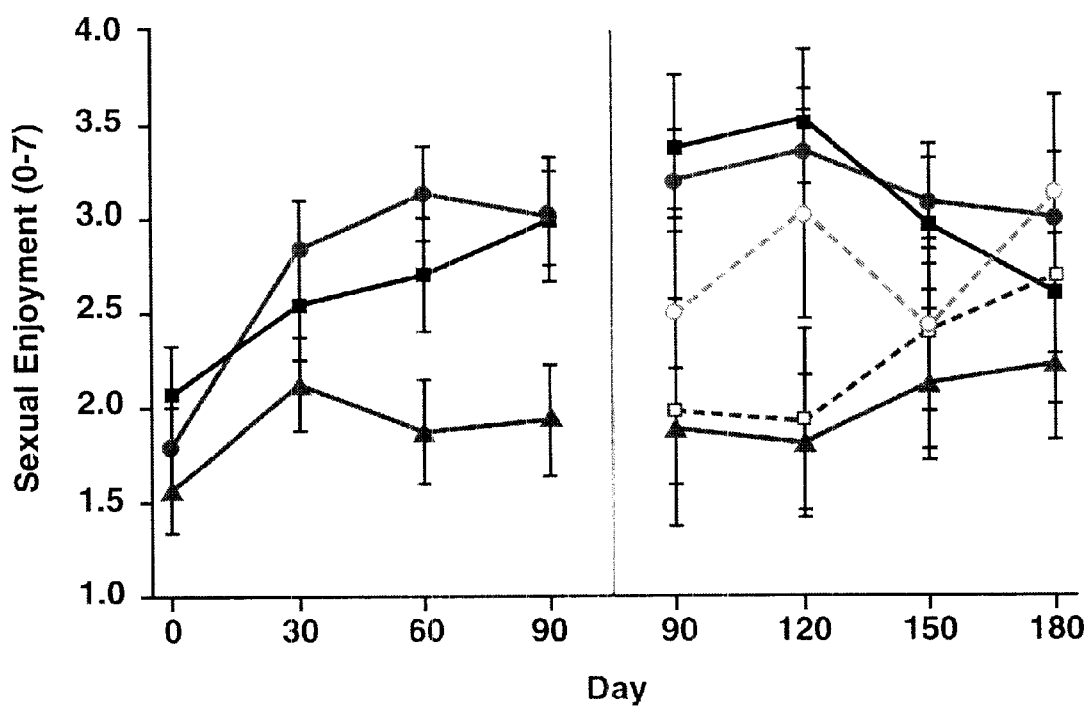
FIG. 21(c) is a graph showing sexual enjoyment (with a partner) scores on days 0 through 180 for hypogonadal men receiving either 5.0 g/day of AndroGel®, 7.5 g/day of Androgel®, 10.0 g/day of AndroGel®, or the testosterone patch.

As shown in FIG. 21(*a*), at baseline, sexual motivation was the same in all treatment groups. After transdermal testosterone treatment, overall sexual motivation showed significant improvement. The change in the summary score from baseline, however, was not different among the three treatment groups.

Libido was assessed from responses on a linear scale of: (1) overall sexual desire, (2) enjoyment of sexual activity without a partner, and (3) enjoyment of sexual activity with a partner. As shown in FIG. 21(*b*) and Table 24, as a group, overall sexual desire increased after transdermal testosterone treatment without inter-group difference. Sexual enjoyment with and without a partner (FIG. 21(*c*) and Tables 25 and 26) also increased as a group.

Similarly the sexual performance score improved significantly in all subjects as a group. The improvement in sexual performance from baseline values was not different between transdermal preparations.

TABLE 24

Overall Sexual Desire Changes From Day 0 to Day 180 by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 69 | 2.1 ± 1.6 | 63 | 3.5 ± 1.6 | 60 | 1.4 ± 1.9 | 0.0001 |
| 10.0 g/day T-gel | 77 | 2.0 ± 1.4 | 68 | 3.6 ± 1.6 | 67 | 1.5 ± 1.9 | 0.0001 |
| T-Patch | 72 | 2.0 ± 1.6 | 47 | 3.1 ± 1.9 | 45 | 1.6 ± 2.1 | 0.0001 |
| Across-Groups p-value | | 0.8955 | | 0.2247 | | 0.8579 | |

TABLE 25

Level of Sexual Enjoyment Without a Partner
Changes From Day 0 to Day 180
by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 60 | 1.5 ± 1.9 | 51 | 1.9 ± 1.9 | 44 | 0.8 ± 1.4 | 0.0051 |
| 10.0 g/day T-gel | 63 | 1.2 ± 1.4 | 53 | 2.2 ± 1.9 | 48 | 1.1 ± 1.6 | 0.0001 |
| T-Patch | 66 | 1.4 ± 1.8 | 44 | 2.2 ± 2.3 | 40 | 1.0 ± 1.9 | 0.0026 |
| Across-Groups p-value | | 0.6506 | | 0.7461 | | 0.6126 | |

TABLE 26

Level of Sexual Enjoyment With a Partner
Change From Day 0 to Day 180
by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 64 | 2.1 ± 2.1 | 55 | 2.6 ± 2.2 | 48 | 0.4 ± 2.2 | 0.0148 |
| 10.0 g/day T-gel | 66 | 1.8 ± 1.7 | 58 | 3.0 ± 2.2 | 52 | 1.0 ± 2.3 | 0.0053 |
| T-Patch | 61 | 1.5 ± 1.7 | 40 | 2.2 ± 2.4 | 35 | 0.7 ± 2.3 | 0.1170 |
| Across-Groups p-value | | 0.2914 | | 0.1738 | | 0.3911 | | b. Sexual Performance

Figure 22A:
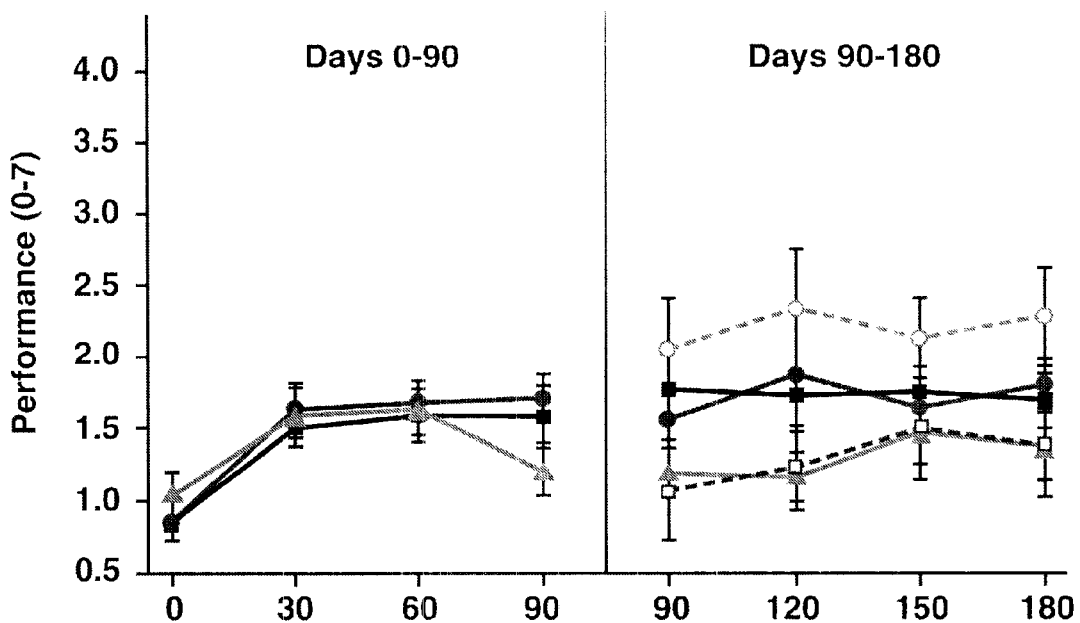
FIG. 22(a) is a graph showing sexual performance scores on days 0 through 180 for hypogonadal men receiving either
Figure 22B:
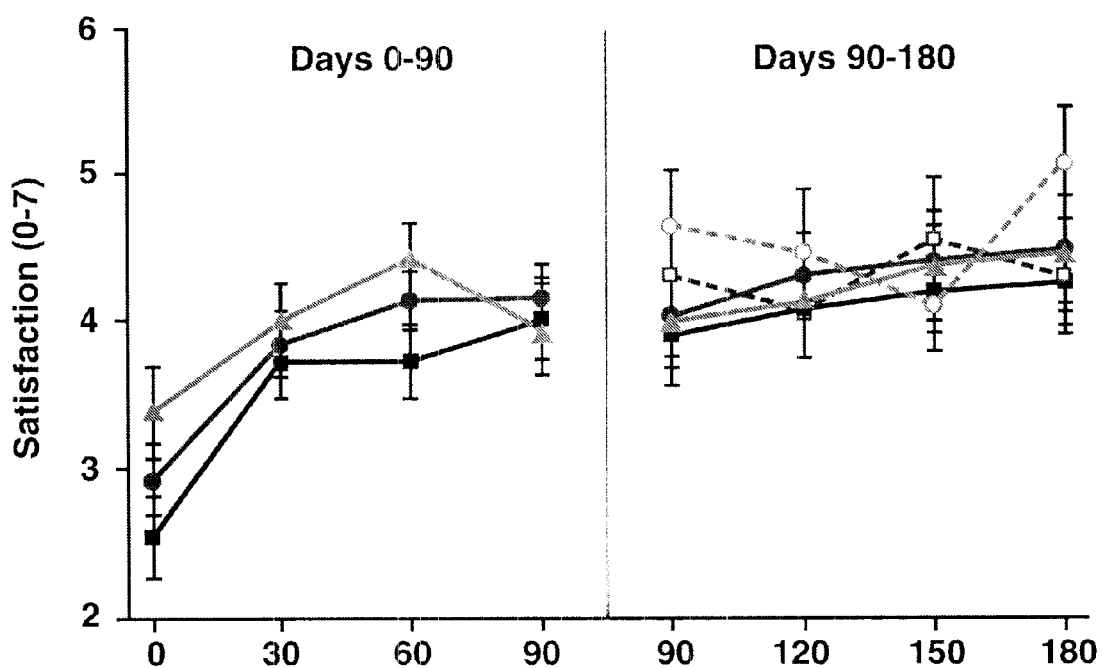
FIG. 22(b) is a graph showing erection satisfaction performance scores on days 0 through 180 for hypogonadal men receiving either 5.0 g/day of AndroGel®, 7.5 g/day of Androgel®, 10.0 g/day of AndroGel®, or the testosterone patch.
Figure 22C:
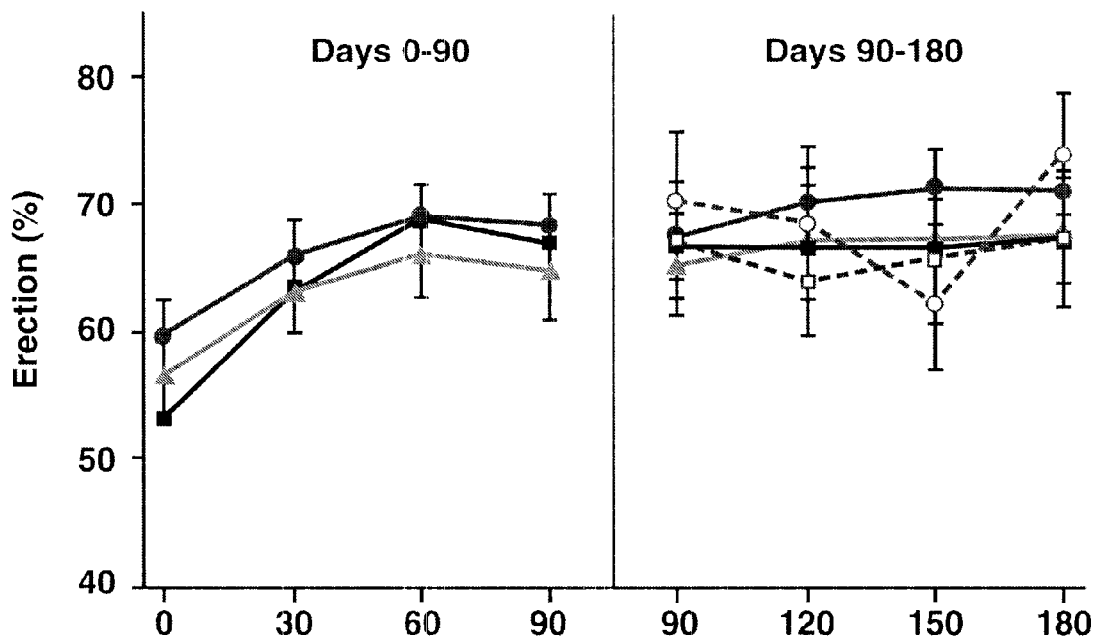
FIG. 22(c) is a graph showing percent erection scores on days 0 through 180 for hypogonadal men receiving either 5.0 g/day of AndroGel®, 7.5 g/day of Androgel®, 10.0 g/day of AndroGel®, or the testosterone patch.

FIG. 22(a) shows that while all treatment groups had the same baseline sexual performance rating, the rating improved with transdermal testosterone treatment in all groups. In addition, as a group, the subjects' self-assessment of satisfaction of erection (FIG. 22(b) and Table 27) and percent full erection (FIG. 22(c) and Table 28) were also increased with testosterone replacement without significant differences between groups.

The improvement in sexual function was not related to the dose or the delivery method of testosterone. Nor was the improvement related to the serum testosterone levels achieved by the various testosterone preparations. The data suggest that once a threshold (serum testosterone level probably at the low normal range) is achieved, normalization of sexual function occurs. Increasing serum testosterone levels higher to the upper normal range does not further improve sexual motivation or performance.

TABLE 27

Satisfaction with Duration of Erection
Change From Day 0 to Day 180
by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 55 | 2.5 ± 2.1 | 57 | 4.3 ± 1.8 | 44 | 1.9 ± 2.0 | 0.0001 |
| 10.0 g/day T-gel | 64 | 2.9 ± 1.9 | 58 | 4.5 ± 1.7 | 53 | 1.5 ± 2.0 | 0.0001 |
| T-Patch | 45 | 3.4 ± 2.1 | 34 | 4.5 ± 2.0 | 20 | 1.3 ± 2.1 | 0.0524 |
| Across-Groups p-value | | 0.1117 | | 0.7093 | | 0.5090 | |

TABLE 28

Percentage of Full Erection
Change From Day 0 to Day 180
by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 53 | 53.1 ± 24.1 | 57 | 67.4 ± 22.5 | 43 | 18.7 ± 22.1 | 0.0001 |
| 10.0 g/day T-gel | 62 | 59.6 ± 22.1 | 59 | 72.0 ± 20.2 | 52 | 10.4 ± 23.4 | 0.0001 |
| T-Patch | 47 | 56.5 ± 24.7 | 33 | 66.7 ± 26.7 | 19 | 12.7 ± 20.3 | 0.0064 |
| Across-Groups p-value | | 0.3360 | | 0.4360 | | 0.1947 | | c. Mood

Figure 23A:
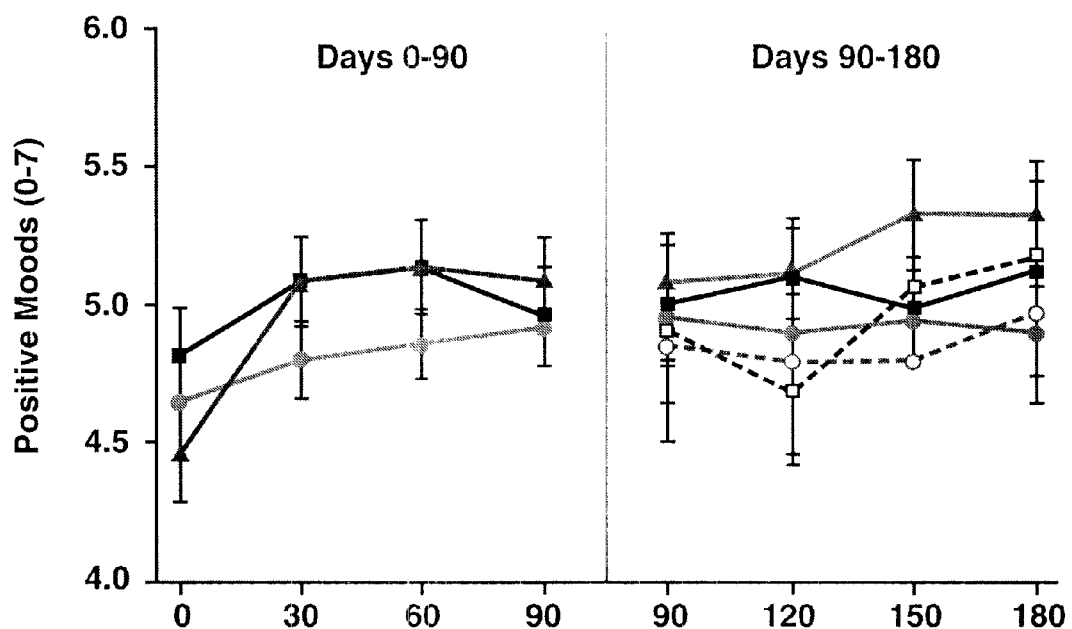
FIG. 23(a) is a graph showing positive mood scores on days 0 through 180 for hypogonadal men receiving either 5.0 g/day of AndroGel®, 7.5 g/day of Androgel®, 10.0 g/day of AndroGel®, or the testosterone patch.
Figure 23B:
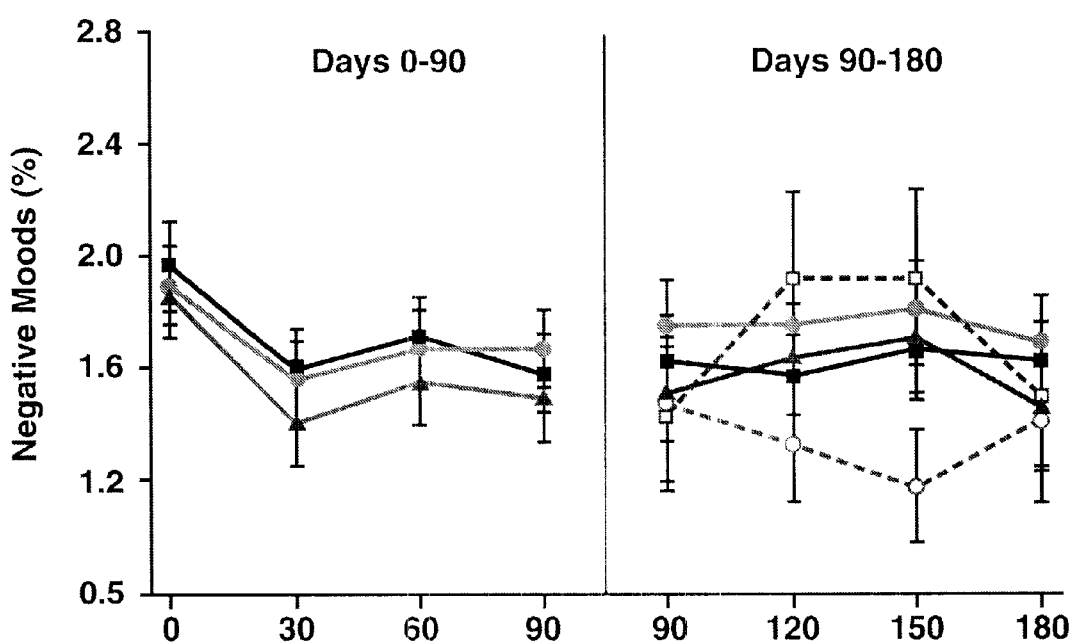
FIG. 23(b) is a graph showing negative mood scores on days 0 through 180 for hypogonadal men receiving either 5.0 g/day of AndroGel®, 7.5 g/day of Androgel®, 10.0 g/day of AndroGel®, or the testosterone patch.

The positive and negative mood summary responses to testosterone replacement therapy are shown in FIGS. 23(a) and 23(b). All three treatment groups had similar scores at baseline and all subjects as a group showed improvement in positive mood. Similarly, the negative mood summary scores were similar in the three groups at baseline and as a group the responses to transdermal testosterone applications showed significant decreases without showing between group differences. Specifically, positive mood parameters, such as sense of well being and energy level, improved and negative mood parameters, such as sadness and irritability, decreased. The improvement in mood was observed at day 30 and was maintained with continued treatment. The improvement in mood parameters was not dependent on the magnitude of increase in the serum testosterone levels. Once the serum testosterone increased into the low normal range, maximal improvement in mood parameters occurred. Thus, the responsiveness in sexual function and mood in hypogonadal men in response to testosterone therapy appeared to be dependent on reaching a threshold of serum testosterone at the low normal range.

4. Muscle Strength

Muscle strength was assessed on days 0, 90, and 180. The one-repetitive maximum ("1-RM") technique was used to measure muscle mass in bench press and seated leg press exercises The muscle groups tested included those in the hips, legs, shoulders, arms, and chest.

The 1-RM technique assesses the maximal force generating capacity of the muscles used to perform the test. After a 5–10 minute walking and stretching period, the test began with a weight believed likely to represent the patient's maximum strength. The test was repeated using increments of about 2–10 pounds until the patient was unable to lift additional weight with acceptable form Muscle strength was assessed in 167 out of the 227 patients. Four out of 16 centers did not participate in the muscle strength testing because of lack of the required equipment.

Figure 24A:
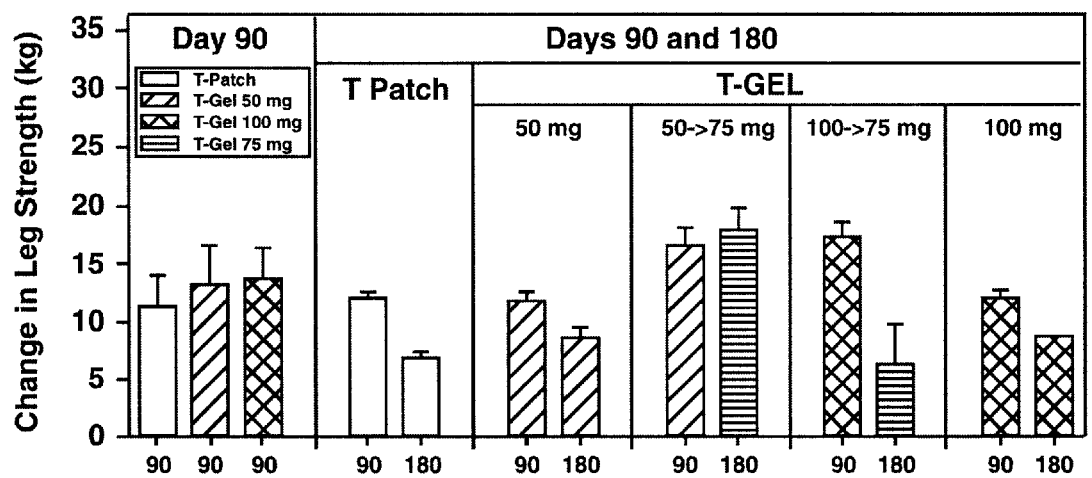
FIG. 24(a) is a bar graph showing the change in leg strength on days 90 and 180 for hypogonadal men receiving either 5.0 g/day of AndroGel®, 7.5 g/day of Androgel®, 10.0 g/day of AndroGel®, or the testosterone patch.
Figure 24B:
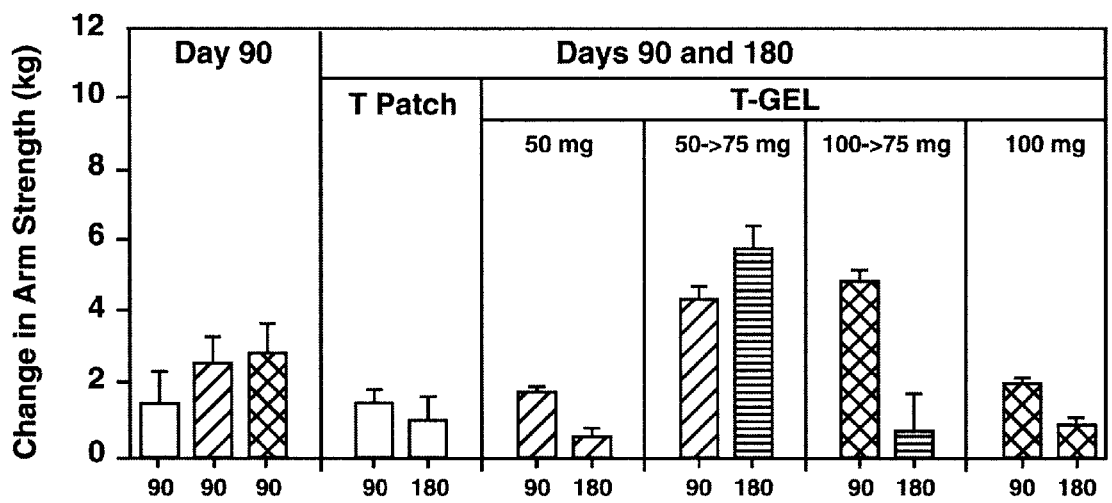
FIG. 24(b) is a bar graph showing the change in arm strength on days 90 and 180 for hypogonadal men receiving either 5.0 g/day of AndroGel®, 7.5 g/day of Androgel®, 10.0 g/day of AndroGel®, or the testosterone patch.

The responses of muscle strength testing by the arm/chest and leg press tests are shown in FIG. 24(a) and 24(b) and Table 29. There were no statistical significant differences in arm/chest or leg muscle strength among the three groups at baseline. In general, muscle strength improved in both the arms and legs in all three treatment groups without intergroup differences at both day 90 and 180. The results showed an improvement in muscle strength at 90 and 180 days, more in the legs than the arms, which was not different across treatment groups nor on the different days of assessment. Adjustment of the dose at day 90 did not significantly affect the muscle strength responses to transdermal testosterone preparations.

TABLE 29

Muscle Strength - Days 0, 90, and 180 Levels and Change (lbs.) from Day 0 to Day 90 and from Day 0 to Day 180 by Final Treatment Group

| Final Treatment Group | Study Day | Seated Leg Press | | Arm/Chest (Bench Press) | |
|---|---|---|---|---|---|
| | | N | Mean ± SD (lbs.) | N | Mean ± SD (lbs.) |
| 5.0 g/day T-gel | 0 | 37 | 356.8 ± 170.0 | 37 | 100.5 ± 37.4 |
| | 90 | 30 | 396.4 ± 194.3 | 31 | 101.2 ± 30.7 |
| | □0–90 | 30 | 25.8 ± 49.2 | 31 | 4.0 ± 10.0 |
| | 180 | 31 | 393.4 ± 196.6 | 31 | 99.7 ± 31.4 |
| | □0–180 | 31 | 19.9 ± 62.4 | 31 | 1.3 ± 13.0 |
| 7.5 g/day T-gel (from 5.0 g/day) | 0 | 16 | 302.8 ± 206.5 | 16 | 102.8 ± 48.9 |
| | 90 | 15 | 299.8 ± 193.9 | 15 | 109.5 ± 47.6 |
| | □0–90 | 15 | 17.0 ± 88.4 | 15 | 5.0 ± 21.3 |
| | 180 | 14 | 300.6 ± 203.0 | 14 | 108.5 ± 49.3 |
| | □0–180 | 14 | −0.1 ± 110.2 | 14 | 5.6 ± 30.4 |
| 7.5 g/day T-gel (From 10.0 g/day) | 0 | 14 | 363.4 ± 173.8 | 14 | 123.3 ± 54.7 |
| | 90 | 14 | 401.6 ± 176.6 | 14 | 134.6 ± 57.5 |
| | □0–90 | 14 | 38.2 ± 42.9 | 14 | 11.3 ± 10.5 |
| | 180 | 12 | 409.9 ± 180.2 | 14 | 132.3 ± 61.5 |
| | □0–180 | 12 | 33.9 ± 67.3 | 14 | 9.0 ± 18.7 |
| 10.0 g/day T-gel | 0 | 45 | 345.9 ± 186.9 | 43 | 114.7 ± 55.1 |
| | 90 | 43 | 373.5 ± 194.8 | 41 | 119.8 ± 54.2 |
| | □0–90 | 43 | 27.6 ± 45.1 | 41 | 4.6 ± 12.8 |
| | 180 | 36 | 364.4 ± 189.1 | 34 | 112.0 ± 45.5 |
| | □0–180 | 36 | 32.2 ± 72.3 | 34 | 1.9 ± 14.8 |
| T-Patch | 0 | 55 | 310.4 ± 169.7 | 54 | 99.2 ± 43.1 |
| | 90 | 46 | 344.9 ± 183.9 | 46 | 106.2 ± 44.0 |
| | □0–90 | 46 | 25.4 ± 37.0 | 46 | 3.2 ± 12.0 |
| | 180 | 36 | 324.8 ± 199.0 | 35 | 104.8 ± 44.8 |
| | □0–180 | 36 | 15.2 ± 54.7 | 35 | 2.3 ± 15.7 |

5. Body Composition

Body composition was measured by DEXA with Hologic 2000 or 4500A series on days 0, 90, and 180. These assessments were done in 168 out of 227 subjects because the Hologic DEXA equipment was not available at 3 out of 16 study centers. All body composition measurements were centrally analyzed and processed by Hologic (Waltham, Mass.).

Figure 25A:
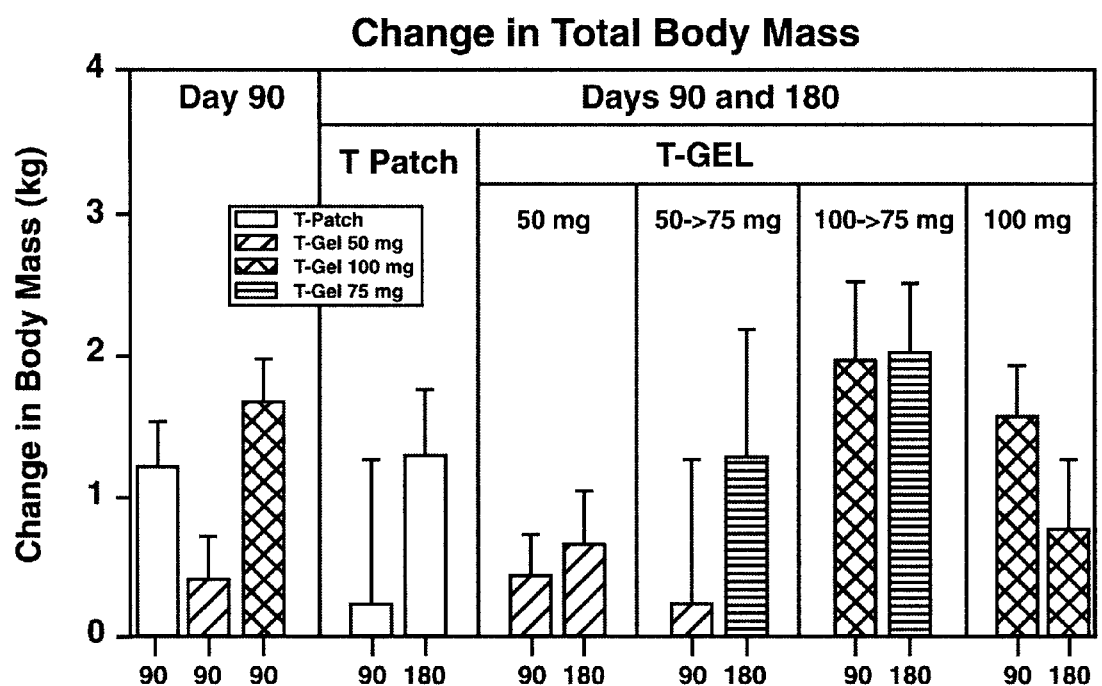
FIG. 25(a) is a bar graph showing the change in total body mass on days 90 and 180 for hypogonadal men receiving either 5.0 g/day of AndroGel®, 7.5 g/day of Androgel®, 10.0 g/day of AndroGel®, or the testosterone patch.
Figure 25B:
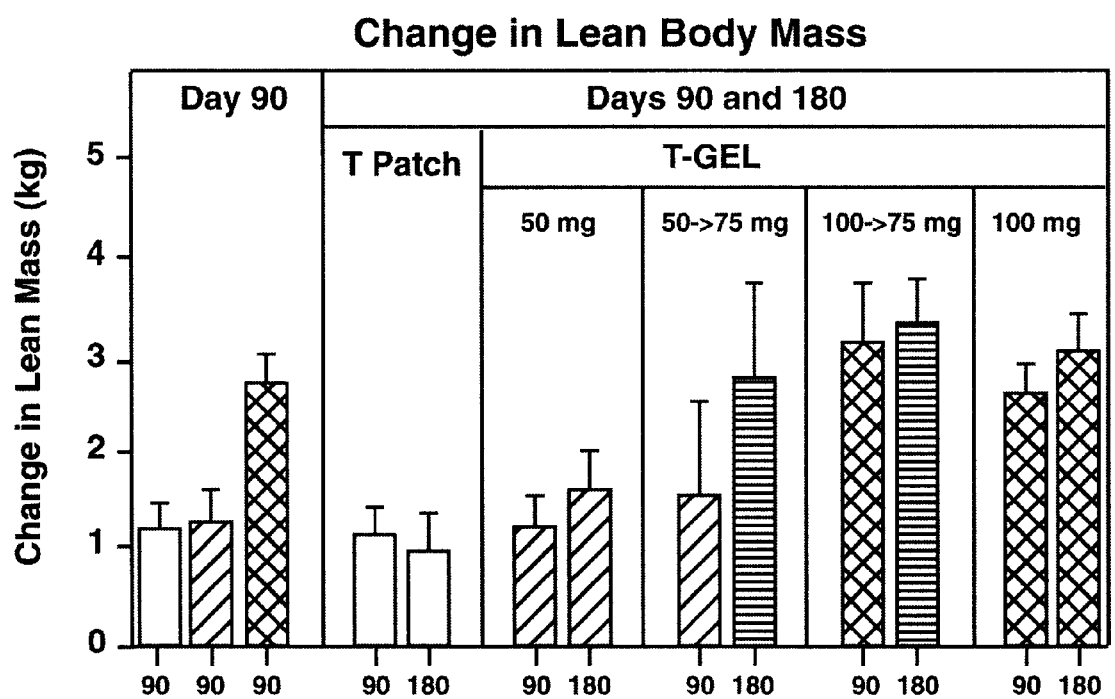
FIG. 25(b) is a bar graph showing the change in lean body mass on days 90 and 180 for hypogonadal men receiving either 5.0 g/day of AndroGel®, 7.5 g/day of Androgel®, 10.0 g/day of AndroGel®, or the testosterone patch.

A baseline, there were no significant differences in total body mass ("TBM"), total body lean mass ("TLN"), percent fat ("PFT"), and total body fat mass ("TFT") in the three treatment groups. As shown in FIGS. 25(a) and Table 30, all treatment groups incurred an overall increase in TBM. The increase in TBM was mainly due to the increases in TLN. FIG. 25(b) and Table 30 show that after 90 days of testosterone replacement the increase in TLN was significantly higher in the 10.0 g/day AndroGel® group than in the other two groups. At day 180, the increases in TLN were further enhanced or maintained in all AndroGel® treated groups, as well as in the testosterone patch group.

Figure 25C:
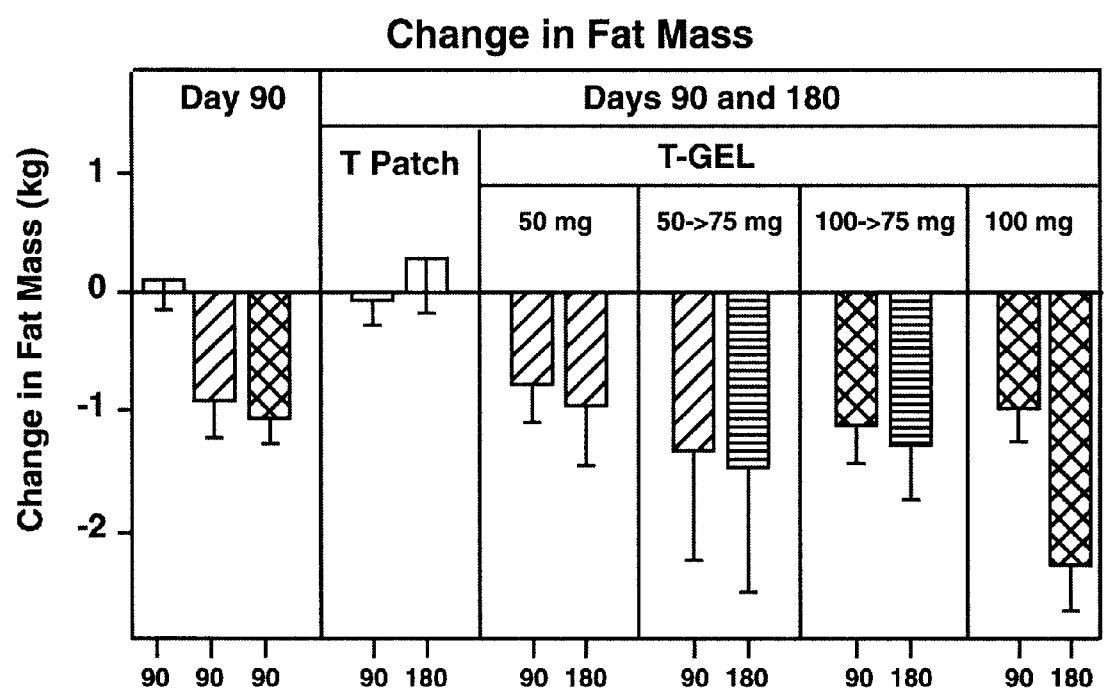
FIG. 25(c) is a bar graph showing the change in fat mass on days 90 and 180 for hypogonadal men receiving either 5.0 g/day of AndroGel®, 7.5 g/day of Androgel®, 10.0 g/day of AndroGel®, or the testosterone patch.
Figure 25D:
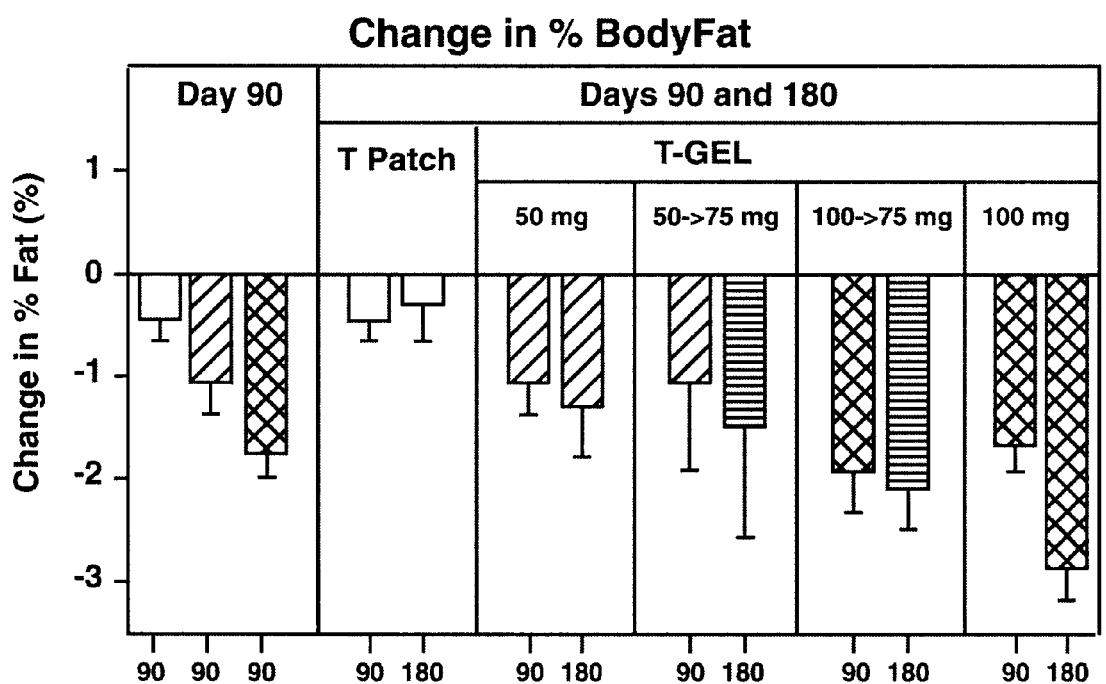
FIG. 25(d) is a bar graph showing the change in percent body fat on days 90 and 180 for hypogonadal men receiving either 5.0 g/day of AndroGel®, 7.5 g/day of Androgel®, 10.0 g/day of AndroGel®, or the testosterone patch.

FIGS. 25(c) and (d) show that the TFT and the PFT decreased in all transdernal AndroGel® treatment groups. At 90 days of treatment, TFT was significantly reduced by [in] the 5.0 g/day and 10.0 g/day AndroGel® groups, but was not changed in the testosterone patch group. This decrease was maintained at day 180. Correspondingly, at day 90 and 180, the decrease in PFT remained significantly lower in all AndroGel® treated groups but not significantly reduced in the testosterone patch group.

The increase in TLN and the decrease in TFT associated with testosterone replacement therapy showed significant correlations with the serum testosterone level attained by the testosterone patch and the different doses of AndroGel®. Testosterone gel administered at 10.0 g/day increased lean mass more than the testosterone patch and the 5.0 g/day AndroGel® groups. The changes were apparent on day 90 after treatment and were maintained or enhanced at day 180. Such changes in body composition was significant even though the subjects were withdrawn from prior testosterone therapy for six weeks. The decrease in TFT and PFT was also related to the serum testosterone achieved and were different across the treatment groups. The testosterone patch group did not show a decrease in PFT or TFT after 180 days of treatment. Treatment with AndroGel® (5.0 to 10.0 g/day) for 90 days reduced PFT and TFT. This decrease was maintained in the 5.0 and 7.5 g/day groups at 180 days but were further lowered with continued treatment with the higher dose of the AndroGel®.

replacement therapy. Total cholesterol levels which were initially high were lowered into the normal range (of each center's laboratory) at day 180 in 17.2, 20.4, and 12.2% of subjects on testosterone patch, AndroGel® 5.0 g/day and AndroGel® 10.0 g/day, respectively. Serum HDL-cholesterol levels (initially normal) were reduced to below the normal range (of each center's laboratory) in 9.8, 4.0, 9.1, and 12.5% of subjects at day 180 in the testosterone patch, AndroGel® 5.0, 7.5, and 10.0 g/day groups, respectively. There was no clinically significant changes in renal or liver function tests in any treatment group.

7. Skin Irritations

Skin iritation assessments were performed at every clinic visit using the following scale: 0=no erythema; 1=minimal erythema; 2=moderate erythema with sharply defined borders; 3=intense erythema with edema; and 4=intense erythema with edema and blistering/erosion.

Tolerability of the daily application of AndroGel® at the tested dosages was much better than with the permeation-enhanced testosterone patch. Minimal skin irritation (erythema) at the application site was noted in three patients in the AndroGel® 5.0 g/day group (5.7%) and another three in the AndroGel® 10.0 g/day group (5.3%). Skin irritation varying in intensity from minimal to severe (mild erythema to intense edema with blisters) occurred in 65.8% of patients in the patch group. Because of the skin irritation with the testosterone patch, 16 subjects discontinued the study; 14 of these had moderate to severe skin reactions at the medication sites. No patients who received AndroGel® discontinued the study because of adverse skin reactions. The open

TABLE 30

Mean Change in Body Composition Parameters (DEXA)
From Baseline to Day 90 and Baseline to Day 180
By Final Treatment Groups

| Final Treatment Group | N | TFT (g) | TLN (g) | TBM (g) | PFT |
|---|---|---|---|---|---|
| Mean Change from Day 0–Day 90 | | | | | |
| 5.0 g/day T-gel | 43 | −782 ± 2105 | 1218 ± 2114 | 447 ± 1971 | −1.0 ± 2.2 |
| 7.5 g/day (from 5.0 g/day) | 12 | −1342 ± 3212 | 1562 ± 3321 | 241 ± 3545 | −1.0 ± 3.1 |
| 7.5 g/day (from 10.0 g/day) | 16 | −1183 ± 1323 | 3359 ± 2425 | 2176 ± 2213 | −2.0 ± 1.5 |
| 10.0 g/day T-gel | 45 | −999 ± 1849 | 2517 ± 2042 | 1519 ± 2320 | −1.7 ± 1.8 |
| T-Patch | 52 | 11 ± 1769 | 1205 ± 1913 | 1222 ± 2290 | −0.4 ± 1.6 |
| Mean Change from Day 0–Day 180 | | | | | |
| 5.0 g/day T-gel | 38 | −972 ± 3191 | 1670 ± 2469 | 725 ± 2357 | −1.3 ± 3.1 |
| 7.5 g/day (from 5.0 g/day) | 13 | −1467 ± 3851 | 2761 ± 3513 | 1303 ± 3202 | −1.5 ± 3.9 |
| 7.5 g/day (from 10.0 g/day) | 16 | −1333 ± 1954 | 3503 ± 1726 | 2167 ± 1997 | −2.2 ± 1.7 |
| 10.0 g/day T-gel | 42 | −2293 ± 2509 | 3048 ± 2284 | 771 ± 3141 | −2.9 ± 2.1 |
| T-Patch | 34 | 293 ± 2695 | 997 ± 2224 | 1294 ± 2764 | −0.3 ± 2.2 |

6. Lipid profile and blood chemistry

The serum total, HDL, and LDL cholesterol levels at baseline were not significantly different in all treatment groups. With transdermal testosterone replacement, there were no overall treatment effects nor inter-group differences in serum concentrations of total, HDL- and LDL-cholesterol (FIG. 5(d)) and triglycerides (data not shown). There was a significant change of serum total cholesterol concentrations as a group with time (p=0.0001), the concentrations on day 30, 90, and 180 were significantly lower than day 0.

Approximately 70 to 95% of the subjects had no significant change in their serum lipid profile during testosterone system and the lower concentration of alcohol in the AndroGel® formulation markedly reduced skin irritation resulting in better tolerability and continuation rate on testosterone replacement therapy.

Moreover, based on the difference in the weight of the dispensed and returned AndroGel® bottles, the mean compliance was 93.1% and 96.0% for the 5.0 g/day and 10.0 g/day AndroGel® groups during days 1–90, respectively. Compliance remained at over 93% for the three AndroGel® groups from days 91–180. In contrast, based on counting the patches returned by the subjects, the testosterone patch compliance was 65% during days 1–90 and 74% during days 91–180. The lower compliance in the testosterone patch group was mostly due to skin reactions from the subjects' records.

TABLE 31

Incidence of Skin-Associated Adverse Events: Day 1 to Day 180 in Patients Who Remained on Initial Treatment

|  | 5.0 g/day T-gel N = 53 | 10.0 g/day T-gel N = 57 | T-Patch N = 73 |
|---|---|---|---|
| Total | 16 (30.2%) | 18 (31.6%) | 50 (68.5%) |
| Application Site Reaction | 3 (5.7% | 3 (5.3%) | 48 (65.8%) |
| Acne | 1 (1.9%) | 7 (12.3%) | 3 (4.1%) |
| Rash | 4 (7.5%) | 4 (7.0%) | 2 (2.7%) |
| Skin Disorder | 2 (3.8%) | 1 (1.8%) | 1 (1.4%) |
| Skin Dry | 2 (3.8) | 0 (0.0%) | 1 (1.4%) |
| Sweat | 0 (0.0%) | 2 (3.5%) | 0 (0.0%) |
| Reaction Unevaluable | 2 (3.6%) | 1 (1.7%) | 0 (0.0%) |
| Cyst | 0 (0.0%) | 0 (0.0%) | 2 (2.7%) |

Example 2

Gel Delivery Dosage Forms and Devices

The present invention is also directed to a method for dispensing and packaging the gel. In one embodiment, the invention comprises a hand-held pump capable of delivering about 2.5 g of testosterone gel with each actuation. In another embodiment, the gel is packaged in foil packets comprising a polyethylene liner. Each packet holds about 2.5 g of testosterone gel. The patient simply tears the packet along a perforated edge to remove the gel. However, because isopropyl myristate. binds to the polyethylene liner, additional isopropyl myristate is added to the gel in order to obtain a pharmaceutically effective gel when using this delivery embodiment. Specifically, when dispensing the gel via the foil packet, about 41% more isopropyl myristate is used in the gel composition (i.e., about 0.705 g instead of about 0.5 g in Table 5), to compensate for this phenomenon.

The composition can also be dispensed from a rigid multi-dose container (e.g., with a hand pump) having a larger foil packet of the composition inside the container. Such larger packets also comprise a polyethylene liner as above.

Both embodiments permit a patient to deliver accurate but incremental amounts of gel (e.g., either 2.5 g, 5.0 g, 7.5 g, etc.) to the body. These delivery mechanisms thus permit the gel to be administered in unit dose form depending on the particular needs and characteristics of the patient.

Although the invention has been described with respect to specific embodiments and examples, it should be appreciated that other embodiments utilizing the concept of the present invention are possible without departing from the scope of the invention. Th present invention is defined by the claimed elements, and any and all modifications, variations, or equivalents that fall within the true spirit and scope of the underlying principles.

We claim:

1. A pharmaceutical composition, consisting essentially of:
    a. about 0.5% to about 10% testosterone;
    b. about 30% to about 98% alcohol selected from the group consisting of ethanol and isopropanol;
    c. about 0.1% to about 5% isopropyl myristate;
    d. about 1% to about 5% sodium hydroxide; and
    e. about 0.1% to about 5% of a gelling agent, wherein the percentages of components are weight to weight of the composition.

2. The composition as recited in claim 1, wherein the testosterone is present in a concentration selected from the group consisting of about 0.5%, 1%, 2%, 3%, 4%, 5%, 6%, 7%, 8%, 9%, and 10% weight of the composition.

3. The composition as recited in claim 1, wherein the composition is contained in a packet selected from the group consisting of a unit dose packet or multiple dose packet.

4. The composition as recited in claim 1, therein the isopropyl myristate is present in a concentration selected from the group consisting of about 0.5%, 1%, 2%, 3%, 4%, and 5% weight to weight of the composition.

5. The composition as recited in claim 1, wherein the isopropyl myristate is present in a concentration of about 0.5% weight to weight of the composition.

6. The composition as recited in claim 1, wherein the gelling agent is selected from the group consisting of polyacrylic acid and carboxymethylcellulose present in a concentration of about 0.1% to about 5% weight to weight of the composition.

7. The composition as recited in claim 1, wherein the composition is the form of a gel.

8. The composition as recited in claim 1, wherein the gelling agent is polyacrylic acid present in a concentration of about 1% weight to weight of the composition.

9. A hydroalcoholic gel formulation, consisting essentially of:
    a. about 1% to about 2% testosterone;
    b. about 50% to about 75% ethanol;
    c. about 0.5% to about 2% isopropyl myristate;
    d. about 1% to about 3% sodium hydroxide;
    e. about 0.5% to about 2% polyacrylic acid; and
    f. water in an amount sufficient to make the formulation 100%;

wherein the percentages of components are weight to weight of the formulation.

10. A unit dose packet comprising inner and outer surfaces, and a pharmaceutical composition inside the packet, the composition consisting essentially of:
    a. about 0.5% to about 5% testosterone;
    b. about 30% to about 98% ethanol;
    c. about 0.1% to about 5% isopropyl myristate;
    d. about 1% to about 5% sodium hydroxide; and
    e. about 0.1% to about 5% of a gelling agent;

wherein the percentages of components are weight to weight of the composition.

11. The packet as recited in claim 10, wherein the composition weighs about 1.0 gram to about 10.0 grams.

12. The packet as recited in claim 10, wherein the composition weighs about 2.5 grams to about 5.0 grams.

13. The packet as recited in claim 10, wherein the composition is in a form of a gel.

14. The packet as recited in claim 10, wherein the testosterone is present in a concentration selected from the group consisting of about 0.5%, 1%, 2%, 3%, 4%, and 5% weight to weight of the composition.

15. The packet recited claim 10, wherein the isopropyl myristate is present in a concentration of about 0.5% weight to weight of the composition.

16. The packet as recited in claim 10, wherein the gelling agent is selected from the group consisting of polyacrylic acid and carboxymetliylcellulose.

17. The packet as recited in claim 10, wherein the gelling agent is about 1% polyacrylic acid weight to weight of the composition.

18. A method for administering an active agent to a human subject in need thereof, the method comprising:
  a. providing a phannaceutical composition consisting essentially of:
     (i) about 0.5% to about 5% testosterone;
     (ii) about 0.1% to about 5% of a gelling agent;
     (iii) about 0.1% to about 5% isopropyl myristate;
     (iv) about 1% to about 5% sodium hydroxide; and
     (v) about 30% to about 98% alcohol selected form the group consisting of ethanol and isopropanol;
     wherein the percentages are weight to weight of the composition; and
  b. applying a daily dose of the composition to skin of the subject in an amount sufficient for the testosterone to reach the bloodstream of the subject so as to achieve a serum concentration within a range between about 300 ng testosterone per dl serum to about 1050 ng testosterone per dl serum within at least about 36 hours of daily dosing of the composition.

19. The method as recited in claim 18, wherein the testosterone is present in a concentration of about 1% weight to weight of the composition.

20. The method as recited in claim 18, wherein the testosterone is present in a concentration of about 2% weight to weight of the composition.

21. The method as recited in claim 18, wherein the isopropyl myristate is present in a concentration of about 0.5% weight to weight of the composition.

22. The method as recited in claim 18, wherein the alcohol is ethanol present in a concentration of about 72.5% weight to weight of the composition.

23. The method as recited in claim 18, wherein the gelling agent is selected from the group consisting of polyacrylic acid and carboxymethylcellulose present in a concentration of about 0.1% to about 5% weight to weight of the composition.

24. The method as recited in claim 18, wherein the composition is the form of a gel.

25. The method as recited in claim 18, wherein the gelling agent is polyacrylic acid present in a concentration of about 1% weight to weight of the composition.

26. The method as recited in claim 18, wherein the serum testosterone concentration is substantially maintained at about 400 ng/dl or higher for at least 24 hours after the subject has applied the daily dose of the composition for at least 2 consecutive days.

27. The method as recited in claim 18, wherein the serum testosterone concentration is substantially maintained between about 500 ng/dl and about 1050 ng/dl for at least 24 hours after the subject has applied the daily dose of the composition for at least 30 consecutive days.

28. The method as recited in claim 18, wherein the serum testosterone concentration is substantially maintained at between about 600 ng/dl to about 1050 ng/dl for at least 24 hours after the subject has applied the daily dose of the composition for at least 30 consecutive days.

29. The method as recited in claim 18, wherein the serum testosterone concentration is substantially maintained at between about 700 ng/dl to about 1050 ng/dl for at least 24 hours after the subject has applied the daily dose of the composition for at least 30 consecutive days.

30. The method as recited in claim 18, wherein the dose is applied in a single or in divided doses.

31. A method for administering an active agent to a human subject in need thereof, the method comprising:
  a. providing a pharmnaceutical composition consisting essentially of:
     (i) about 0.5% to about 5% testosterone;
     (ii) about 0.1% to about 5% isopropyl myristate;
     (iii) about 30% to about 98% of an alcohol selected from the group consisting of ethanol and isopropanol; and
     (iv) about 0.1% to about 5% of a gelling agent;
     wherein the percentages are weight to weight of the composition; and
  b. applying a daily dose of the composition to skin of the subject in an amount sufficient for the testosterone to reach the bloodstream of the subject wherein serum concentration is substantially maintained between about 400 ng testosterone per dl serum to about 1050 ng testosterone per dl serum for at least 24 hours after the subject has applied the daily dose of the composition for at least 2 consecutive days.

32. The method as recited in claim 31, wherein the testosterone is present in a concentration of about 1% weight to weight of the composition.

33. The method as recited in claim 31, wherein the testosterone is present in a concentration of about 2% weight to weight of the composition.

34. The method as recited in claim 31, wherein the isopropyl myristate is present in a concentration of about 0.5% weight to weight off the composition.

35. The method as recited in claim 31, wherein the alcohol is present in a concentration of about 72.5% weight to weight of the composition.

36. The method as recited in claim 31, wherein the gelling agent is selected from the group consisting of polyacrylic acid and carboxymethylcellulose.

37. The method as recited in claim 31, wherein the composition is in the form of a gel.

38. The method as recited in claim 36, wherein the gelling agent is polyacrylic acid present in a concentration of about 1% weight to weight of the composition.

39. The method as recited in claim 31, wherein the serum testosterone concentration is maintained between about 500 ng/dl and about 1050 ng/dl for at least 24 hours after the subject has applied the daily dose of the composition for at least 30 consecutive days.

40. The method as recited in claim 31, wherein the serum testosterone concentration is maintained at between about 600 ng/dl to about 1050 ng/dl for at least 24 hours after the subject has applied the daily dose of the composition for at least 30 consecutive days.

41. The method as recited in claim 31, wherein the serum testosterone concentration is maintained at between about 700 ng/dl to about 1050 ng/dl for at least 24 hours after the subject has applied the daily dose of the composition for at least 30 consecutive days.

42. The method as recited in claim 31, wherein the dose is applied in a single or in divided doses.

* * * * *

UNITED STATES PATENT AND TRADEMARK OFFICE
CERTIFICATE OF CORRECTION

PATENT NO. : 6,503,894 B1
DATED : January 7, 2003
INVENTOR(S) : Dudley, Robert E., Kottayil, S. George and Palatchi, Olivier It is certified that error appears in the above-identified patent and that said Letters Patent is hereby corrected as shown below:

Column 5,
Line 23, delete "fluoxyrnesterone" and insert -- fluoxymesterone --, therefor.
Line 33, delete "while" and insert -- While --, therefor.

Column 7,
Line 55, delete "transdernal" and insert -- transdermal --, therefor.

Column 12,
Line 2, delete "chiormadinone" and insert -- chlormadinone --, therefor.

Column 15,
Line 43, delete "urine." and insert -- urine --, therefor.

Column 16,
Line 2, delete "received." and insert -- received --, therefor.

Column 19,
Line 22, delete "transdermnal" and insert -- transdermal --, therefor.

Column 21,
Line 12, delete "under responders" and insert -- under-responders --, therefor.

Column 30,
Line 29, delete "assay," and insert -- assay --, therefor.

Column 33,
Line 67, delete "hypogpnadism" and insert -- hypogonadism --, therefor.

Column 45,
Line 58, delete "exercises" and insert -- exercises. --, therefor.
Line 66, delete "form" and insert -- form. --, therefor.

Column 47,
Line 4, delete "transdernal" and insert -- transdermal --, therefor.
Line 5, delete "by [in]" and insert -- in --, therefor.

Column 49,
Line 33, delete "myristate. binds" and insert -- myristate binds --, therefor.
Line 54, delete "Th" and insert -- The --, therefor.

UNITED STATES PATENT AND TRADEMARK OFFICE
CERTIFICATE OF CORRECTION

PATENT NO. : 6,503,894 B1
DATED : January 7, 2003
INVENTOR(S) : Dudley, Robert E., Kottayil, S. George and Palatchi, Oliver It is certified that error appears in the above-identified patent and that said Letters Patent is hereby corrected as shown below:

Column 49 (cont'd),
Line 66, after "d. about 1% to about 5%" insert -- 0.1 N --, therefor.

Column 50,
Line 32, after "d. about 1% to about 3%" insert -- 0.1 N --, therefor.
Line 45, after "d. about 1% to about 5%" insert -- 0.1 N --, therefor.

Column 51,
Line 3, after "a. providing a", delete "phannaceutical" and insert -- pharmaceutical --, therefor.
Line 8, after "(iv.) about 1% to about 5%" insert -- 0.1 N -- therefor.

Column 52,
Line 5, after "a. providing a", delete "pharmnaceutical" and insert -- pharmaceutical --, therefor.

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,503,894 B1 | Page 1 of 1 |
| APPLICATION NO. | : 09/651777 | |
| DATED | : January 7, 2003 | |
| INVENTOR(S) | : Dudley et al. | |

It is certified that error appears in the above-identified patent and that said Letters Patent is hereby corrected as shown below:

Item (75) Inventors, change the listing of inventors from "Dudley; Robert E., Kenilworth, IL (US); Kottayil; S. George, Long Grove, IL (US); Palatchi; Olivier, L'Hay les Roses (FR)" to read --Dudley; Robert E., Kenilworth, IL (US); Drouin; Dominique, Paris (FR)--.

Signed and Sealed this

Twenty-second Day of May, 2007

JON W. DUDAS
*Director of the United States Patent and Trademark Office*